United States Patent
Chen et al.

(10) Patent No.: US 10,421,748 B2
(45) Date of Patent: Sep. 24, 2019

(54) 2-OXINDOLE COMPOUNDS

(71) Applicant: CHEMOCENTRYX, INC., Mountain View, CA (US)

(72) Inventors: Xi Chen, East Palo Alto, CA (US); Dean R. Dragoli, Los Altos, CA (US); Pingchen Fan, Fremont, CA (US); Manmohan Reddy Leleti, Dublin, CA (US); Rebecca M. Lui, Santa Clara, CA (US); Viengkham Malathong, Belmont, CA (US); Jay P. Powers, Pacifica, CA (US); Rajinder Singh, Belmont, CA (US); Hiroko Tanaka, Mountain View, CA (US); Ju Yang, Palo Alto, CA (US); Chao Yu, Sunnyvale, CA (US); Penglie Zhang, Foster City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 15/914,900

(22) Filed: Mar. 7, 2018

(65) Prior Publication Data
US 2019/0016709 A1 Jan. 17, 2019

Related U.S. Application Data

(63) Continuation of application No. 15/408,896, filed on Jan. 18, 2017, now abandoned.

(60) Provisional application No. 62/280,969, filed on Jan. 20, 2016.

(51) Int. Cl.
| | |
|---|---|
| *C07D 209/34* | (2006.01) |
| *C07D 405/04* | (2006.01) |
| *A61K 31/404* | (2006.01) |
| *A61K 31/4439* | (2006.01) |
| *C07D 405/14* | (2006.01) |
| *C07D 401/04* | (2006.01) |

(52) U.S. Cl.
CPC ......... *C07D 405/14* (2013.01); *C07D 209/34* (2013.01); *C07D 401/04* (2013.01); *C07D 405/04* (2013.01)

(58) Field of Classification Search
CPC .. C07D 209/34; C07D 405/04; A61K 31/404; A61K 31/4439
See application file for complete search history.

(56) References Cited

U.S. PATENT DOCUMENTS

| | | |
|---|---|---|
| 2004/0171654 A1 | 9/2004 | Ugashe et al. |
| 2007/0203184 A1 | 8/2007 | Foulon et al. |
| 2010/0069384 A1 | 3/2010 | Foulon et al. |
| 2013/0102604 A1 | 4/2013 | Chen et al. |
| 2013/0225580 A1 | 8/2013 | Chen et al. |
| 2015/0291623 A1 | 10/2015 | Chafeev et al. |

OTHER PUBLICATIONS

International Search Report and Written Opinion corresponding to PCT/US2017/013899 dated Apr. 7, 2017, 9 pages.
Extended European Search Report corresponding to EP 17741838.1 dated Jun. 24, 2019; 9 pages.

*Primary Examiner* — Karen Cheng
(74) *Attorney, Agent, or Firm* — Mintz Levin Cohn Ferris Glovsky and Popeo PC

(57) ABSTRACT

Oxindole compounds useful for the treatment of CCR(9) mediated conditions or diseases are provided.

43 Claims, No Drawings

2-OXINDOLE COMPOUNDS

CROSS-REFERENCES TO RELATED APPLICATIONS

This application is continuation of U.S. patent application Ser. No. 15/408,896 filed Jan. 18, 2017, which is an application claiming benefit under 35 U.S.C. § 119(e) of U.S. Provisional Application No. 62/280,969 filed Jan. 20, 2016, each of which are herein incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present disclosure provides compounds and pharmaceutical compositions containing one or more of those compounds or their pharmaceutically acceptable salts, that are effective in inhibiting the binding or function of chemokines to the CCR9 chemokine receptor. As antagonists or modulators of the CCR9 chemokine receptor, the compounds and compositions can have utility in treating various immune disorder conditions and diseases.

Chemokines, also known as chemotactic cytokines, are a group of small molecular-weight proteins that are released by a wide variety of cells and have a variety of biological activities. Chemokines attract various types of cells of the immune system, such as macrophages, T cells, eosinophils, basophils and neutrophils, and cause them to migrate from the blood to various lymphoid and none-lymphoid tissues. They mediate infiltration of inflammatory cells to sites of inflammation, and are responsible for the initiation and perpetuation of many inflammation diseases (reviewed in Schall, *Cytokine*, 3:165-183 (1991), Schall et al., *Curr. Opin. Immunol.*, 6:865-873 (1994)).

In addition to stimulating chemotaxis, chemokines can induce other changes in responsive cells, including changes in cell shape, granule exocytosis, integrin up-regulation, formation of bioactive lipids (e.g., leukotrienes), respiratory burst associated with leukocyte activation, cell proliferation, resistance to induction of apoptosis and angiogenesis. Thus, chemokines are early triggers of the inflammatory response, causing inflammatory mediator release, chemotaxis and extravasation to sites of infection or inflammation. They are also stimulators of a multitude of cellular processes that bear important physiological functions as well as pathological consequences.

Chemokines exert their effects by activating chemokine receptors expressed by responsive cells. Chemokine receptors are a class of G-protein coupled receptors, also known as seven-transmembrane receptors, found on the surface of a wide variety of cell types such as leukocytes, endothelial cells, smooth muscle cells and tumor cells.

Chemokines and chemokine receptors are expressed by intrinsic renal cells and infiltrating cells during renal inflammation (Segerer et al., *J. Am. Soc. Nephrol.*, 11:152-76 (2000); Morii et al., *J. Diabetes Complications*, 17:11-5 (2003); Lloyd et al. *J. Exp. Med.*, 185:1371-80 (1997); Gonzalez-Cuadrado et al. *Clin. Exp. Immunol.*, 106:518-22 (1996); Eddy & Giachelli, *Kidney Int.*, 47:1546-57 (1995); Diamond et al., *Am. J. Physiol.*, 266:F926-33 (1994)).

T lymphocyte (T cell) infiltration into the small intestine and colon has been linked to the pathogenesis of Coeliac diseases, food allergies, rheumatoid arthritis, human inflammatory bowel diseases (IBD) which include Crohn's disease and ulcerative colitis. Blocking trafficking of relevant T cell populations to the intestine can lead to an effective approach to treat human IBD. More recently, chemokine receptor-9 (CCR(9)) has been noted to be expressed on gut-homing T cells in peripheral blood, elevated in patients with small bowel inflammation such as Crohn's disease and coeliac disease. The only CCR(9) ligand identified to date, TECK (thymus-expressed chemokine) is expressed in both the small and large intestines and the ligand receptor pair is now thought to play a pivotal role in the development of IBD. In particular, this pair mediates the migration of disease causing inflammatory cells to the intestine. See for example, Zaballos et al., *J. Immunol.*, 162(10):5671-5675 (1999); Kunkel et al., *J. Exp. Med.*, 192(5):761-768 (2000); Papadakis et al., *J. Immunol.*, 165(9):5069-5076 (2000); Papadakis et al., *Gastroenterology*, 121(2):246-254 (2001); Campbell et al., *J. Exp. Med.*, 195(1):135-141 (2002); Wurbel et al., *Blood*, 98(9):2626-2632 (2001); and Uehara et al., *J. Immunol*, 168(6):2811-2819 (2002); Rivera-Nieves et al., *Gastroenterology*, 2006 November; 131(5):1518-29; and Kontoyiannis et al., *J. Exp. Med., Vol.* 196, Number 12, Dec. 16, 2002. In addition CCR(9) bearing lymphocytes have been show to mediate the pathology of filariasis (lymphatic filarial disease) and inhibition of CCR(9) has been correlated with reduction of the pathology associated with such conditions. See for example Babu et al., Journal of Infectious Diseases, 191: 1018-26, 2005.

The identification of compounds that modulate the function of CCR(9) represents an attractive new family of therapeutic agents for the treatment of inflammatory and other conditions and diseases associated with CCR(9) activation, such as inflammatory bowel disease.

BRIEF SUMMARY OF THE INVENTION

The present invention is directed to compounds and pharmaceutically acceptable salts thereof, compositions, and methods useful in modulating the function of CCR(9). The compounds and salts thereof, compositions, and methods described herein can be useful in treating or preventing chemokine-mediated conditions or diseases, including certain inflammatory and immunoregulatory disorders and diseases.

The compounds of the present disclosure have been shown to modulate CCR(9), as shown in the examples.

In one aspect, the present compounds may be represented by formula (I):

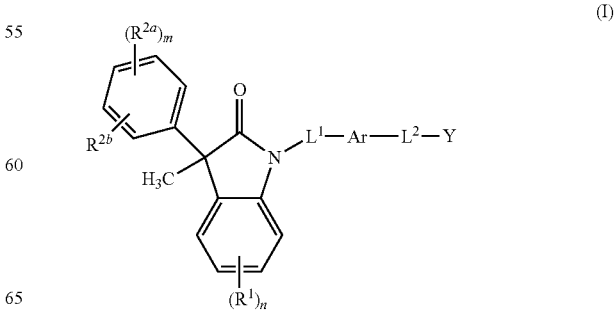

or a pharmaceutically acceptable salt thereof, wherein
Ar is a 5- to 10-membered aromatic or heteroaromatic ring, optionally substituted with from one to three $R^3$;
$L^1$ is selected from the group consisting of a bond, $C_{1-6}$ alkylene, and $C_{1-6}$ heteroalkylene,
$L^2$ is selected from the group consisting of a bond, $C_{1-6}$ alkylene, and $C_{1-6}$ heteroalkylene,
Y is $CO_2H$ or a carboxylic acid bioisostere;
each $R^1$ and each $R^{2a}$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl, wherein the alkyl, cycloalkyl and alkenyl portions are optionally substituted with from one to three members selected from fluoro, OH, CN, $C_{1-3}$ alkyl, $C_{1-3}$ haloalkyl, and $C_{1-3}$ alkoxy;
$R^{2b}$ is selected from the group consisting of H, halogen, cyano, $C_{1-6}$ alkyl, $C_{1-6}$ alkoxy, $C_{3-6}$ cycloalkyl, and $C_{2-6}$ alkenyl, wherein the alkyl, cycloalkyl and alkenyl portions are optionally substituted with from one to three members selected from fluoro, CN, $C_{1-3}$ alkyl, $C_{1-3}$ haloalkyl, and $C_{1-3}$ alkoxy;
or optionally one $R^{2a}$ and $R^{2b}$ when on adjacent vertices of a phenyl ring, may be joined together to form a 5- or 6-membered heterocycloalkyl ring having one or two ring vertices independently selected from O, N and S, wherein said heterocycloalkyl ring is optionally substituted with from one to three members selected from fluoro and $C_{1-3}$ alkyl;
each $R^3$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl;
the subscript m is an integer of from 0 to 4; and
the subscript n is an integer of from 0 to 3.

In another aspect, the present disclosure provides compositions useful in modulating chemokine activity. In one embodiment, a composition according to the present disclosure comprises a compound according to the disclosure and a pharmaceutically acceptable carrier or excipient.

In yet another aspect, the present disclosure provides methods of modulating chemokine function in a cell, comprising contacting the cell with a therapeutically effective amount of a compound or composition according to the disclosure.

In still another aspect, the present disclosure provides methods for modulating chemokine function, comprising contacting a chemokine receptor with a therapeutically effective amount of a compound or composition according to the disclosure.

In still another aspect, the present disclosure provides methods for treating a chemokine-mediated condition or disease, comprising administering to a subject a safe and effective amount of a compound or composition according to the disclosure. The administering may be oral, parenteral, rectal, transdermal, sublingual, nasal or topical. In some aspects the compound may be administered in combination with an anti-inflammatory or analgesic agent.

In addition to the compounds provided herein, the present disclosure further provides pharmaceutical compositions containing one or more of these compounds, as well as methods for the use of these compounds in therapeutic methods, primarily to treat diseases associated with chemokine signaling activity. The CCR(9) mediated disease or condition may be inflammatory bowel diseases, an allergic disease, psoriasis, atopic dermatitis, asthma, fibrotic diseases, graft rejection, GvHD, Sjogren syndrome, immune mediated food allergies, autoimmune diseases, Celiac disease, rheumatoid arthritis, thymoma, thymic carcinoma, leukemia, solid tumor, or acute lymphocytic leukemia, melanoma, primary sclerosing cholangitis, hepatitis and inflammatory hepatic disease, post-operative ileus, Crohn's disease or ulcerative colitis.

BRIEF DESCRIPTION OF THE DRAWINGS

NOT APPLICABLE

DETAILED DESCRIPTION OF THE INVENTION

General

The present disclosure is directed to compounds and salts thereof, compositions and methods useful in the modulation of chemokine receptor function, particularly CCR(9) function. Modulation of chemokine receptor activity, as used herein in its various forms, is intended to encompass antagonism, agonism, partial antagonism, inverse agonism and/or partial agonism of the activity associated with a particular chemokine receptor, preferably the CCR(9) receptor. Accordingly, the compounds of the present disclosure are compounds which modulate at least one function or characteristic of mammalian CCR(9), for example, a human CCR(9) protein. The ability of a compound to modulate the function of CCR(9), can be demonstrated in a binding assay (e.g., ligand binding or agonist binding), a chemotaxis (migration assay), a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

Abbreviations and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkane" or "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycylic ring system. Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkane group can be attached to the remainder of the molecule through a ring carbon or a heteroatom.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively. The term "heteroalkylene" refers to an alkylene group in which one or two carbon atoms are replaced by N, O, or S.

As used herein, a wavy line, "⁓", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The term "di-(C$_{1-4}$alkyl)amino-C$_{1-4}$ alkyl" refers to an amino group bearing two C$_{1-4}$ alkyl groups that can be the same or different (e.g., methyl, ethyl, propyl, isopropyl, n-butyl, sec-butyl, isobutyl and tert-butyl) and which is attached to the remainder of the molecule through a C$_{1-4}$ alkyl group (a one to four carbon alkylene linking group). Examples of di-(C$_{1-4}$ alkyl)amino-C$_{1-4}$ alkyl groups include dimethylaminomethyl, 2-(ethyl(methyl)amino)ethyl, 3-(dimethylamino)butyl, and the like.

The terms "halo" or "halogen," by themselves or as part of another substituent, mean, unless otherwise stated, a fluorine, chlorine, bromine, or iodine atom. Additionally, terms such as "haloalkyl" and "haloalkoxy," are meant to include monohalo- and polyhalo-versions of alkyl and alkoxy, respectively. For example, the term "C$_{1-4}$ haloalkyl" is mean to include trifluoromethyl, 2,2,2-trifluoroethyl, 4-chlorobutyl, 3-bromopropyl, and the like.

The term "aryl" or "aromatic ring" means, unless otherwise stated, a polyunsaturated, typically aromatic, hydrocarbon group which can be a single ring or multiple rings (up to three rings) which are fused together or linked covalently. Similarly, the terms "heteroaryl" and "heteroaromatic ring" refer to aryl groups (or rings) that contain from one to five heteroatoms selected from N, O, and S, wherein the nitrogen and sulfur atoms are optionally oxidized, and the nitrogen atom(s) are optionally quaternized. A heteroaryl group or heteroaromatic ring can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

As used herein, the term "heteroatom" is meant to include oxygen (O), nitrogen (N), sulfur (S) and silicon (Si).

The term "carboxylic acid bioisostere" refers to a group having polar and/or acidic character to act as a replacement for a carboxylic acid. A variety of bioisosteres are known for carboxylic acids, including, hydroxamic acids, hydroxamic esters, phosphonic acids, phosphinic acids, sulfonic acids, sulfinic acids, sulfonamides, acyl sulfonamides, acylureas, sulfonylureas, cyclopentane-1,2-diones, substituted phenols, and heterocycle-based bioisosteres as provided below:

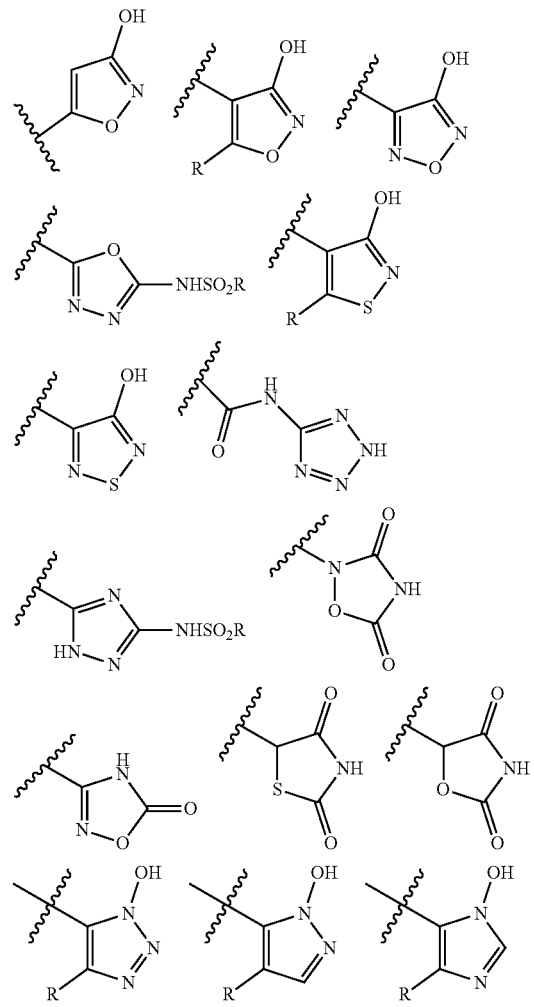

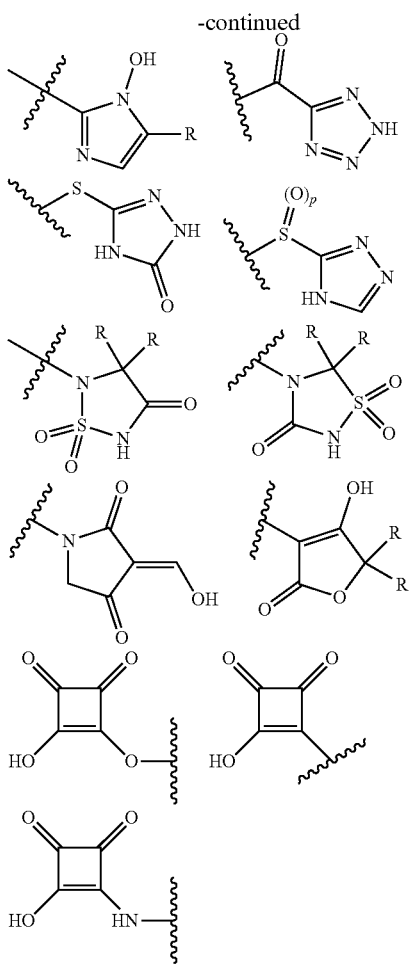

wherein p is 0, 1 or 2 and wherein each R group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, or $C_1$-$C_4$ alkyl-O—$C_1$-$C_4$ alkyl.

Other examples of bioisosteres of a carboxylic acid are a tetrazolyl or tetrazolonyl, wherein the tetrazolyl or tetrazolonyl is optionally substituted with $C_{1-6}$ alkyl, $C_{1-6}$ haloalkyl, $C_{1-6}$ hydroxyalkyl, —$C_{1-6}$ alkoxy or $C_{1-4}$ alkyl-O—$C_{1-4}$ alkyl. Still other examples of carboxylic acid bioisosteres are described in the *Journal of Medicinal Chemistry*, 2016, 59, 3183-3203 which are hereby incorporated by reference.

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure. Substitution with heavier isotopes such as deuterium, i.e. $^2$H, may afford certain therapeutic advantages resulting from greater metabolic stability. For example, in vivo half-life may increase or dosage requirements may be reduced.

Compounds of the disclosure having formula I can exist in different isomeric forms. As used herein, the terms cis or trans are used in their conventional sense in the chemical arts, i.e., referring to the position of the substituents to one another relative to a reference plane, e.g., a double bond, or a ring system, such as a decalin-type ring system or a hydroquinolone ring system: in the cis isomer, the substituents are on the same side of the reference plane, in the trans isomer the substituents are on opposite sides. Additionally, different conformers are contemplated by the present disclosure, as well as distinct rotamers. Conformers are conformational isomers that can differ by rotations about one or more a bonds. Rotamers are conformers that differ by rotation about only a single a bond.

Compounds

The present disclosure provides compounds that modulate the activity of CCR(9). Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

For example, compounds of this disclosure act as potent CCR(9) antagonists, and this antagonistic activity has been further confirmed in animal testing for inflammation, one of the hallmark disease states for CCR(9). Accordingly, the compounds provided herein are useful in pharmaceutical compositions, methods for the treatment of CCR(9)-mediated diseases, and as controls in assays for the identification of competitive CCR(9) antagonists.

Provided herein are compounds of formula (I):

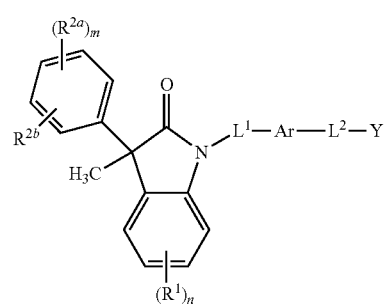

(I)

or a pharmaceutically acceptable salt thereof, wherein

Ar is a 5- to 10-membered aromatic or heteroaromatic ring, optionally substituted with from one to three $R^3$;

$L^1$ is selected from the group consisting of a bond, $C_{1-6}$ alkylene, and $C_{1-6}$ heteroalkylene, $L^2$ is selected from the group consisting of a bond, $C_{1-6}$ alkylene, and $C_{1-6}$ heteroalkylene, Y is $CO_2H$ or a carboxylic acid bioisostere;

each $R^1$ and each $R^{2a}$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl, wherein the alkyl, cycloalkyl and alkenyl portions are optionally substituted with from one to three members selected from fluoro, OH, CN, $C_{1-3}$ alkyl, $C_{1-3}$ haloalkyl, and $C_{1-3}$ alkoxy;

$R^{2b}$ is selected from the group consisting of H, halogen, cyano, $C_{1-6}$ alkyl, $C_{1-6}$ alkoxy, $C_{3-6}$ cycloalkyl, and $C_{2-6}$ alkenyl, wherein the alkyl, cycloalkyl and alkenyl portions are optionally substituted with from one to three members selected from fluoro, CN, $C_{1-3}$ alkyl, $C_{1-3}$ haloalkyl, and $C_{1-3}$ alkoxy;

or optionally one $R^{2a}$ and $R^{2b}$ when on adjacent vertices of a phenyl ring, may be joined together to form a 5- or 6-membered heterocycloalkyl ring having one or two ring vertices independently selected from O, N and S, wherein said heterocycloalkyl ring is optionally substituted with from one to three members selected from fluoro and $C_{1-3}$ alkyl;

each $R^3$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl;

the subscript m is an integer of from 0 to 4; and the subscript n is an integer of from 0 to 3.

In some embodiments, Y is selected from the group consisting of:

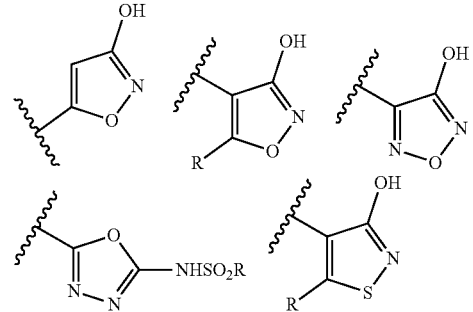

-continued

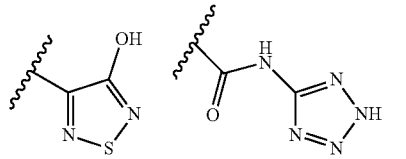
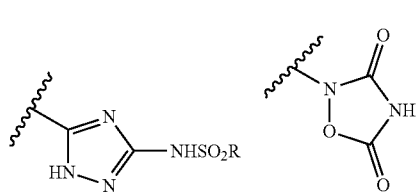
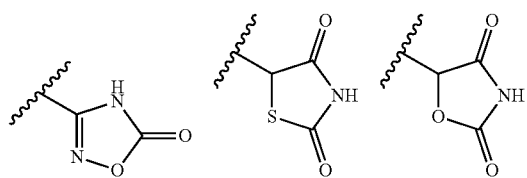
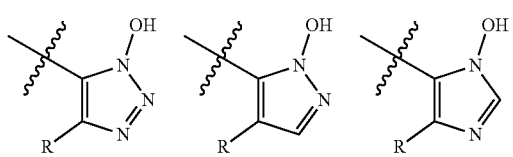
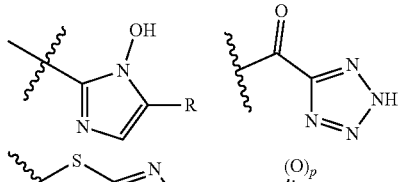
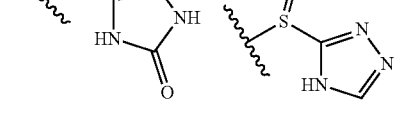
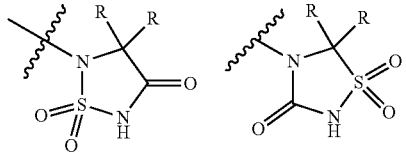
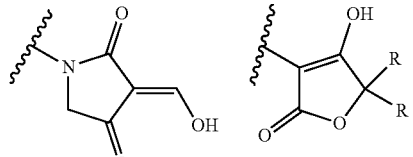
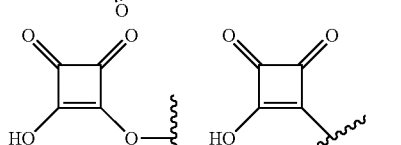
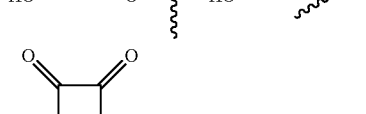
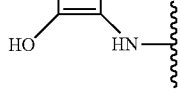

tetrazolyl and tetrazolonyl, wherein the tetrazolyl or tetrazolonyl is optionally substituted with R, wherein p is 0, 1 or 2 and wherein each R group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, or $C_1$-$C_4$ alkyl-O—$C_1$-$C_4$ alkyl.

In some embodiments, Y is selected from the group consisting of: tetrazolyl and tetrazolonyl, wherein the tetrazolyl or tetrazolonyl is optionally substituted with $C_{1-6}$ alkyl, $C_{1-6}$ haloalkyl, $C_{1-6}$ hydroxyalkyl, —$C_{1-6}$ alkoxy or $C_{1-4}$alkyl-O—$C_{1-4}$alkyl.

In some embodiments, a compound is provided having the formula selected from the group consisting of:

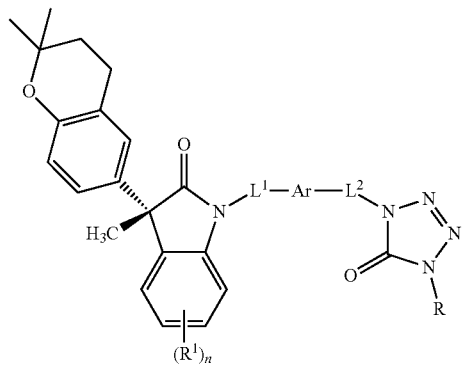

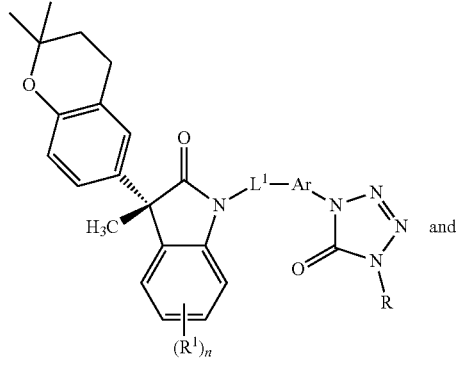

and

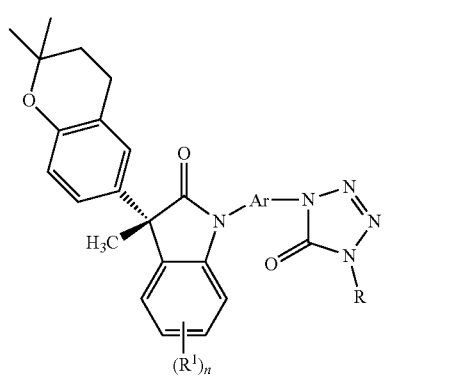

or a pharmaceutically acceptable salt thereof, wherein said compound is substantially free of other isomers.

In some embodiments, a compound is provided having the formula:

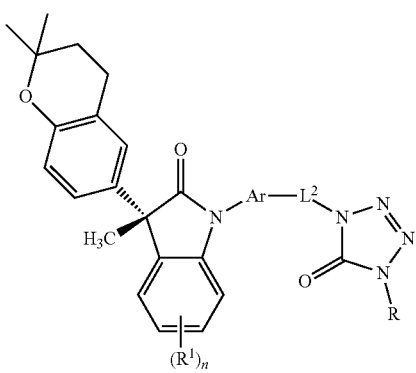

or a pharmaceutically acceptable salt thereof, wherein $L^2$ is $C_{1-3}$ alkylene and wherein said compound is substantially free of other isomers.

In some embodiments, a compound is provided having the formula (I'):

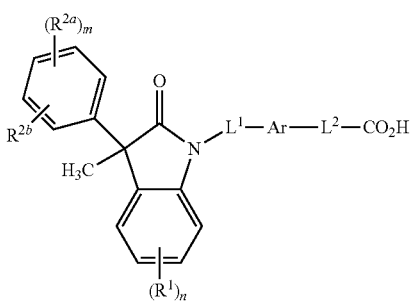

or a pharmaceutically acceptable salt thereof, wherein
Ar is a 5- to 10-membered aromatic or heteroaromatic ring, optionally substituted with from one to three $R^3$;
$L^1$ is selected from the group consisting of a bond, $C_{1-6}$ alkylene, and $C_{1-6}$ heteroalkylene,
$L^2$ is selected from the group consisting of a bond, $C_{1-6}$ alkylene, and $C_{1-6}$ heteroalkylene,
each $R^1$ and each $R^{2a}$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl, wherein the alkyl, cycloalkyl and alkenyl portion are optionally substituted with from one to three members selected from fluoro, CN, $C_{1-3}$ alkyl, $C_{1-3}$ haloalkyl, and $C_{1-3}$ alkoxy;
$R^{2b}$ is selected from the group consisting of H, halogen, cyano, $C_{1-6}$ alkyl, $C_{1-6}$ alkoxy, $C_{3-6}$ cycloalkyl, and $C_{2-6}$ alkenyl, wherein the alkyl, cycloalkyl and alkenyl portion are optionally substituted with from one to three members selected from fluoro, CN, $C_{1-3}$ alkyl, $C_{1-3}$ haloalkyl, and $C_{1-3}$ alkoxy;
or optionally one $R^{2a}$ and $R^{2b}$ when on adjacent vertices of a phenyl ring, may be joined together to form a 5- or 6-membered cycloheteroalkyl ring having one or two ring vertices independently selected from O, N and S, wherein said cycloheteroalkyl ring is optionally substituted with from one to three members selected from fluoro and $C_{1-3}$ alkyl;
each $R^3$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl;

the subscript m is an integer of from 0 to 4; and
the subscript n is an integer of from 0 to 3.

In one group of embodiments for each of formulae (I) and (I'), Ar is selected from benzene, pyridine and quinoline, each of which is optionally substituted with from one to two $R^3$.

In some selected embodiments of formula (I) and (I'), $L^1$ is selected from the group consisting of a bond, —CH$_2$— and —CH(CH$_3$)—. In other selected embodiments of formula (I), $L^2$ is selected from the group consisting of a bond, —O—CH$_2$—, —CH(CH$_3$)—, —C(CH$_3$)$_2$—, —CH$_2$CH$_2$—, —CH$_2$—, and —CH$_2$CH$_2$CH$_2$—.

In some selected embodiments of formula (I) and (I'), n is 1 or 2. In other selected embodiments of formula (I) and (I'), m is 1, 2 or 3.

In other embodiments, suitable compounds are provided having the formula (Ia):

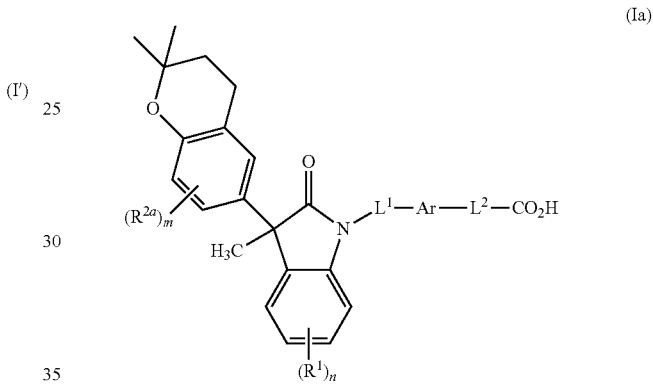

or a pharmaceutically acceptable salt thereof.

In one group of selected embodiments, Ar is selected from benzene, pyridine and quinoline, each of which is optionally substituted with from one to two $R^3$.

In another group of selected embodiments, L' is selected from the group consisting of a bond, —CH$_2$— and —CH(CH$_3$)—. In still another group of selected embodiments $L^2$ is selected from the group consisting of a bond, —O—CH$_2$—, —CH(CH$_3$)—, —C(CH$_3$)$_2$—, —CH$_2$CH$_2$—, —CH$_2$—, and —CH$_2$CH$_2$CH$_2$—.

In other selected embodiments, suitable compounds are selected from:

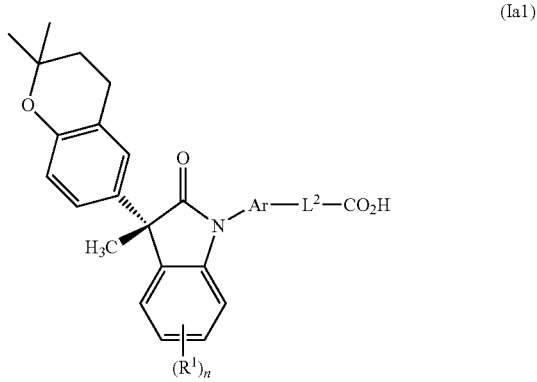

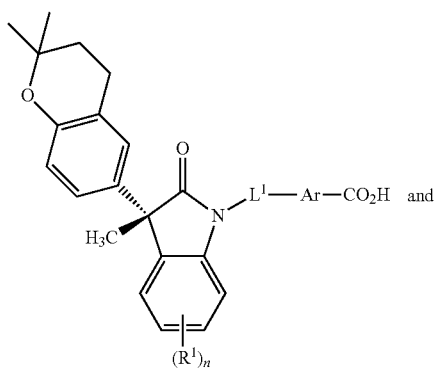

(Ia2)

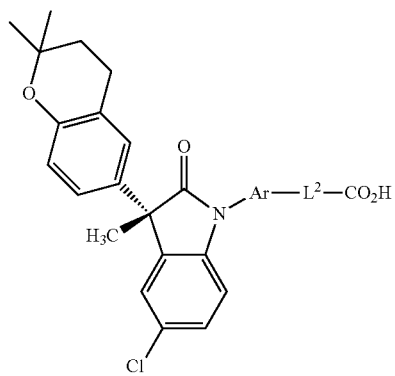

(Ia1')

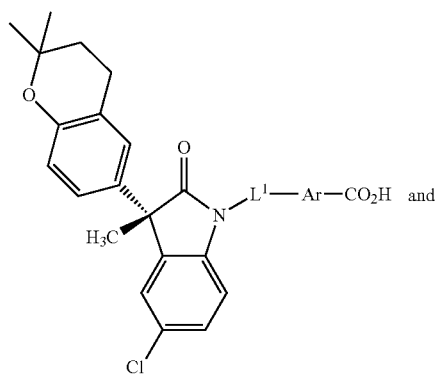

(Ia2')

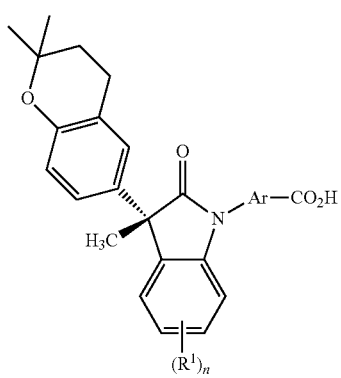

(Ia3)

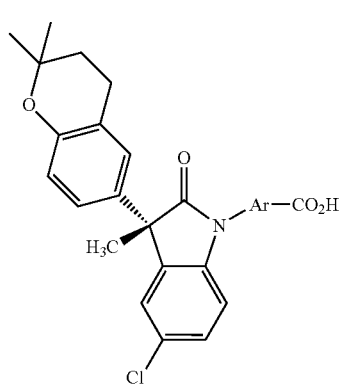

(Ia3')

or a pharmaceutically acceptable salt thereof, wherein said compound is substantially free of other isomers.

Within formula (Ia1), (Ia2) and (Ia3), selected embodiments are those wherein Ar is selected from the group consisting of benzene, pyridine and quinoline, each of which is optionally substituted with from one to two $R^3$. In still other embodiments, Ar is selected from the group consisting of 1,3-phenylene and 1,4-phenylene, each of which is optionally substituted with from one to two $R^3$. In some embodiments, referring to formulae (Ia1), (Ia2) and (Ia3), $L^1$ is selected from the group consisting of a bond, —CH$_2$— and —CH(CH$_3$)—. In other embodiments of formulae (Ia1), (Ia2) and (Ia3), $L^2$ is selected from the group consisting of —O—CH$_2$—, —CH(CH$_3$)—, —C(CH$_3$)$_2$—, —CH$_2$CH$_2$—, —CH$_2$— and —CH$_2$CH$_2$CH$_2$—. In still other embodiments of formulae (Ia1), (Ia2) and (Ia3), $R^1$ is selected from the group consisting of halogen, cyano, $C_{1-3}$ alkyl, $C_{1-3}$ alkoxy, $C_{1-3}$ haloalkyl, $C_{1-3}$ haloalkoxy, $C_{3-5}$ cycloalkyl, and $C_{2-3}$ alkenyl. In yet other embodiments of formulae (Ia1), (Ia2) and (Ia3), $R^1$ is selected from the group consisting of chloro, methyl, cyano, ethyl, cyclopropyl, trifluoromethyl and trifluoromethoxy.

In other selected embodiments, suitable compounds are selected from:

or a pharmaceutically acceptable salt thereof, wherein said compound is substantially free of other isomers.

In other embodiments, suitable compounds are provided having the formula (Ib):

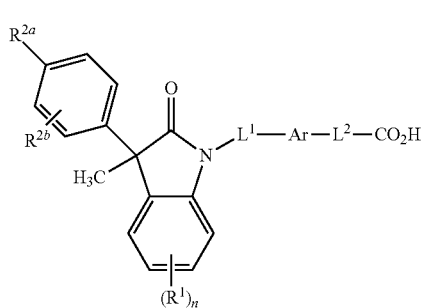

(Ib)

or a pharmaceutically acceptable salt thereof.

In some embodiments of formula (Ib), $R^{2b}$ is hydrogen. In other embodiments of formula (Ib), Ar is selected from the group consisting of benzene, pyridine and quinoline, each of which is optionally substituted with from one to two $R^3$. In still other embodiments of formula (Ib), $L^1$ is selected from the group consisting of a bond, —$CH_2$— and —CH($CH_3$)—. In yet other embodiments of formula (Ib), $L^2$ is selected from the group consisting of a bond, —O—$CH_2$—, —CH($CH_3$)—, —C($CH_3$)$_2$—, —$CH_2CH_2$—, —$CH_2$— and —$CH_2CH_2CH_2$—.

In other selected embodiments, suitable compounds are selected from:

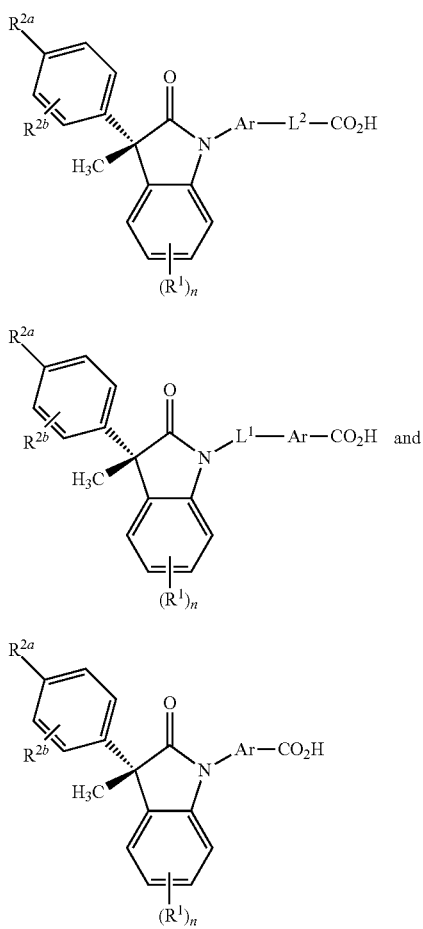

(Ib1)

(Ib2)

(Ib3)

or a pharmaceutically acceptable salt thereof, wherein said compound is substantially free of other isomers.

Within formula (Ib1), (Ib2) and (Ib3), selected embodiments are those wherein Ar is selected from the group consisting of benzene, pyridine and quinoline, each of which is optionally substituted with from one to two $R^3$. In some embodiments, referring to formulae (Ib1), (Ib2) and (Ib3), Ar is selected from the group consisting of 1,3-phenylene and 1,4-phenylene, each of which is optionally substituted with from one to two $R^3$. In other embodiments of formulae (Ib1), (Ib2) and (Ib3), $R^3$ is selected from the group consisting of $CH_3$, $CH_2CH_3$, $CH_2CH_2CH_3$, CH($CH_3$)$_2$ and $CH_2OH$. In still other embodiments of formulae (Ib1), (Ib2) and (Ib3), $L^1$ is selected from the group consisting of a bond, —$CH_2$— and —CH($CH_3$)—. In yet other embodiments of formulae (Ib1), (Ib2) and (Ib3), $L^2$ is selected from the group consisting of —O—$CH_2$—, —CH($CH_3$)—, —C($CH_3$)$_2$—, —$CH_2CH_2$—, —$CH_2$— and —$CH_2CH_2CH_2$—. In other embodiments of formulae (Ib1), (Ib2) and (Ib3), $R^3$ is selected from the group consisting of halogen, cyano, $C_{1-3}$ alkyl, $C_{1-3}$ alkoxy, $C_{1-3}$ haloalkoxy, $C_{3-5}$ cycloalkyl, and $C_{2-3}$ alkenyl, or $R^1$ is selected from the group consisting of chloro, methyl, cyano, ethyl, cyclopropyl, trifluoromethyl and trifluoromethoxy.

In other selected embodiments, suitable compounds are selected from:

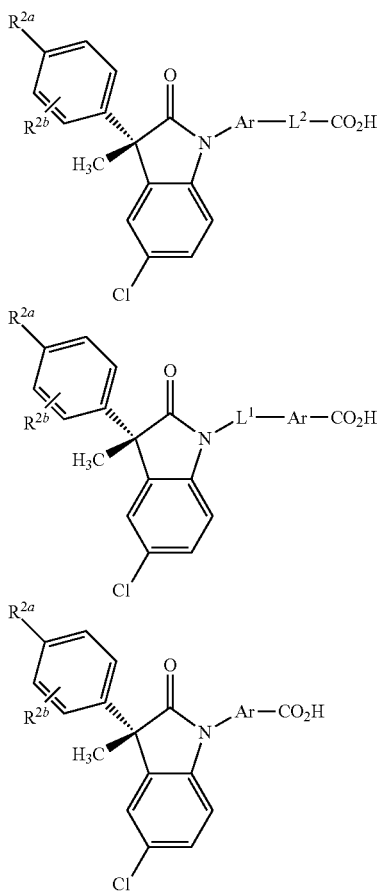

(Ib1') (Ib2') and (Ib3')

or a pharmaceutically acceptable salt thereof, wherein said compound is substantially free of other isomers.

Preparation of Compounds

Compound provided herein can be prepared by the general scheme below. Beginning with a suitably substituted phenylacetic acid ester, reaction with a substituted halonitrobenzene in the presence of base, following by methyl iodide sets the framework for 2-oxoindole ring construction having the quaternary center alpha to the carboxylic acid. Resolution of the isomers, followed by reduction of the nitro group and cyclization produces a substituted 2-oxoindole. Reaction at the indole nitrogen atom to attach either a substituted Ar group, or a linker ($L^1$), having an attached substituted Ar group will lead to the target compounds shown. One of skill in the art will appreciate that modifications can be made following the general guidance of the scheme below to provide a variety of compounds of formula (I).

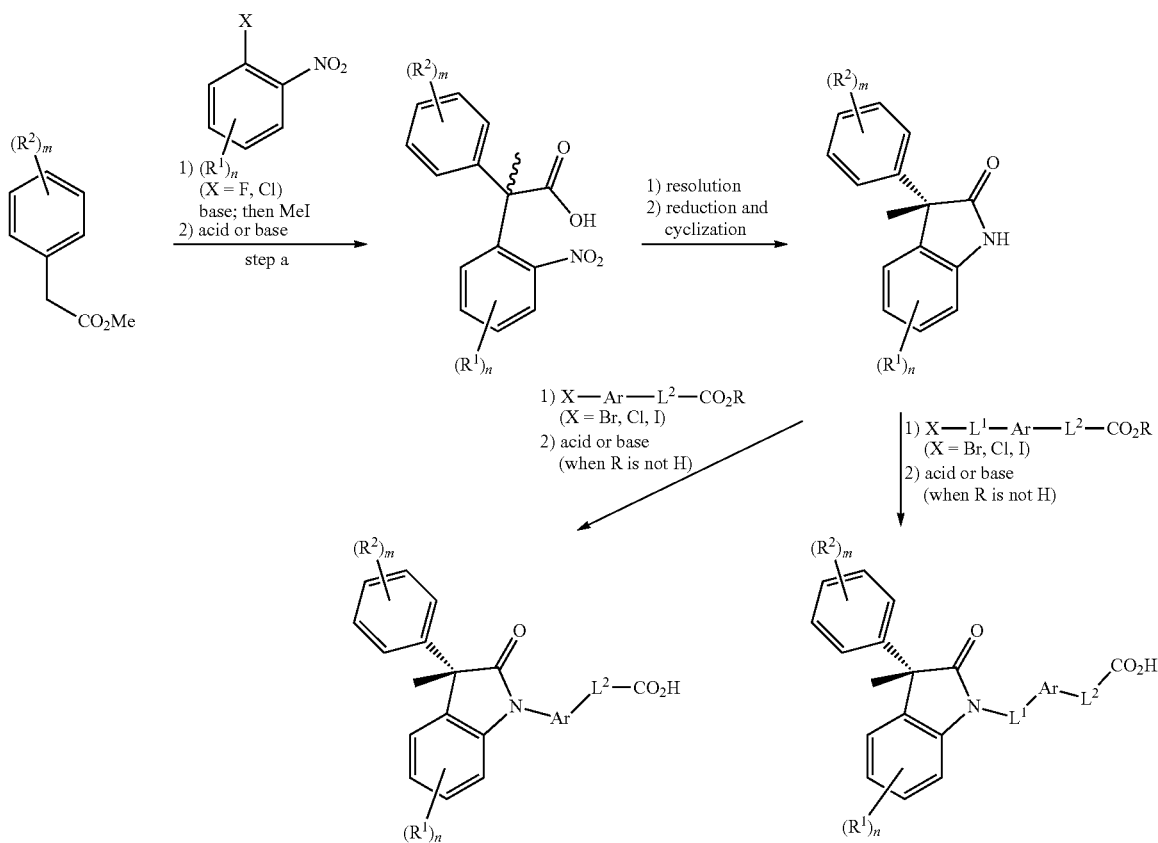

Compositions That Modulate Chemokine Activity

In another aspect, the present disclosure provides compositions that modulate chemokine activity, specifically CCR(9) activity. Generally, the compositions for modulating chemokine receptor activity in humans and animals will comprise a pharmaceutically acceptable excipient or diluent and a compound having any of the formulae I, I', Ia, Ib, Ia1, Ia2, Ia3, Ia1', Ia2', Ia3', Ib1, Ib2, Ib3, Ib1', Ib2' and Ib3'.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this disclosure may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Pat. No. 6,451,339, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil in water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present disclosure are employed. As used herein, topical application is also meant to include the use of mouth washes and gargles.

The pharmaceutical compositions and methods of the present disclosure may further comprise other therapeutically active compounds as noted herein, such as those applied in the treatment of the above mentioned pathological conditions.

In one embodiment, the present disclosure provides a composition consisting of a pharmaceutically acceptable carrier and a compound of the disclosure.

Methods of Treatment

Depending on the disease to be treated and the subject's condition, the compounds and compositions of the present disclosure may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present disclosure also contemplates administration of the compounds and compositions of the present disclosure in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In some embodiments, compounds of the present disclosure are administered as part of a combination therapy. For instance an amount of a chemotherapeutic agent or radiation is administered to the subject prior to, subsequent to or in combination with the compounds of the present disclosure. In some embodiments, the amount is sub-therapeutic when the chemotherapeutic agent or radiation is administered alone. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current disclosure may be administered prior to or subsequent to a second therapeutic regimen, for instance prior to or subsequent to a dose of chemotherapy or irradiation.

In still other embodiments, the present methods are directed to the treatment of allergic diseases, wherein a compound or composition of the disclosure is administered either alone or in combination with a second therapeutic agent, wherein said second therapeutic agent is an antihistamine or an anti-inflammatory. When used in combination, the practitioner can administer a combination of the compound or composition of the present disclosure and a second therapeutic agent. Also, the compound or composition and the second therapeutic agent can be administered sequentially, in any order.

The compounds and compositions of the present disclosure can be combined with other compounds and compositions having related utilities to prevent and treat the condition or disease of interest, such as inflammatory conditions and diseases, including inflammatory bowel disease (including Crohn's disease and ulcerative colitis), allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

In treating, preventing, ameliorating, controlling or reducing the risk of inflammation, the compounds of the present disclosure may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, aminosalicylates, corticosteroids and other immunosuppressive drugs, a non-steroidal antiinflammatory agent, or a cytokine-suppressing antiinflammatory agent, for example with a compound such as acetaminophen, aspirin, codeine, biological TNF sequestrants, biological agents which target $\alpha 4\beta 7$, ACE2 inhibitors, protein linase C inhibitors, fentanyl, ibuprofen, indomethacin, ketorolac, morphine, naproxen, phenacetin, piroxicam, a steroidal analgesic, sufentanyl, sunlindac, tenidap, and the like.

Similarly, the compounds of the present disclosure may be administered with a pain reliever; a potentiator such as caffeine, an H2-antagonist, simethicone, aluminum or magnesium hydroxide; a decongestant such as pseudophedrine; an antitussive such as codeine; a diuretic; a sedating or non-sedating antihistamine; a very late antigen (VLA-4) antagonist; an immunosuppressant such as cyclosporin, tacrolimus, rapamycin, EDG receptor agonists, or other FK-506 type immunosuppressants; a steroid; a non-steroidal anti-asthmatic agent such as a $\beta$2-agonist, leukotriene antagonist, or leukotriene biosynthesis inhibitor; an inhibitor of phosphodiesterase type IV (PDE-IV); a cholesterol lowering agent such as a HMG-CoA reductase inhibitor, sequestrant, or cholesterol absorption inhibitor; and an anti-diabetic agent such as insulin, $\alpha$-glucosidase inhibitors or glitazones.

The weight ratio of the compound of the present disclosure to the second active ingredient may be varied and will depend upon the effective dose of each ingredient. Generally, an effective dose of each will be used. Thus, for example, when a compound of the present disclosure is combined with an NSAID the weight ratio of the compound of the present disclosure to the NSAID will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

Methods of Treating or Preventing CCR(9)-Mediated Conditions or Diseases

In yet another aspect, the present disclosure provides methods of treating or preventing a CCR(9)-mediated condition or disease by administering to a subject having such a condition or disease a therapeutically effective amount of any compound of formula I, I', Ia, Ib, Ia1, Ia2, Ia3, Ia1', Ia2', Ia3', Ib1, Ib2, Ib3, Ib1 Ib2' or Ib3'. Compounds for use in the present methods include those compounds according to the formula I, I', Ia, Ib, Ia1, Ia2, Ia3, Ia1', Ia2', Ia3', Ib1, Ib2, Ib3, Ib1', Ib2' and Ib3', those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR(9)-mediated condition or disease" and related phrases and terms refer to a condition or disease characterized by inappropriate, i.e., less than or greater than normal, CCR(9) functional activity. Inappropriate CCR(9) functional activity might arise as the result of CCR(9) expression in cells which normally do not express CCR(9), increased CCR(9) expression (leading to, e.g., inflammatory and immunoregulatory disorders and diseases) or decreased CCR(9) expression. Inappropriate CCR(9) functional activity might also arise as the result of TECK secretion by cells which normally do not secrete TECK, increased TECK expression (leading to, e.g., inflammatory and immunoregulatory disorders and diseases) or decreased TECK expression. A CCR(9)-mediated condition or disease may be completely or partially mediated by inappropriate CCR(9) functional activity. However, a CCR(9)-mediated condition or disease is one in which modulation of CCR(9) results in some effect on the underlying condition or disease (e.g., a CCR(9) antagonist results in some improvement in patient well-being in at least some patients).

The term "therapeutically effective amount" means the amount of the subject compound that will elicit the biological or medical response of a cell, tissue, system, or animal, such as a human, that is being sought by the researcher, veterinarian, medical doctor or other treatment provider.

Diseases and conditions associated with inflammation, immune disorders, infection and cancer may be treated or prevented with the present compounds, compositions, and methods. In one group of embodiments, diseases or conditions, including chronic diseases, of humans or other species may be treated with inhibitors of CCR(9) function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, microscopic colitis, ileitis and enteritis, and postoperative ileus, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) immune mediated food allergies such as Coeliac (Celiac) disease (14) pulmonary fibrosis and other fibrotic diseases, (15) irritable bowel syndrome, (16) primary sclerosing cholangitis, (17) cancer (including both primary and metastatic), (18) bacterial associated syndromes such as hemorrhagic colitis and hemolytic uremic syndrome (19) melanoma, (20) primary sclerosing cholangitis, (21) post-operative ileus (22) hepatitis and inflammatory hepatic diseases (23) Sjogren syndrome.

In another group of embodiments, diseases or conditions may be treated with modulators and agonists of CCR(9) function. Examples of diseases that may be treated by modulating CCR(9) function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is means to include bone marrow transplant conditions and solid organ (e.g., kidney, liver, lung, heart, pancreas or combination thereof) transplant conditions.

Preferably, the present methods are directed to the treatment of diseases or conditions selected from inflammatory bowel disease including Crohn's disease and Ulcerative Colitis, allergic diseases, psoriasis, atopic dermatitis and asthma, autoimmune disease such as rheumatoid arthritis and immune-mediated food allergies such as Celiac disease.

In yet other embodiments, the present methods are directed to the treatment of psoriasis where a compound or composition of the disclosure is used alone or in combination with a second therapeutic agent such as a corticosteroid, a lubricant, a keratolytic agent, a vitamin D3 derivative, PUVA and anthralin.

In other embodiments, the present methods are directed to the treatment of atopic dermatitis using a compound or composition of the disclosure either alone or in combination with a second therapeutic agent such as a lubricant and a corticosteroid.

In further embodiments, the present methods are directed to the treatment of asthma using a compound or composition of the disclosure either alone or in combination with a second therapeutic agent such as a β2-agonist and a corticosteroid.

Kits and Packages

The terms "kit" and "pharmaceutical kit" refer to a commercial kit or package comprising, in one or more suitable containers, one or more pharmaceutical compositions and instructions for their use. In one embodiment, kits comprising a compound of Formula I, I', Ia, Ib, Ia1, Ia2, Ia3, Ia1', Ia2', Ia3', Ib1, Ib2, Ib3, Ib1', Ib2' or Ib3', or a pharmaceutically acceptable salt thereof, and instructions for its administration are provided. In one embodiment, kits comprising a compound of Formula I, I', Ia, Ib, Ia1, Ia2, Ia3, Ia1', Ia2', Ia3', Ib1, Ib2, Ib3, Ib1', Ib2' or Ib3', or a pharmaceutically acceptable salt thereof, in combination with one or more (e.g., one, two, three, one or two, or one to three) additional therapeutic agents and instructions for their administration are provided.

In one embodiment, the compounds of this disclosure are formulated into administration units which are packaged in a single packaging. The single packaging encompasses but is not limited to a bottle, a child-resistant bottle, an ampoule, and a tube. In one embodiment, the compounds of this disclosure and optionally additional therapeutic agents, are formulated into administration units and every single administration unit is individually packaged in a single packaging. Such individually packaged units may contain the pharmaceutical composition in any form including but not limited to liquid form, solid form, powder form, granulate form, an effervescent powder or tablet, hard or soft capsules, emulsions, suspensions, syrup, suppositories, tablet, troches, lozenges, solution, buccal patch, thin film, oral gel, chewable tablet, chewing gum, and single-use syringes. Such individually packaged units may be combined in a package made of one or more of paper, cardboard, paperboard, metal foil and plastic foil, for example a blister pack. One or more administration units may be administered once or several times a day. One or more administration units may be administered three times a day. One or more administration units may be administered twice a day. One or more administration units may be administered on a first day and one or more administration units may be administered on the following days.

Additional Combination Therapies

The compounds of this disclosure can be supplied alone or in conjunction with one or more other drugs. Examples of therapeutic agents that may be combined with a compound or composition of the present disclosure, either administered separately or in the same pharmaceutical composition, include, but are not limited to: modulators of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CX3CR1, ChemR23, C5aR, C5a, and C5, or any combination thereof. In some embodiments, the modulator is an antagonist.

Examples of therapeutic agents that may be combined with a compound or composition of the present disclosure, either administered separately or in the same pharmaceutical composition, include, but are not limited to: CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, CCX168, CCX168-M1, brazikumab, budesonide, ustekinumab, everolimus, glatiramer acetate, natalizumab, etanercept, mycophenolate mofetil, brodalumab, cannabidiol, foralumab, tralokinumab, tamibarotene, mesalazine, golimumab, teduglutide, infliximab, ropivacaine, filgotinib, etrolizumab, SHP-647, elafibranor, ABC-294640, ocrelizumab, tofacitinib, certolizumab pegol, adalimumab, sargramostim, abatacept, clarithromycin, GSK-2982772, upadacitinib, edasalonexent, secukinumab, vancomycin, vedolizumab, thalidomide, rituximab, catridecacog, RBX-2660, Ampion, nitazoxanide, fingolimod, tocilizumab, rosiptor acetate, AST-120, risankizumab, telotristat etiprate, lenalidomide, alicaforsen, tosufloxacin, interferon beta-1a, E-6011, KAG-308, dexamethasone sodium phosphate, ozanimod, dociparstat cobitolimod, mesalazine, PUR-0110, apremilast, mesalazine, valganciclovir, tacrolimus, mongersen, remestemcel-L, GS-5745, E-6011, E-6007, carotegrast methyl, piclidenoson, PF-06480605, balsalazide, pimecrolimus, mesalazine, recombinant interferon beta-1a, naltrexone, adalimumab, amiselimod, brilacidin, basiliximab, etrasimod, LP-02, rosiglitazone, plecanatide, laquinimod, rifabutin+clarithromycin+clofazimine, infliximab, tildrakizumab, omega-3-carboxylic acids, TOP-1288, peficitinib, rifamycin, rifaximin, JNJ-64304500, ASP-3291, DLX-105, zileuton, 99mTc labelled annexin V-128, ALT-836, Biferonex, clotrimazole, givinostat, *Trichuris suis* ova, INV-103, K(D)PT, BI-655064, glepaglutide, LYC-30937 EC, TRX-318, LY-3074828, larazotide acetate, IBP-9414, clazakizumab, mesalazine, eclomethasone dipropionate, NN-8828, olokizumab, bertilimumab, midismase, KRP-203, prednisolone, PF-06687234, STNM-01, KHK-4083, FE-999301, DLX-105, VB-201, DNVX-078, rifaximin, *Clostridium butyricum* MIYAIRI 588, OPS-2071, sotrastaurin, abrilumab, QBECO, anakinra, FFP-104, GLPG-1205, dolcanatide, PDA-002, molgramostim, mesalazine, metronidazole, repurposed naltrexone, vatelizumab, zucapsaicin, ciclosporin, oprelvekin, prulifloxacin, recombinant human lactoferrin, Alequel, SAN-300, STP-206, GLPG-0974, P-28-GST, N-6022, TNF alpha kinoid, ETX-201, low molecular weight heparin, ETX-201, GED-0507-34-Levo, metenkefalin acetate+tridecactide acetate, HMPL-004, SB-012, TRK-170, beta-1,3/1,6-glucan, mesalamine+N-acetylcysteine, 99mTc-sulesomab, olsalazine, mesalazine *bacillus licheniformis*, balsalazide sodium, propionyl-L-carnitine, *Clostridium butyricum*, beclomethasone dipropionate, acemannan, and SPD-480, or any combination thereof.

Examples of therapeutic agents that may be combined with a compound or composition of the present disclosure, either administered separately or in the same pharmaceutical composition, include, but are not limited to: an IL-23 antagonist, a Glucocorticoid agonist, an IL-6 agonist, an IL-12 antagonist, a mTOR complex 1 inhibitor, a mTOR inhibitor, a cell adhesion molecule inhibitor, an Integrin alpha-4/beta-1 antagonist, a TNF antagonist, a TNF binding agent, a Type II TNF receptor modulator, an Inosine monophosphate dehydrogenase inhibitor, a PurH purine biosynthesis protein inhibitor, an Interleukin receptor 17A, antagonist, a Cannabinoid CB1 receptor modulator, a Cannabinoid CB2 receptor modulator, a Cannabinoid receptor modulator, a CD3 antagonist, an IL-13 antagonist, a Retinoic acid receptor alpha agonist, a Retinoic acid receptor beta agonist, a Retinoid receptor agonist, a Cyclooxygenase inhibitor, a TNF alpha ligand inhibitor, a Glucagon-like peptide 2 agonist, a sodium channel inhibitor, a Jak1 tyrosine kinase inhibitor, an Integrin alpha-4/beta-7 antagonist, an Integrin alpha-E antagonist, an Integrin beta-7 antagonist, an Immunoglobulin G2 modulator, a MAdCAM inhibitor, an Insulin sensitizer, a PPAR alpha agonist, a PPAR delta agonist, a Collagen modulator, a Dihydroceramide delta 4 desaturase inhibitor, a Sphingosine kinase 1 inhibitor, a Sphingosine kinase 2 inhibitor, aB-lymphocyte antigen CD20 inhibitor, a JAK tyrosine kinase inhibitor, a Jak3 tyrosine kinase inhibitor, a CSF-1 agonist, a GM-CSF receptor agonist, a Cytotoxic T-lymphocyte protein-4 stimulator, a T cell surface glycoprotein CD28 inhibitor, a RIP-1 kinase inhibitor, a Nuclear factor kappa B inhibitor, an IL-17 antagonist, a Peptidoglycan recognition protein inhibitor, an Integrin alpha-4/beta-7 antagonist, a B-lymphocyte antigen CD20 inhibitor, a Factor XIII agonist, a Stem cell antigen-1 inhibitor, a Cannabinoid receptor antagonist; Sphingosine-1-phosphate receptor-1 modulator, an IL-6 antagonist, an IL-6 receptor modulator, a SH2 domain inositol phosphatase 1 stimulator, a Tryptophan 5-hydroxylase inhibitor, a ICAM1 gene inhibitor, a DNA gyrase inhibitor, a Topoisomerase IV inhibitor, an Interferon beta ligand, a Fractalkine ligand inhibitor, a EP4 prostanoid receptor agonist, a Sphingosine-1-phosphate receptor-1 agonist, a Sphingosine-1-phosphate receptor-1 modulator, a Sphingosine-1-phosphate receptor-5 modulator, a Cathepsin G inhibitor, a Complement cascade inhibitor, an Elastase inhibitor, a Heparin agonist, a L-Selectin antagonist, a P-Selectin antagonist, a Nuclear factor kappa B inhibitor, a TLR-9 agonist, an Interleukin-1 beta ligand modulator, a PDE 4 inhibitor, a DNA polymerase inhibitor, a SMAD-7 inhibitor, a TGF beta 1 ligand inhibitor, a Metalloprotease-9 inhibitor, a Fractalkine ligand inhibitor, an Integrin antagonist, an Adenosine A3 receptor agonist, a Tumor necrosis factor 15 ligand inhibitor, an IL-10 antagonist, an IL-2 antagonist, an IL-4 antagonist, an Interferon gamma receptor antagonist, an Interferon beta ligand, an Opioid receptor antagonist, an IL-2 receptor alpha subunit inhibitor, a Sphingosine 1 phosphate phosphatase 1 stimulator, an Insulin sensitizer, a PPAR gamma agonist, a Natriuretic peptide receptor C agonist, a n acyltransferase inhibitor, an apolipoprotein C3 antagonist, an adapter molecule crk inhibitor, an IL-8 antagonist, an Interleukin-1 beta ligand inhibitor, a Src tyrosine kinase inhibitor, a Syk tyrosine kinase inhibitor, a DNA RNA polymerase inhibitor, a RNA polymerase inhibitor, a Melanocortin agonist, a 5-Lipoxygenase inhibitor, a Tissue factor inhibitor, an Interferon beta ligand, a Bradykinin receptor modulator, an Histone deacetylase inhibitor, a P2×7 purinoceptor agonist, a mitochondrial 10 kDa heat shock protein stimulator, a CD40 ligand receptor antagonist, a Glucagon-like peptide 2 agonist, a FIFO ATP synthase modulator, a CD3 antagonist, a Zonulin inhibitor, a Cyclooxygenase inhibitor, a Lipoxygenase modulator, an IL-21 antagonist, a CCR3 chemokine antagonist, an Eotaxin ligand inhibitor, a Superoxide dismutase modulator, a Sphingosine-1-phosphate receptor-1 agonist, a CD29 modulator, an Interleukin-10 ligand, a CHST15 gene inhibitor, an OX40 ligand inhibitor, an IL-6 receptor modulator, a Nuclear factor kappa B inhibitor, an Oncostatin M receptor modulator, a STAT inhibitor, a STAT-3 inhibitor, a TLR-2 antagonist, a TLR-4 antagonist, a RNA polymerase inhibitor, a Protein kinase C alpha inhibitor, a Protein kinase C beta inhibitor, a Protein kinase C delta inhibitor, a Protein kinase C epsilon inhibitor, a Protein kinase C eta inhibitor, a Protein kinase C theta inhibitor, a Type I IL-1 receptor antagonist, a CD40 ligand inhibitor, a CD40 ligand receptor antagonist, a G-protein coupled receptor 84 antagonist, a Guanylate cyclase receptor agonist, a CD49b antagonist, a Vanilloid VR1 agonist, a Calcineurin inhibitor, an IL-11 agonist, a PDGF receptor agonist, a DNA gyrase inhibitor, a Lactoferrin stimulator, an Integrin alpha-1/beta-1 antagonist, a Free fatty acid receptor 2 antagonist, an Alcohol dehydrogenase 5 inhibitor, a glutathione reductase inhibitor, an Interferon gamma receptor antagonist, Low molecular weight heparin, a PPAR gamma agonist, a ACTH receptor agonist, an Adrenocorticotrophic hormone ligand, an Opioid growth factor receptor agonist, an IL-6 antagonist, an Interleukin-1 beta ligand modulator, a Nuclear factor kappa B inhibitor; a GATA 3 transcription factor inhibitor, a Nuclear factor kappa B inhibitor, an Oxidoreductase inhibitor, a Glucocorticoid agonist, an Interferon gamma receptor agonist, or any combination thereof.

EXAMPLES

The following examples are offered to illustrate, but not to limit the claimed disclosure.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5μ column for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the disclosure:

HPLC, High Pressure Liquid Chromatography; DMF, Dimethyl formamide; TFA, Trifluoroacetic Acid; THF, Tetrahydrofuran; EtOAc, Ethyl acetate; BOC$_2$O, di-tertbutyl dicarbonate or BOC anhydride; HPLC, High Pressure Liquid Chromatography; DIPEA, Diisopropyl ethylamine; HBTU, O-(benzotriazol-1-yl)-N,N,N',N'-tetramethyluronium hexafluorophosphate; dppf, 1,1'-Bis(diphenylphosphino)ferrocene; Pd$_2$(dba)$_3$, Tris(dibenzylideneacetone)dipalladium(0); DIPEA, diisopropylethylamine; DMP, dimethylphthalate; Me, methyl; Et, ethyl; DCM, dichloromethane.

Compounds within the scope of this disclosure can be synthesized as described below, using a variety of reactions known to the skilled artisan. One skilled in the art will also recognize that alternative methods may be employed to synthesize the target compounds of this disclosure, and that the approaches described within the body of this document are not exhaustive, but do provide broadly applicable and practical routes to compounds of interest.

Certain molecules disclosed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Synthesis of (3R)-5-chloro-3-(2,2-dimethylchroman-6-yl)-3-methyl-indolin-2-one

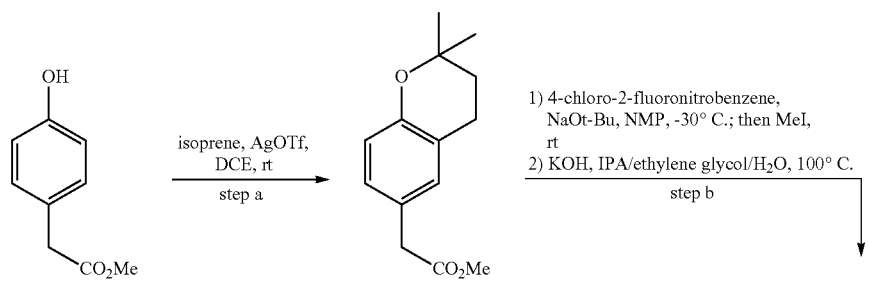

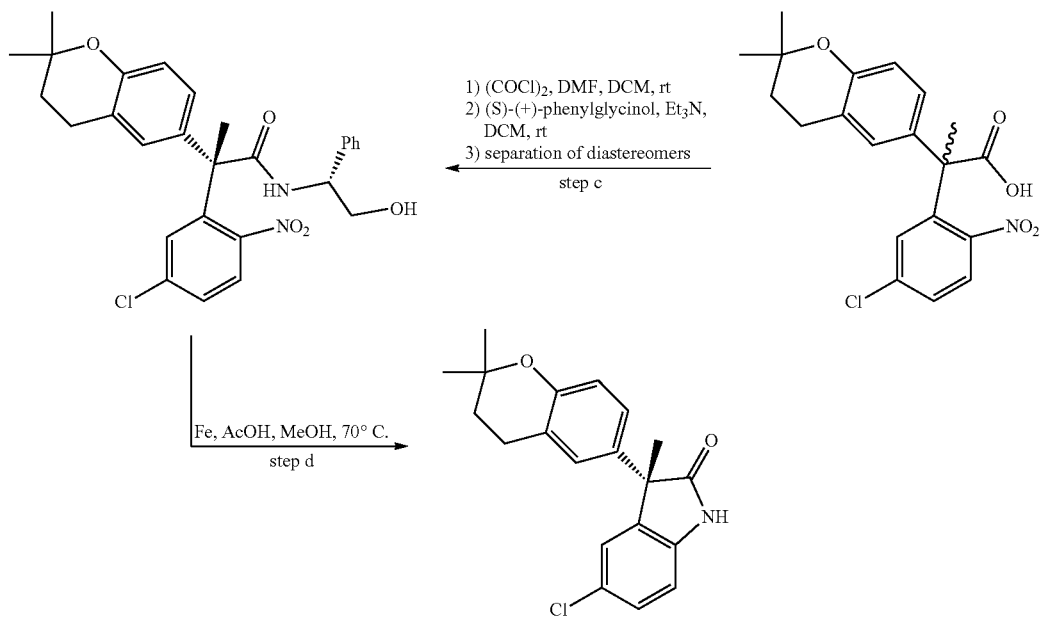

a) A solution of silver triflate (0.385 g, 1.50 mmol) in 1,2-dichloroethane (1.0 L) was heated at 90° C. for 3 h under a reflux condenser and nitrogen atmosphere. The cloudy mixture was cooled to room temperature before methyl 4-hydroxyphenylacetate (24.9 g, 150 mmol) was added. Isoprene (15.3 g, 225 mmol) in 1,2-dichloroethane (100 mL) was added dropwise over 10 min and the mixture was stirred at room temperature for 2 h. The solution was concentrated, diluted in EtOAc (150 mL), and washed with saturated aqueous $NaHCO_3$ (2×100 mL) and 1 M $NaHSO_4$ (2×100 mL). The organic layer was dried over $Na_2SO_4$, filtered, and concentrated in vacuo. Purification of the crude material by flash chromatography (1-10% EtOAc in hexanes) eluted methyl 2-(2,2-dimethylchroman-6-yl)acetate.

b) To a cooled (−30° C.) solution of sodium tert-butoxide (93.0 g, 963 mmol) in anhydrous N-methylpyrrolidone (500 mL) under nitrogen atmosphere was slowly added methyl 2-(2,2-dimethylchroman-6-yl)acetate (80.8 g, 344 mmol), followed by 4-chloro-2-fluoronitrobenzene (62.1 g, 354 mmol), and more N-methylpyrrolidone (150 mL). After stirring at −30° C. for 1 h, methyl iodide (42.8 mL, 688 mmol) was added by syringe and the mixture was stirred for an additional 20 min. The reaction was quenched by addition of 3 M HCl (600 mL) and the mixture was warmed to room temperature. The reaction mixture was extracted with methyl tert-butyl ether (1×500 mL), dried over $Na_2SO_4$, filtered through a plug of silica gel, and concentrated in vacuo to afford a brown solid. The crude material was diluted in a solution of isopropyl alcohol (520 mL), water (260 mL), and ethylene glycol (340 g) and then cooled to 0° C. Potassium hydroxide (130 g, 2.32 mol) was added and the solution was heated to 100° C. for 4 h. After the completion of the reaction, the mixture was cooled back to 0° C., acidified to pH 3 with aqueous 3 M HCl, and extracted with EtOAc (2×300 mL). The organic layers were dried over $Na_2SO_4$, filtered through a plug of silica gel, and concentrated in vacuo to obtain 2-(5-chloro-2-nitro-phenyl)-2-(2,2-dimethylchroman-6-yl)propionic acid.

c) Oxalyl chloride (2.10 mL, 24.0 mmol) and dimethylformamide (0.10 mL) were sequentially added to a stirred solution of 2-(5-chloro-2-nitro-phenyl)-2-(2,2-dimethylchroman-6-yl)propionic acid (7.21 g, 18.5 mmol) in dichloromethane (100 mL) at room temperature. After 1.5 h, the reaction mixture was concentrated and re-dissolved in dichloromethane (100 mL). Triethylamine (7.77 mL, 55.2 mmol) and (S)-(+)-phenylglycinol (2.54 g, 18.5 mmol) were added and the mixture was allowed to stir at room temperature until the reaction was complete (1 h). The mixture was concentrated, diluted in EtOAc (300 mL), and washed with aqueous 1 M HCl (1×200 mL). The organic layer was dried over $Na_2SO_4$, filtered, and concentrated in vacuo. Purification of the crude material by flash chromatography (1-8% THF in DCM) separated the diastereomers of 2-(5-chloro-2-nitro-phenyl)-2-(2,2-dimethylchroman-6-yl)-N-(2-hydroxy-1-phenyl-ethyl)propanamide. The second-eluting diastereomer was taken through subsequent transformations.

d) To a solution of 2-(5-chloro-2-nitro-phenyl)-2-(2,2-dimethylchroman-6-yl)-N-(2-hydroxy-1-phenyl-ethyl)propanamide (3.95 g, 7.76 mmol) and acetic acid (4 mL) in methanol (80 mL) was added iron powder (4.0 g, 71.7 mmol) and the reaction mixture was heated to 70° C. for 2 h. After cooling to room temperature, the mixture was diluted with EtOAc (150 mL) and washed with 1 M HCl (1×100 mL) and water (1×100 mL). The organic layer was dried over $Na_2SO_4$, filtered, and concentrated in vacuo. Purification of the crude material by flash chromatography (0-40% EtOAc in hexanes) gave (3R)-5-chloro-3-(2,2-dimethylchroman-6-yl)-3-methyl-indolin-2-one.

Example 2: Alternate synthesis of (3R)-5-chloro-3-(2,2-dimethylchroman-6-yl)-3-methyl-indolin-2-one

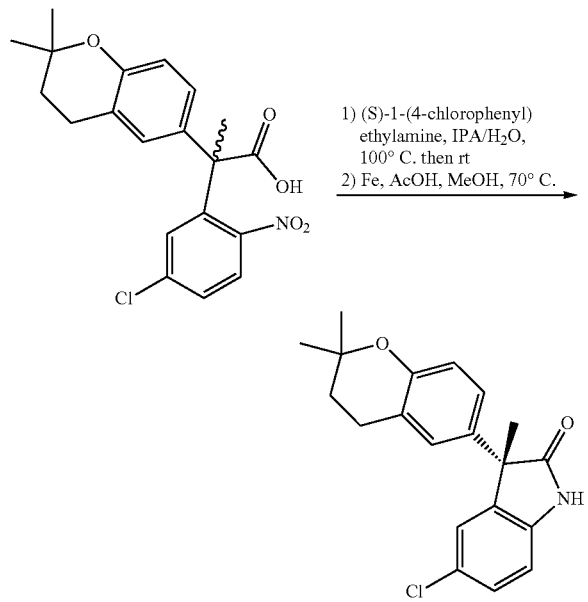

1) (S)-1-(4-chlorophenyl)ethylamine, IPA/H₂O, 100° C. then rt
2) Fe, AcOH, MeOH, 70° C.

A solution of 2-(5-chloro-2-nitro-phenyl)-2-(2,2-dimethylchroman-6-yl)propionic acid (37.3 g, 95.6 mmol) and (S)-1-(4-chlorophenyl)ethylamine in isopropyl alcohol (150 mL) and water (50 mL) was heated at 100° C. until all solids were dissolved. The solution was then allowed to gradually cool to room temperature and left to sit undisturbed overnight. The salt that came out of solution was filtered and washed with 2:1 IPA-H₂O (180 mL) to give a pure crystalline material (17.0 g, 33%, er>100:1 as the free from). A solution of crystalline (S)-1-(4-chlorophenyl)ethylamine salt of 2-(5-chloro-2-nitro-phenyl)-2-(2,2-dimethyl chroman-6-yl)propionic acid (546 mg, 1.0 mmol), iron powder (224 mg, 4.0 mmol), and acetic acid (480 mg, 8.0 mmol) in methanol (5.0 mL) was heated to 70° C. for 1 h. After cooling to room temperature, the mixture was diluted with EtOAc (50 mL) and washed with 1 M HCl (1×50 mL) and water (1×50 mL). The organic layer was dried over Na₂SO₄, filtered, and concentrated in vacuo. Purification by flash chromatography (0-40% EtOAc in hexanes) provided (3R)-5-chloro-3-(2,2-dimethylchroman-6-yl)-3-methyl-indolin-2-one.

Example 3: Synthesis of 3-[(3R)-5-chloro-3-(2,2-dimethylchroman-6-yl)-3-methyl-2-oxo-indolin-1-yl]benzoic acid

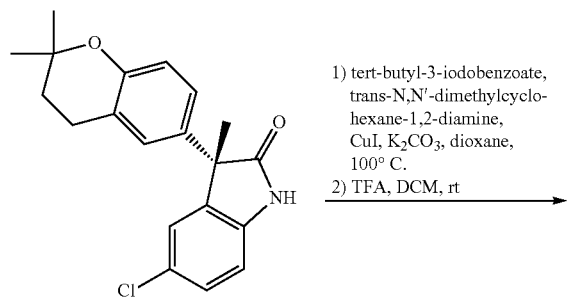

1) tert-butyl-3-iodobenzoate, trans-N,N'-dimethylcyclohexane-1,2-diamine, CuI, K₂CO₃, dioxane, 100° C.
2) TFA, DCM, rt

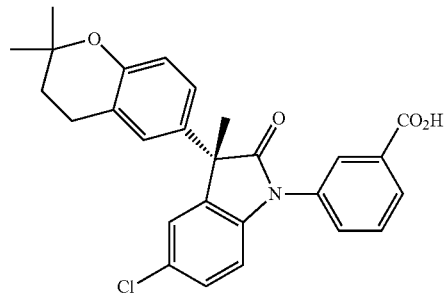

To a solution of (3R)-5-chloro-3-(2,2-dimethylchroman-6-yl)-3-methyl-indolin-2-one (45 mg, 0.13 mmol), tert-butyl-3-iodobenzoate (80 mg, 0.27 mmol), trans-N,N'-dimethylcyclohexane-1,2-diamine (10 mg, 0.07 mmol), and potassium carbonate (70 mg, 0.51 mmol) in dioxane (2.5 mL) was added copper iodide (10 mg, 0.053 mmol). The mixture was purged with nitrogen and heated to 100° C. After 1 h, the mixture was cooled to room temperature and diluted with EtOAc (20 mL). The organic layer was washed with 1 M HCl (1×20 mL), water (1×20 mL), dried over Na₂SO₄, filtered, and concentrated in vacuo. The crude material was diluted in dichloromethane (1 mL) and trifluoroacetic acid (2 mL) and stirred at room temperature for 5 h. The mixture was concentrated and purified by reverse-phase HPLC (C18 column, acetonitrile-H₂O with 0.1% TFA as eluent) to afford the titled compound. ¹H NMR (400 MHz, Chloroform-d) δ 8.22-8.09 (m, 2H), 7.69 (dddd, J=8.0, 1.8, 1.3, 0.4 Hz, 1H), 7.66-7.58 (m, 1H), 7.26-7.17 (m, 2H), 7.06 (d, J=2.3 Hz, 1H), 6.99 (ddd, J=8.5, 2.5, 0.6 Hz, 1H), 6.88-6.81 (m, 1H), 6.73 (d, J=8.6 Hz, 1H), 2.76 (t, J=6.7 Hz, 2H), 1.87 (s, 3H), 1.78 (t, J=6.7 Hz, 2H), 1.32 (d, J=1.5 Hz, 6H); MS: (ES) m/z calculated for $C_{27}H_{25}ClNO_4$ [M+H]⁺ 462.1, found 462.5.

Example 4: Synthesis of 4-[[(3R)-5-chloro-3-(2,2-dimethylchroman-6-yl)-3-methyl-2-oxo-indolin-1-yl]methyl]benzoic acid

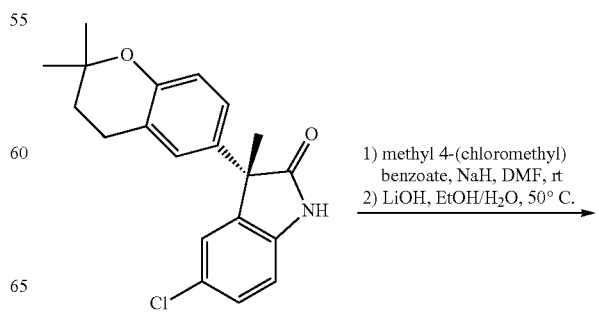

1) methyl 4-(chloromethyl)benzoate, NaH, DMF, rt
2) LiOH, EtOH/H₂O, 50° C.

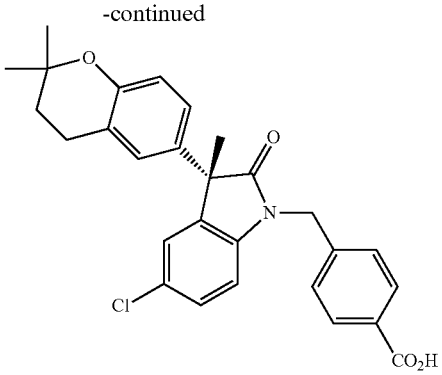

To a cooled (0° C.) solution of (3R)-5-chloro-3-(2,2-dimethylchroman-6-yl)-3-methyl-indolin-2-one (45 mg, 0.13 mmol) in anhydrous dimethylformamide (0.80 mL) under nitrogen was added sodium hydride (20 mg, 60% suspension in mineral oil, 0.50 mmol). After stirring at 0° C. for 10 min, the solution was allowed to warm to room temperature and methyl 4-(chloromethyl)benzoate (25 mg, 0.14 mmol) was added. The mixture was left to stir for 30 min at room temperature before the reaction was carefully quenched by the addition of 1 M HCl (25 mL) and extracted with EtOAc (50 mL). The organic layer was washed with water (1×20 mL), dried over $Na_2SO_4$, filtered, and concentrated in vacuo. The crude material was re-dissolved in a mixture of ethanol (2 mL) and water (1 mL). Lithium hydroxide monohydrate (100 mg, 2.4 mmol) was added and the mixture was stirred at 50° C. for 30 min. After cooling to room temperature, the reaction was quenched by the addition of 1 M HCl (25 mL) and extracted with EtOAc (50 mL). The organic layer was washed with water (1×20 mL), dried over $Na_2SO_4$, filtered, and concentrated in vacuo. Purification of the crude material by reverse-phase HPLC (C18 column, acetonitrile-$H_2O$ with 0.1% TFA as eluent) gave the titled compound. $^1$H NMR (400 MHz, Chloroform-d) δ 8.05 (d, J=8.2 Hz, 2H), 7.34 (d, J=8.1 Hz, 2H), 7.19-7.12 (m, 2H), 6.99 (d, J=2.4 Hz, 1H), 6.91 (dd, J=8.6, 2.5 Hz, 1H), 6.72 (d, J=8.5 Hz, 1H), 6.67-6.60 (m, 1H), 5.09-4.89 (m, 2H), 2.74 (t, J=6.8 Hz, 2H), 1.81 (s, 3H), 1.78 (t, J=6.7 Hz, 2H), 1.32 (s, 6H); MS: (ES) m/z calculated for $C_{28}H_{27}ClNO_4$ [M+H]$^+$ 476.1, found 476.2.

Example 5: Synthesis of 3-[(3R)-3-(4-tert-butylphenyl)-5-chloro-3-methyl-2-oxo-indolin-1-yl]benzoic acid

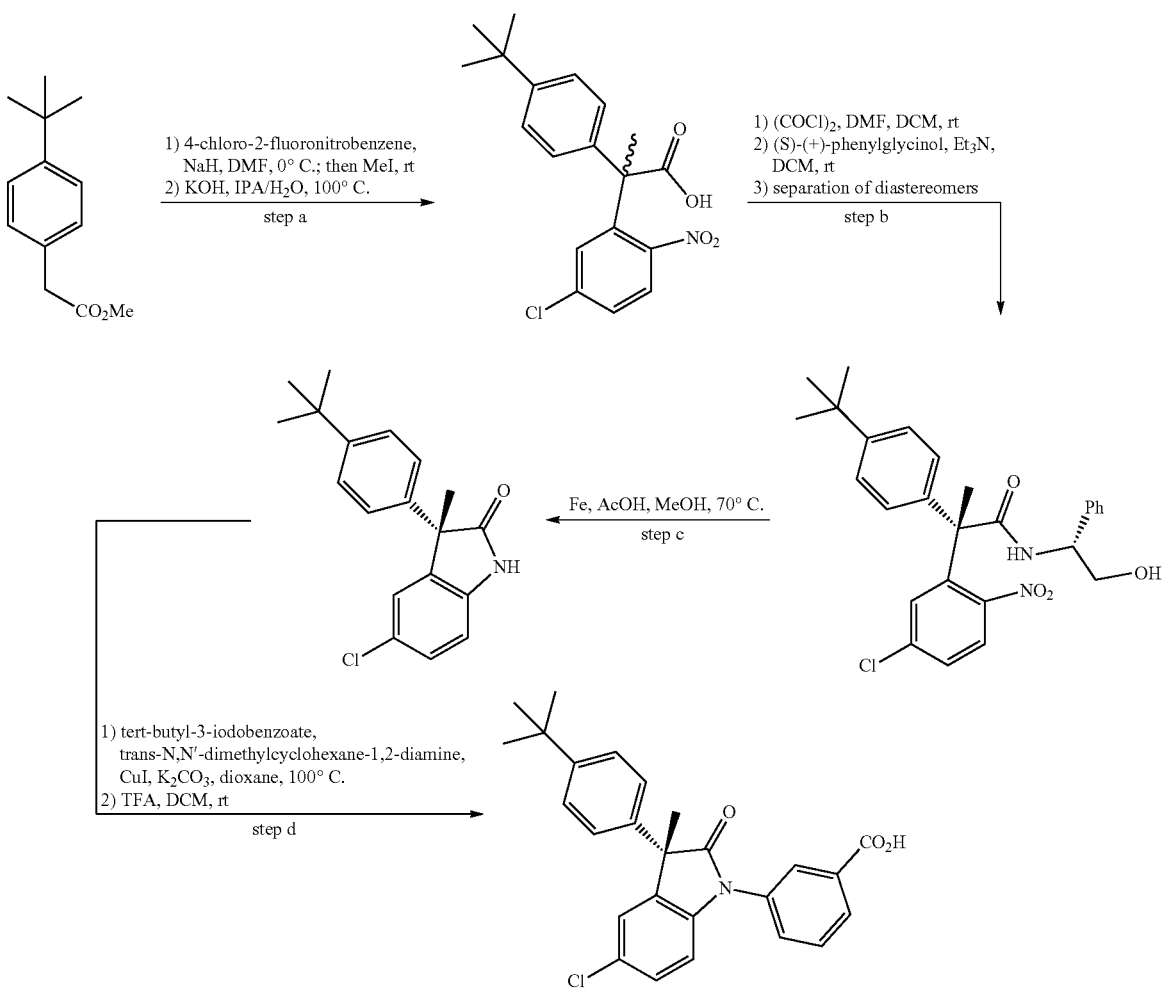 [SMILES: COC(=O)Cc1ccc(C(C)(C)C)cc1 ; CC(C)(C)c1ccc(C(C)(C(=O)O)c2cc(Cl)ccc2[N+](=O)[O-])cc1 ; CC(C)(C)c1ccc([C@]2(C)C(=O)Nc3ccc(Cl)cc32)cc1 ; CC(C)(C)c1ccc([C@](C)(C(=O)N[C@@H](CO)c2ccccc2)c2cc(Cl)ccc2[N+](=O)[O-])cc1 ; CC(C)(C)c1ccc([C@]2(C)C(=O)N(c3cccc(C(=O)O)c3)c3ccc(Cl)cc32)cc1]

a) To a cooled (0° C.) solution of sodium hydride (1.30 g, 39.9 mmol) in anhydrous dimethylformamide (5 mL) under nitrogen atmosphere was slowly added methyl p-tert-butylphenylacetate (1.70 g, 8.22 mmol) in dimethylformamide (5 mL) and the mixture was allowed to stir at 0° C. for 30 min. Next, 4-chloro-2-fluoronitrobenzene (1.60 g, 9.05 mmol) in dimethylformamide (3 mL) was added dropwise over 10 min. After 1.5 h of stirring at 0° C., methyl iodide (0.51 mL, 16.4 mmol) was added and the mixture was allowed to warm to room temperature and stir for an additional 3 h. The reaction was quenched by the addition of saturated aqueous NH$_4$Cl (50 mL). The mixture was extracted with EtOAc (2×50 mL) and the organic layers were dried over Na$_2$SO$_4$, filtered, and concentrated in vacuo. Purification by flash chromatography (0-20% EtOAc in hexanes) provided methyl 2-(4-tert-butylphenyl)-2-(3-chlorophenyl)propionate. The compound was dissolved in isopropyl alcohol (40 mL) and water (20 mL) with potassium hydroxide (2.3 g, 41.1 mmol) and the mixture was heated at 100° C. for 2 h. The mixture was cooled to room temperature, acidified to pH 3 with 1 M HCl, and extracted with EtOAc (2×50 mL). The combined organic layers were dried over Na$_2$SO$_4$, filtered, and concentrated in vacuo. Purification of the crude material by flash chromatography (0-30% EtOAc in hexanes) provided 2-(4-tert-butylphenyl)-2-(3-chlorophenyl)propionic acid.

b) Oxalyl chloride (0.57 mL, 6.6 mmol) and dimethylformamide (4 drops) were sequentially added to a stirred solution of 2-(4-tert-butylphenyl)-2-(3-chlorophenyl)propionic acid (2.11 g, 5.5 mmol) in dichloromethane (35 mL) at room temperature. After 2 h, the reaction mixture was concentrated and re-dissolved in dichloromethane (30 mL). Triethylamine (2.3 mL, 16.5 mmol) and (S)-(+)-phenylglycinol (750 mg, 5.5 mmol) were added and the mixture was allowed to stir at room temperature for 1 h. The mixture was concentrated, diluted in EtOAc (100 mL) and washed with aqueous 1 M HCl (1×50 mL). The organic layer was dried over Na$_2$SO$_4$, filtered, and concentrated in vacuo. Purification of the crude material by flash chromatography (1-15% EtOAc in DCM) separated the diastereomers of (2R)-2-(4-tert-butylphenyl)-2-(3-chlorophenyl)-N-[(1R)-2-hydroxy-1-phenyl-ethyl)]propanamide. The second-eluting diastereomer was taken through subsequent transformations.

c) To a solution of (2R)-2-(4-tert-butylphenyl)-2-(3-chlorophenyl)-N-[(1R)-2-hydroxy-1-phenyl-ethyl)]propanamide (250 mg, 0.52 mmol) and acetic acid (0.22 mL) in methanol (2.6 mL) was added iron powder (87 mg, 1.56 mmol) and the reaction mixture was heated to 70° C. for 2 h. After cooling to room temperature, the mixture was diluted with EtOAc (20 mL) and washed with 1 M HCl (1×10 mL) and water (1×10 mL). The organic layer was dried over Na$_2$SO$_4$, filtered, and concentrated in vacuo. Purification of the crude material by flash chromatography (0-40% EtOAc in hexanes) gave (3R)-3-(4-tert-butylphenyl)-5-chloro-3-methyl-indolin-2-one.

d) To a solution of (3R)-3-(4-tert-butylphenyl)-5-chloro-3-methyl-indolin-2-one (34 mg, 0.11 mmol), tert-butyl-3-iodobenzoate (65 mg, 0.22 mmol), trans-N,N'-dimethylcyclohexane-1,2-diamine (10 mg, 0.07 mmol), and potassium carbonate (70 mg, 0.51 mmol) in dioxane (2.5 mL) was added copper iodide (10 mg, 0.053 mmol). The mixture was purged with nitrogen and heated to 100° C. After 1 h, the mixture was cooled to room temperature and diluted with EtOAc (20 mL). The organic layer was washed with 1 M HCl (1×20 mL), water (1×20 mL), dried over Na$_2$SO$_4$, filtered, and concentrated in vacuo. The crude material was diluted in dichloromethane (1 mL) and trifluoroacetic acid (2 mL) and stirred at room temperature for 5 h. The mixture was concentrated and purified by reverse-phase HPLC (C18 column, acetonitrile-H$_2$O with 0.1% TFA as eluent) to afford the titled compound. $^1$H NMR (400 MHz, Chloroform-d) δ 8.18-8.10 (m, 2H), 7.72-7.59 (m, 2H), 7.40-7.35 (m, 2H), 7.29 (d, J=2.1 Hz, 1H), 7.28-7.26 (m, 1H), 7.24 (d, J=7.7 Hz, 2H), 6.87-6.81 (m, 1H), 1.91 (s, 3H), 1.30 (s, 9H); MS: (ES) m/z calculated for C$_{26}$H$_{25}$ClNO$_3$ [M+H]$^+$ 434.1, found 434.2.

Example 6: Synthesis of 5-[(3R)-5-chloro-3-(2,2-dimethylchroman-6-yl)-3-methyl-2-oxo-indolin-1-yl]-2-methoxy-benzoic acid

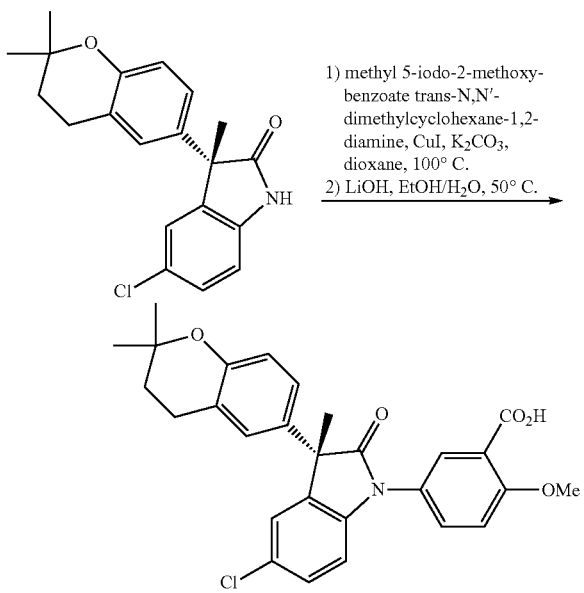

To a solution of (3R)-5-chloro-3-(2,2-dimethylchroman-6-yl)-3-methylindolin-2-one (60 mg, 0.18 mmol), methyl 5-iodo-2-methoxybenzoate (80 mg, 0.27 mmol), trans-N,N'-dimethylcyclohexane-1,2-diamine (10 mg, 0.07 mmol), and potassium carbonate (102 mg, 0.73 mmol)) in dioxane (3.0 mL) was added copper iodide (20 mg, 0.10 mmol). The mixture was purged with nitrogen and heated to 100° C. After 1 h, the mixture was cooled to room temperature and diluted with EtOAc (20 mL). The organic layer was washed with 1 M HCl (1×20 mL), water (1×20 mL), dried over Na$_2$SO$_4$, filtered, and concentrated in vacuo. The crude material was re-dissolved in a mixture of ethanol (2 mL) and water (1 mL). Lithium hydroxide monohydrate (100 mg, 2.4 mmol) was added and the mixture was stirred at 50° C. for 30 min. After cooling to room temperature, the reaction was quenched by the addition of 1 M HCl (25 mL) and extracted with EtOAc (50 mL). The organic layer was washed with water (1×20 mL), dried over Na$_2$SO$_4$, filtered, and concentrated in vacuo. Purification of the crude material by reverse-phase HPLC (C18 column, acetonitrile-H$_2$O with 0.1% TFA as eluent) gave the titled compound. $^1$H NMR (400 MHz, Chloroform-d) δ 8.21 (d, J=2.7 Hz, 1H), 7.66 (dd, J=8.9, 2.7

Hz, 1H), 7.29-7.16 (m, 3H), 7.01 (d, J=2.4 Hz, 1H), 6.96 (dd, J=8.6, 2.5 Hz, 1H), 6.78 (dd, J=8.1, 0.7 Hz, 1H), 6.73 (d, J=8.6 Hz, 1H), 4.13 (s, 3H), 2.75 (t, J=6.7 Hz, 2H), 1.85 (s, 3H), 1.78 (t, J=6.7 Hz, 2H), 1.32 (s, 6H); MS: (ES) m/z calculated for $C_{28}H_{27}ClNO_5$ $[M+H]^+$ 492.2, found 492.3.

Example 7: Synthesis of 5-[(3R)-3-(2,2-dimethyl-chroman-6-yl)-3,5-dimethyl-2-oxo-indolin-1-yl]-2-methyl-benzoic acid

Example 8: Synthesis of 2-[4-[(3R)-5-chloro-3-(2,2-dimethylchroman-6-yl)-3-methyl-2-oxo-indolin-1-yl]phenyl]acetic acid

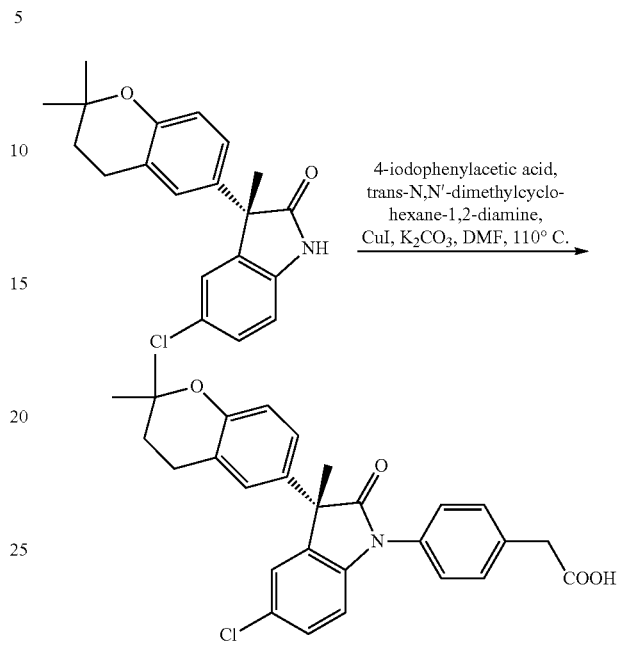

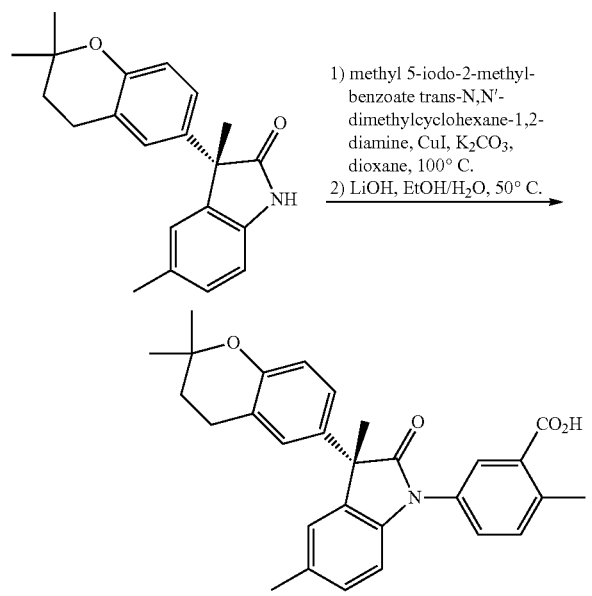

To a solution of (3R)-3-(2,2-dimethylchroman-6-yl)-3,5-dimethylindolin-2-one (32 mg, 0.10 mmol), methyl 5-iodo-2-methylbenzoate (36 mg, 0.13 mmol), trans-N,N'-dimethylcyclohexane-1,2-diamine (10 mg, 0.07 mmol), and potassium carbonate (28 mg, 0.20 mmol)) in dioxane (3.0 mL) was added copper iodide (6.0 mg, 0.03 mmol). The mixture was purged with nitrogen and heated to 100° C. After 1 h, the mixture was cooled to room temperature and diluted with EtOAc (20 mL). The organic layer was washed with 1 M HCl (1×20 mL), water (1×20 mL), dried over $Na_2SO_4$, filtered, and concentrated in vacuo. The crude material was re-dissolved in a mixture of ethanol (2 mL) and water (1 mL). Lithium hydroxide monohydrate (100 mg, 2.4 mmol) was added and the mixture was stirred at 50° C. for 30 min. After cooling to room temperature, the reaction was quenched by the addition of 1 M HCl (25 mL) and extracted with EtOAc (50 mL). The organic layer was washed with water (1×20 mL), dried over $Na_2SO_4$, filtered, and concentrated in vacuo. Purification of the crude material by reverse-phase HPLC (C18 column, acetonitrile-$H_2O$ with 0.1% TFA as eluent) gave the titled compound. $^1$H NMR (400 MHz, Chloroform-d) δ 8.19 (t, J=1.9 Hz, 1H), 8.13-8.06 (m, 1H), 7.76-7.69 (m, 1H), 7.61 (t, J=7.9 Hz, 1H), 7.14-7.03 (m, 3H), 7.03-6.97 (m, 1H), 6.86-6.77 (m, 1H), 6.71 (d, J=8.6 Hz, 1H), 2.75 (t, J=6.8 Hz, 2H), 2.36 (d, J=0.9 Hz, 3H), 1.85 (s, 3H), 1.78 (t, J=6.7 Hz, 2H), 1.31 (d, J=1.8 Hz, 6H); MS: (ES) m/z calculated for $C_{29}H_{30}NO_4$ $[M+H]^+$ 456.6, found 456.0.

To a solution of (3R)-5-chloro-3-(2,2-dimethylchroman-6-yl)-3-methyl-indolin-2-one (60 mg, 0.18 mmol), 4-iodophenylacetic acid (92 mg, 0.35 mmol), trans-N,N'-dimethylcyclohexane-1,2-diamine (10 mg, 0.07 mmol), and potassium carbonate (97 mg, 0.70 mmol) in dimethylformamide (3.0 mL) was added copper iodide (20 mg, 0.10 mmol). The mixture was purged with nitrogen and heated to 110° C. After 1 h, the mixture was cooled to room temperature and diluted with EtOAc (20 mL). The organic layer was washed with 1 M HCl (1×20 mL), water (1×20 mL), dried over $Na_2SO_4$, filtered, and concentrated in vacuo. Purification of the crude material by reverse-phase HPLC (C18 column, acetonitrile-$H_2O$ with 0.1% TFA as eluent) gave the titled compound. $^1$H NMR (400 MHz, Chloroform-d) δ 7.49-7.41 (m, 2H), 7.41-7.34 (m, 2H), 7.20 (dq, J=4.3, 2.1 Hz, 2H), 7.04 (d, J=2.3 Hz, 1H), 6.96 (ddd, J=8.6, 1.9, 1.2 Hz, 1H), 6.85 (d, J=8.9 Hz, 1H), 6.71 (d, J=8.5 Hz, 1H), 3.71 (s, 2H), 2.74 (t, J=6.7 Hz, 2H), 1.84 (s, 3H), 1.78 (t, J=6.7 Hz, 2H), 1.31 (d, J=1.8 Hz, 6H); MS: (ES) m/z calculated for $C_{28}H_{27}ClNO_4[M+H]^+$ 476.2, found 476.2.

Example 9: Synthesis of (S)-5-chloro-3-(2,2-dimethylchroman-6-yl)-3-methyl-1-(4-((5-oxo-4,5-dihydro-1H-tetrazol-1-yl)methyl)phenyl)indolin-2-one

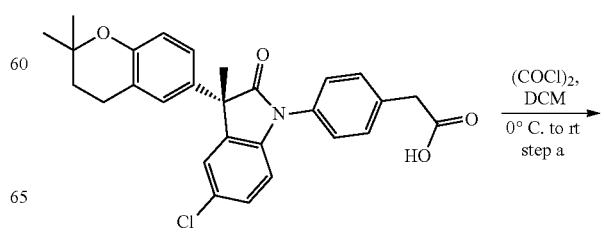

-continued

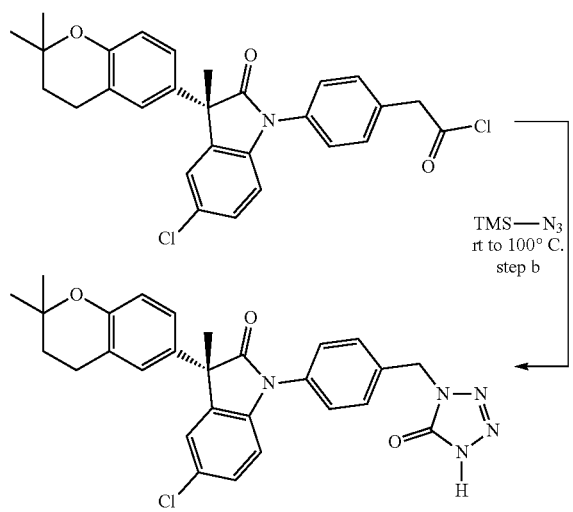

Step a:

To a solution of (S)-2-(4-(5-chloro-3-(2,2-dimethylchroman-6-yl)-3-methyl-2-oxoindolin-1-yl)phenyl)acetic acid (190.4 mg, 0.40 mmol) in dichloromethane (1.6 mL) at 0° C. under nitrogen, a solution of oxalyl chloride (52 μL, 0.60 mmol) in dichloromethane (0.3 mL) was added dropwise. The reaction mixture was stirred at 0° C. for 5 min and then warmed to room temperature and stirred for 4 hours. All solvents were removed under vacuum and dichloromethane (2 mL) was added to the residue. The mixture was concentrated under vacuum and this process was repeated another time to give the acid chloride product which was used in the next step directly.

Step b:

To the acid chloride prepared in the previous step was added azidotrimethylsilane (0.32 mL, 2.4 mmol) at room temperature (gas evolution!). The mixture was heated to 100° C. under nitrogen and stirred for 37 h. The reaction mixture was cooled to room temperature and concentrated under vacuum. Water and dichloromethane were added to the residue. The organic layer was separated, dried, and concentrated. The crude product was purified by silica gel chromatography (50% ethyl acetate/hexane) to give the desired product. $^1$H NMR (400 MHz, chloroform-d) δ 7.58-7.51 (m, 2H), 7.47-7.41 (m, 2H), 7.22-7.16 (m, 2H), 7.03 (d, J=2.4 Hz, 1H), 6.96 (dd, J=8.6, 2.5 Hz, 1H), 6.85-6.80 (m, 1H), 6.70 (d, J=8.6 Hz, 1H), 5.16 (s, 2H), 2.73 (t, J=6.7 Hz, 2H), 1.83 (s, 3H), 1.77 (t, J=6.7 Hz, 2H), 1.30 (d, J=2.0 Hz, 6H). MS: (ES) m/z calculated for $C_{28}H_{26}ClN_5O_3$ [M+H]$^+$ 516.2, found 516.5.

Example 10: Synthesis of (S)-5-chloro-3-(2,2-dimethylchroman-6-yl)-3-methyl-1-(4-((4-methyl-5-oxo-4,5-dihydro-1H-tetrazol-1-yl)methyl)phenyl)indolin-2-one

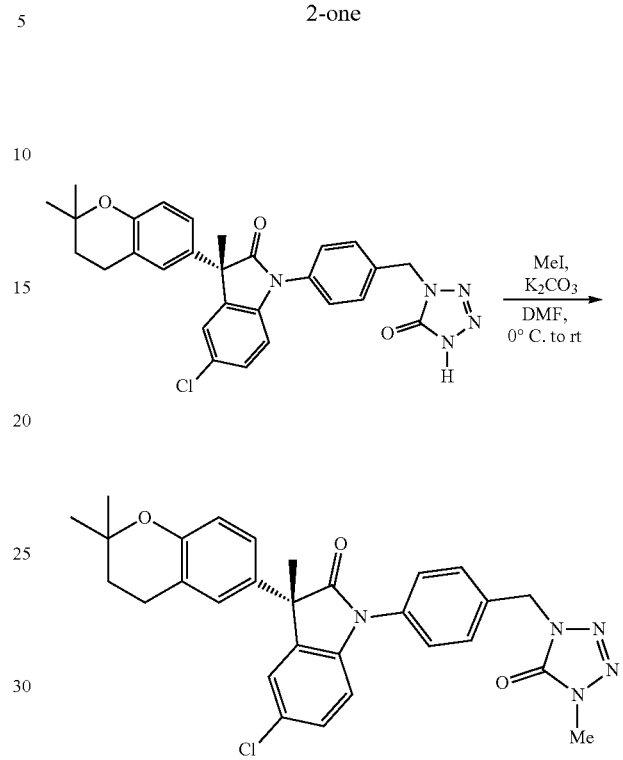

To a mixture of (S)-5-chloro-3-(2,2-dimethylchroman-6-yl)-3-methyl-1-(4-((5-oxo-4,5-dihydro-1H-tetrazol-1-yl)methyl)phenyl)indolin-2-one (204 mg, 0.395 mmol) and iodomethane (49 μL, 0.791 mmol) in DMF (1.0 mL) at 0° C. was added $K_2CO_3$ (138 mg, 1.0 mmol). The reaction mixture was stirred at 0° C. for 20 min and then room temperature for 14 h. The mixture was poured into water (10 mL) and dichloromethane (3 mL). The organic layer was separated and the aqueous layer was extracted with dichloromethane. The combined organic layers were dried and concentrated. The crude product was purified by silica gel chromatography (50% ethyl acetate/hexane) to give the desired product. $^1$H NMR (400 MHz, chloroform-d) δ 7.58-7.52 (m, 2H), 7.44-7.39 (m, 2H), 7.21-7.16 (m, 2H), 7.03 (d, J=2.4 Hz, 1H), 6.98-6.93 (m, 1H), 6.85-6.80 (m, 1H), 6.70 (d, J=8.6 Hz, 1H), 5.13 (s, 2H), 3.61 (s, 3H), 2.73 (t, J=6.7 Hz, 2H), 1.82 (s, 3H), 1.76 (t, J=6.7 Hz, 2H), 1.30 (d, J=1.8 Hz, 6H). MS: (ES) m/z calculated for $C_{29}H_{28}ClN_5O_3$ [M+H]$^+$ 530.2, found 530.5.

Compounds prepared by methods analogous to the methods described above, and evaluated using the serum chemotaxis assay below are provided in the following table. $A_2$ was calculated as described and activity is presented in Table 1 as:

TABLE 1

| | ¹H NMR | MS: (ES) m/z | Chemotaxis A₂ |
|---|---|---|---|
| 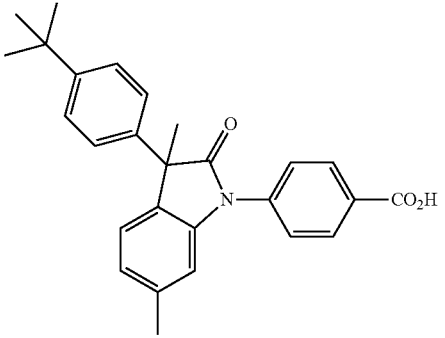<br>1.001 | ¹H NMR (400 MHz, Chloroform-d) δ 8.28-8.19 (m, 2H), 7.59 (dt, J = 8.4, 0.5 Hz, 2H), 7.34 (d, J = 9.1 Hz, 2H), 7.31-7.27 (m, 2H), 7.17 (d, J = 7.6 Hz, 1H), 7.03-6.94 (m, 1H), 6.85-6.78 (m, 1H), 2.36 (s, 3H), 1.89 (s, 3H), 1.29 (s, 9H). | 414.3 [M + H]⁺ | ++ |
| 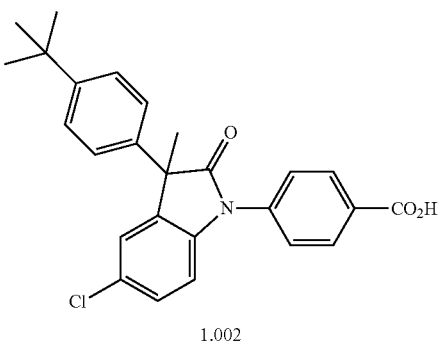 [SMILES: CC(C)(C)c1ccc(C2(C)C(=O)N(c3ccc(C(=O)O)cc3)c3ccc(Cl)cc32)cc1]<br>1.002 | ¹H NMR (400 MHz, Methanol-d₄) δ 8.28-8.17 (m, 2H), 7.66-7.56 (m, 2H), 7.41 (d, J = 8.5 Hz, 2H), 7.31 (dd, J = 8.4, 2.2 Hz, 1H), 7.27 (s, 2H), 7.25 (d, J = 0.6 Hz, 1H), 6.96 (d, J = 8.4 Hz, 1H), 1.88 (s, 3H), 1.30 (s, 9H). | 434.1 [M + H]⁺ | +++ |
| 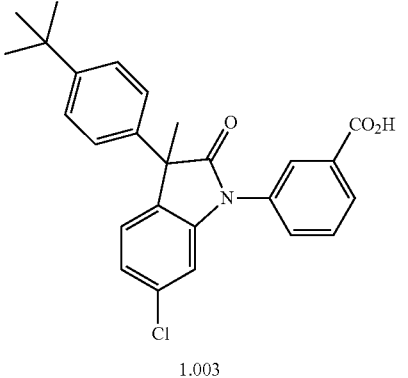 [SMILES: CC(C)(C)c1ccc(C2(C)C(=O)N(c3cccc(C(=O)O)c3)c3cc(Cl)ccc32)cc1]<br>1.003 | ¹H NMR (400 MHz, Chloroform-d) δ 8.21-8.12 (m, 1H), 7.72 (dtd, J = 9.3, 7.7, 1.6 Hz, 1H), 7.54 (td, J = 7.6, 1.1 Hz, 1H), 7.44-7.36 (m, 1H), 7.36-7.32 (m, 2H), 7.32-7.27 (m, 2H), 7.24-7.14 (m, 2H), 6.53 (dd, J = 17.9, 8.7 Hz, 1H), 1.76 (s, 3H), 1.28 (d, J = 12.5 Hz, 9H). | 434.1 [M + H]⁺ | ++ |
| 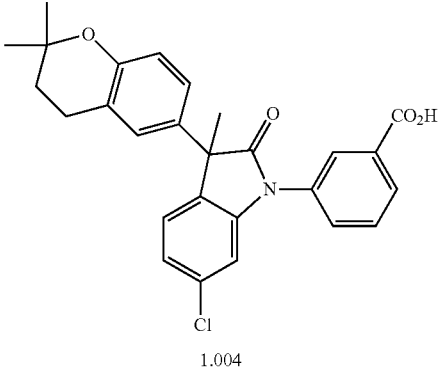 [SMILES: CC1(C)CCc2cc(C3(C)C(=O)N(c4cccc(C(=O)O)c4)c4cc(Cl)ccc43)ccc2O1]<br>1.004 | ¹H NMR (400 MHz, Chloroform-d) δ 8.19-8.07 (m, 2H), 7.78-7.58 (m, 2H), 7.21-7.16 (m, 1H), 7.13 (dd, J = 8.0, 1.9 Hz, 1H), 7.05 (d, J = 2.4 Hz, 1H), 7.00 (dd, J = 8.6, 2.5 Hz, 1H), 6.88 (d, J = 1.8 Hz, 1H), 6.72 (d, J = 8.6 Hz, 1H), 2.74 (t, J = 6.7 Hz, 2H), 1.85 (s, 3H), 1.78 (t, J = 6.7 Hz, 2H), 1.33-1.30 (m, 6H). | 461.9 [M + H]⁺ | ++ |

TABLE 1-continued

| | ¹H NMR | MS: (ES) m/z | Chemotaxis A₂ |
|---|---|---|---|
| 1.005 | ¹H NMR (400 MHz, Chloroform-d) δ 8.14 (dt, J = 4.1, 1.9 Hz, 2H), 7.71-7.60 (m, 2H), 7.30-7.26 (m, 1H), 7.25 (q, J = 1.8 Hz, 2H), 7.06-6.96 (m, 2H), 6.86 (d, J = 8.2 Hz, 1H), 1.89 (s, 3H), 1.36 (d, J = 1.0 Hz, 9H). | 474.1 [M + Na]⁺ | +++ |
| 1.006 | ¹H NMR (400 MHz, Chloroform-d) δ 8.20-8.06 (m, 2H), 7.71 (d, J = 7.9 Hz, 1H), 7.66-7.57 (m, 1H), 7.35 (dd, J = 8.6, 1.2 Hz, 2H), 7.32-7.28 (m, 2H), 7.11-7.03 (m, 2H), 6.83 (d, J = 8.0 Hz, 1H), 2.36 (s, 4H), 1.90 (d, J = 1.2 Hz, 3H), 1.30 (d, J = 1.2 Hz, 9H). | 414.2 [M + H]⁺ | ++ |
| 1.007 | ¹H NMR (400 MHz, Chloroform-d) δ 8.22 (d, J = 8.5 Hz, 2H), 7.60 (d, J = 8.6 Hz, 2H), 7.35 (d, J = 8.6 Hz, 2H), 7.31-7.27 (m, 2H), 7.08 (d, J = 10.0 Hz, 2H), 6.92 (d, J = 7.9 Hz, 1H), 2.36 (s, 3H), 1.89 (s, 3H), 1.29 (d, J = 0.4 Hz, 9H). | 414.2 [M + H]⁺ | ++ |
| 1.008 | ¹H NMR (400 MHz, Chloroform-d) δ 8.33-8.24 (m, 2H), 7.65-7.60 (m, 2H), 7.58 (d, J = 8.4 Hz, 1H), 7.35-7.29 (m, 1H), 7.25-7.19 (m, 1H), 7.10 (dd, J = 2.3, 0.8 Hz, 1H), 6.98-6.88 (m, 2H), 1.90 (s, 3H), 1.84 (s, 3H), 1.31 (d, J = 0.4 Hz, 9H). | 448.1 [M + H]⁺ | ++ |

TABLE 1-continued

| | ¹H NMR | MS: (ES) m/z | Chemotaxis A₂ |
|---|---|---|---|
| 1.009 | ¹H NMR (400 MHz, Chloroform-d) δ 8.20-8.14 (m, 2H), 7.77-7.71 (m, 1H), 7.71-7.65 (m, 1H), 7.58 (d, J = 8.3 Hz, 1H), 7.35-7.31 (m, 1H), 7.20 (dd, J = 8.4, 2.2 Hz, 1H), 7.13-7.09 (m, 1H), 6.94 (d, J = 2.1 Hz, 1H), 6.84 (d, J = 8.4 Hz, 1H), 1.90 (s, 3H), 1.86 (s, 3H), 1.31 (s, 9H). | 448.1 [M + H]⁺ | +++ |
| 1.010 | ¹H NMR (400 MHz, Chloroform-d) δ 8.18-8.09 (m, 2H), 7.71-7.66 (m, 1H), 7.63 (dd, J = 8.2, 7.4 Hz, 1H), 7.27-7.24 (m, 2H), 7.23 (dq, J = 1.5, 0.7 Hz, 2H), 6.88-6.80 (m, 3H), 4.52 (p, J = 6.1 Hz, 1H), 1.88 (s, 3H), 1.32 (d, J = 6.0 Hz, 6H). | 436.1 [M + H]⁺ | +++ |
| 1.011 | ¹H NMR (400 MHz, Chloroform-d) δ 8.15 (dd, J = 9.0, 1.7 Hz, 1H), 8.02 (d, J = 22.0 Hz, 1H), 7.62-7.50 (m, 2H), 7.37 (d, J = 8.1 Hz, 3H), 7.24 (dd, J = 1.6, 0.8 Hz, 2H), 7.14 (d, J = 2.0 Hz, 1H), 1.90 (s, 3H), 1.30 (d, J = 0.5 Hz, 9H). | 468.2 [M + H]⁺ | + |
| 1.012 | ¹H NMR (400 MHz, Chloroform-d) δ 8.21-8.12 (m, 1H), 7.72 (dtd, J = 9.3, 7.7, 1.6 Hz, 1H), 7.54 (td, J = 7.6, 1.1 Hz, 1H), 7.44-7.36 (m, 1H), 7.36-7.32 (m, 2H), 7.32-7.27 (m, 2H), 7.24-7.14 (m, 2H), 6.53 (dd, J = 17.9, 8.7 Hz, 1H), 1.76 (s, 3H), 1.28 (d, J = 12.5 Hz, 9H). | 434.2 [M + H]⁺ | ++ |

TABLE 1-continued
| | ¹H NMR | MS: (ES) m/z | Chemotaxis A₂ |
|---|---|---|---|
| 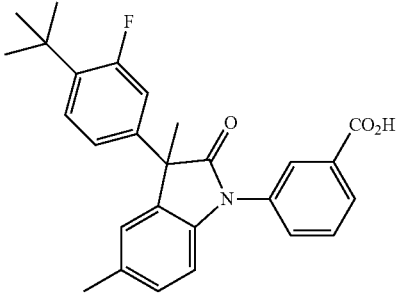<br>1.013 | ¹H NMR (400 MHz, Chloroform-d) δ 8.17 (s, 1H), 8.11 (d, J = 7.7 Hz, 1H), 7.74-7.67 (m, 1H), 7.62 (t, J = 7.8 Hz, 1H), 7.25-7.23 (m, 1H), 7.09-7.05 (m, 3H), 7.01 (dd, J = 13.9, 2.1 Hz, 1H), 6.83 (d, J = 8.4 Hz, 1H), 2.37 (d, J = 0.9 Hz, 3H), 1.87 (d, J = 0.9 Hz, 3H), 1.35 (t, J = 1.0 Hz, 9H). | 432.2 [M + H]⁺ | +++ |
| 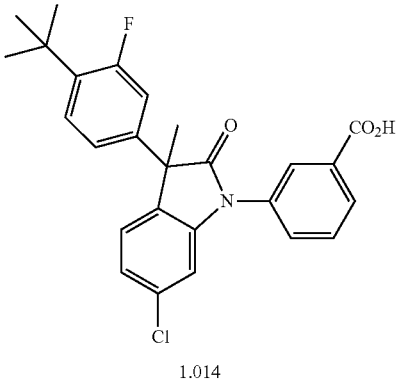 [SMILES: CC(C)(C)c1ccc(C2(C)C(=O)N(c3cccc(C(=O)O)c3)c3cc(Cl)ccc32)cc1F]<br>1.014 | ¹H NMR (400 MHz, Chloroform-d) δ 8.20-8.08 (m, 2H), 7.68-7.63 (m, 2H), 7.26-7.23 (m, 1H), 7.19 (d, J = 7.9 Hz, 1H), 7.16-7.11 (m, 1H), 7.07-6.95 (m, 2H), 6.88 (d, J = 1.8 Hz, 1H), 1.87 (d, J = 0.7 Hz, 3H), 1.35 (d, J = 0.9 Hz, 9H). | 452.2 [M + H]⁺ | + |
| 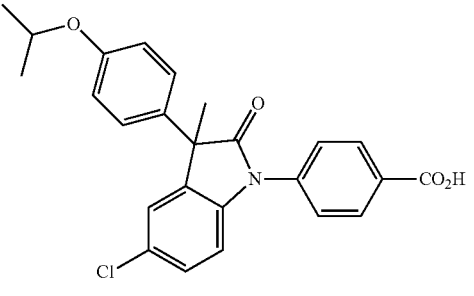<br>1.015 | ¹H NMR (400 MHz, Chloroform-d) δ 8.29-8.22 (m, 2H), 7.61-7.54 (m, 2H), 7.25-7.21 (m, 4H), 7.00-6.93 (m, 1H), 6.87-6.80 (m, 2H), 4.61-4.38 (m, 1H), 1.88 (s, 3H), 1.32 (dd, J = 6.1, 1.2 Hz, 6H). | 436.2 [M + H]⁺ | +++ |
| 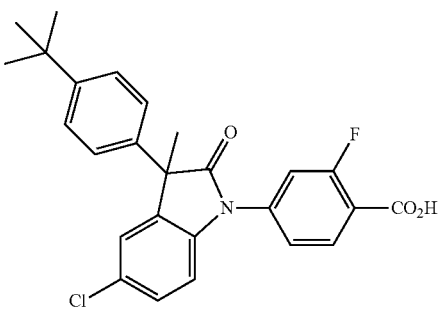<br>1.016 | | 452.2 [M + H]⁺ | ++ |

TABLE 1-continued

| | ¹H NMR | MS: (ES) m/z | Chemotaxis A₂ |
|---|---|---|---|
| 1.017 | | 452.1 [M + H]⁺ | +++ |
| 1.018 | ¹H NMR (400 MHz, Chloroform-d) δ 8.18-8.12 (m, 2H), 7.72-7.68 (m, 1H), 7.64 (t, J = 7.8 Hz, 1H), 7.25-7.21 (m, 1H), 7.16 (d, J = 7.6 Hz, 1H), 7.10-7.05 (m, 1H), 7.04-6.96 (m, 2H), 6.71 (t, J = 1.2 Hz, 1H), 2.36 (d, J = 0.9 Hz, 3H), 1.87 (s, 3H), 1.35 (t, J = 0.7 Hz, 9H). | 432.3 [M + H]⁺ | ++ |
| 1.019 | ¹H NMR (400 MHz, Chloroform-d) δ 8.17 (t, J = 1.9 Hz, 1H), 8.12 (dt, J = 7.5, 1.4 Hz, 1H), 7.71-7.67 (m, 1H), 7.63 (t, J = 7.8 Hz, 1H), 7.35-7.32 (m, 2H), 7.32-7.28 (m, 2H), 7.17 (d, J = 7.6 Hz, 1H), 6.99-6.92 (m, 1H), 6.72-6.69 (m, 1H), 2.35 (d, J = 0.7 Hz, 3H), 1.89 (s, 3H), 1.29 (d, J = 0.5 Hz, 9H). | 414.2 [M + H]⁺ | ++ |
| 1.020 | | 452.1 [M + H]⁺ | ++ |

TABLE 1-continued
| | ¹H NMR | MS: (ES) m/z | Chemotaxis A₂ |
|---|---|---|---|
| 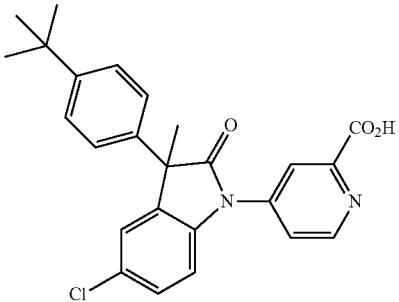 1.021 | ¹H NMR (400 MHz, DMSO-d₆) δ 8.86 (dd, J = 5.3, 0.8 Hz, 1H), 8.36-8.08 (m, 1H), 7.84 (dd, J = 5.3, 2.1 Hz, 1H), 7.47 (d, J = 2.2 Hz, 1H), 7.38 (d, J = 2.6 Hz, 1H), 7.36 (d, J = 2.4 Hz, 2H), 7.24 (d, J = 8.5 Hz, 2H), 7.16 (d, J = 8.5 Hz, 1H), 1.84 (s, 3H), 1.23 (s, 9H). | 435.0 [M + H]⁺ | ++ |
| 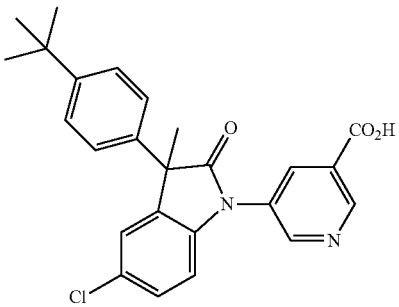 1.022 | ¹H NMR (400 MHz, DMSO-d₆) δ 9.11 (d, J = 1.9 Hz, 1H), 8.97 (d, J = 2.4 Hz, 1H), 8.40 (ddd, J = 2.5, 1.9, 0.6 Hz, 1H), 7.45 (d, J = 2.2 Hz, 1H), 7.37 (d, J = 8.5 Hz, 2H), 7.32 (ddd, J = 8.5, 2.2, 0.6 Hz, 1H), 7.30-7.26 (m, 2H), 6.95 (d, J = 8.5 Hz, 1H), 1.84 (s, 3H), 1.24 (d, J = 0.6 Hz, 9H). | 435.0 [M + H]⁺ | ++ |
| 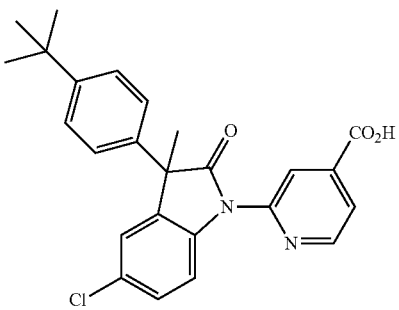 1.023 | ¹H NMR (400 MHz, DMSO-d₆) δ 8.81-8.77 (m, 1H), 8.20 (dd, J = 1.5, 0.8 Hz, 1H), 7.87-7.78 (m, 1H), 7.71 (d, J = 8.6 Hz, 1H), 7.45 (d, J = 2.3 Hz, 1H), 7.41-7.34 (m, 3H), 7.27-7.19 (m, 2H), 1.84 (s, 3H), 1.23 (s, 9H). | 435.0 [M + H]⁺ | +++ |
| 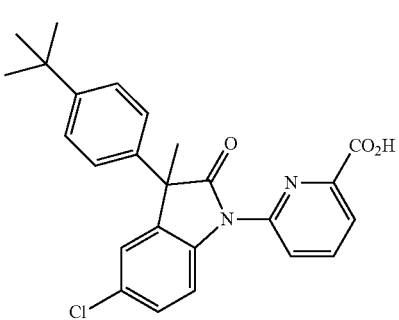 1.024 | ¹H NMR (400 MHz, DMSO-d₆) δ 8.19-8.13 (m, 1H), 8.10-8.00 (m, 2H), 7.97 (dt, J = 8.6, 0.5 Hz, 1H), 7.48-7.44 (m, 1H), 7.41 (ddd, J = 8.6, 2.3, 0.6 Hz, 1H), 7.39-7.33 (m, 2H), 7.24-7.19 (m, 2H), 1.84 (s, 3H), 1.23 (d, J = 0.6 Hz, 9H). | 456.9 [M + Na]⁺ | ++ |

TABLE 1-continued
| | ¹H NMR | MS: (ES) m/z | Chemotaxis A₂ |
|---|---|---|---|
| 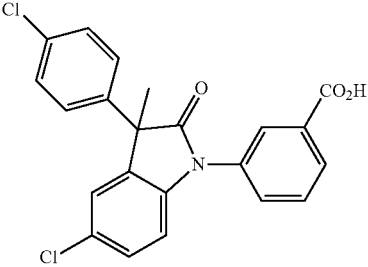 1.025 | ¹H NMR (400 MHz, Chloroform-d) δ 8.14 (d, J = 5.4 Hz, 2H), 7.66 (d, J = 7.1 Hz, 2H), 7.35-7.31 (m, 2H), 7.31 (d, J = 1.8 Hz, 2H), 7.29-7.27 (m, 1H), 7.23-7.21 (m, 1H), 6.86 (d, J = 8.4 Hz, 1H), 1.89 (s, 3H). | 434.1 [M + Na]⁺ | + |
| 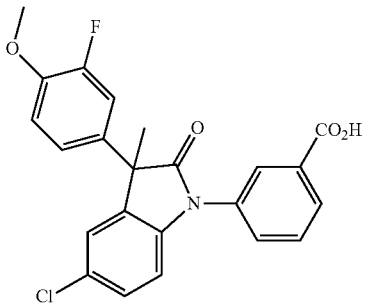 1.026 | ¹H NMR (400 MHz, Chloroform-d) δ 7.84 (d, J = 64.1 Hz, 2H), 7.24-7.13 (m, 2H), 7.08 (d, J = 1.8 Hz, 1H), 7.03 (d, J = 7.8 Hz, 1H), 6.99-6.87 (m, 2H), 6.78 (t, J = 8.6 Hz, 1H), 6.63 (s, 1H), 3.74 (s, 3H), 1.63 (s, 3H). | 426.2 [M + H]⁺ | + |
| 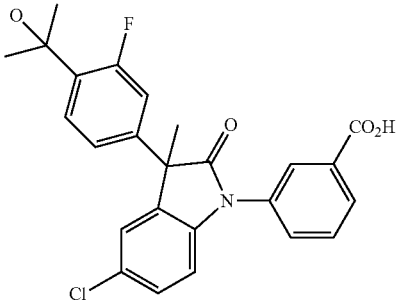 1.027 | ¹H NMR (400 MHz, Chloroform-d) δ 8.17-8.11 (m, 2H), 7.69 (dt, J = 7.9, 1.7 Hz, 1H), 7.64 (t, J = 8.0 Hz, 1H), 7.52-7.41 (m, 2H), 7.37-7.28 (m, 2H), 7.25-7.22 (m, 1H), 6.86 (dd, J = 8.1, 0.8 Hz, 1H), 1.92 (s, 3H), 1.57 (s, 6H). | 457.9 [M + Na]⁺ | ++ |
| 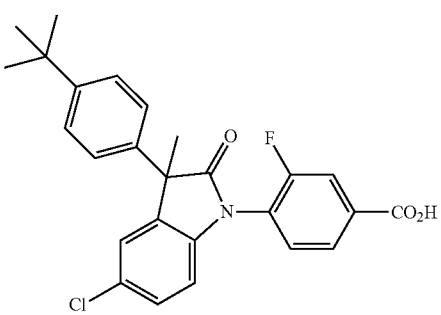 1.028 | ¹H NMR (400 MHz, DMSO-d₆) δ 8.03 (t, J = 8.3 Hz, 1H), 7.57 (dd, J = 11.5, 1.9 Hz, 1H), 7.45 (td, J = 4.1, 1.9 Hz, 2H), 7.39-7.29 (m, 3H), 7.28-7.22 (m, 2H), 7.02 (d, J = 8.5 Hz, 1H), 1.82 (s, 3H), 1.24 (d, J = 0.6 Hz, 9H). | 452.1 [M + H]⁺ | ++ |

TABLE 1-continued
| | ¹H NMR | MS: (ES) m/z | Chemotaxis A₂ |
|---|---|---|---|
| 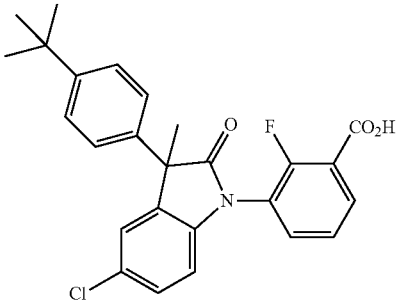 1.029 | ¹H NMR (400 MHz, Chloroform-d) δ 8.13 (t, J = 7.1 Hz, 1H), 7.76-7.58 (m, 1H), 7.47-7.32 (m, 3H), 7.32-7.26 (m, 2H), 7.26-7.19 (m, 2H), 6.63 (dd, J = 8.6, 5.5 Hz, 1H), 1.92 (s, 3H), 1.30 (dd, J = 5.2, 1.0 Hz, 9H). | 452.1 [M + H]⁺ | +++ |
| 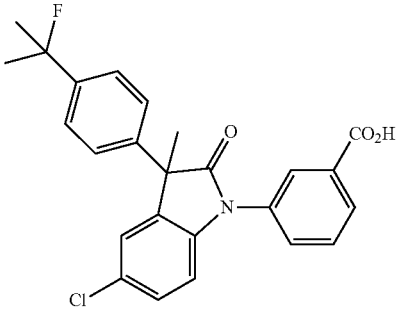 1.030 | ¹H NMR (400 MHz, Chloroform-d) δ 8.16-8.12 (m, 2H), 7.72-7.61 (m, 2H), 7.39-7.36 (m, 2H), 7.36-7.32 (m, 2H), 7.24 (t, J = 1.1 Hz, 2H), 6.86 (dd, J = 8.1, 0.9 Hz, 1H), 1.92 (d, J = 1.0 Hz, 3H), 1.67 (d, J = 21.9 Hz, 6H). | 459.9 [M + Na]⁺ | ++ |
| 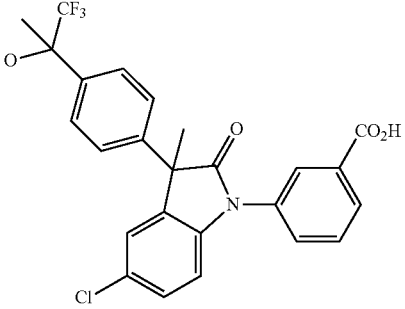 1.031 | ¹H NMR (400 MHz, Chloroform-d) δ 8.14 (d, J = 4.1 Hz, 2H), 7.74-7.62 (m, 2H), 7.57 (d, J = 8.5 Hz, 2H), 7.39 (d, J = 8.2 Hz, 2H), 7.26-7.23 (m, 2H), 6.87 (d, J = 8.1 Hz, 1H), 1.93 (s, 3H), 1.76 (s, 3H). | 511.8 [M + Na]⁺ | ++ |
| 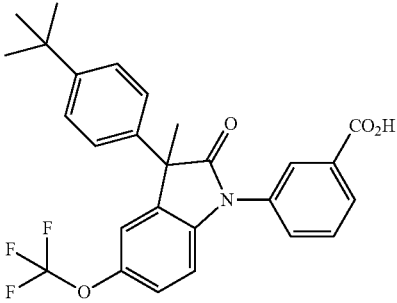 1.032 | ¹H NMR (400 MHz, Methanol-d₄) δ 8.17-8.11 (m, 1H), 8.10-8.05 (m, 1H), 7.72 (d, J = 1.3 Hz, 1H), 7.71-7.70 (m, 1H), 7.42 (d, J = 2.0 Hz, 1H), 7.41 (d, J = 2.0 Hz, 1H), 7.27 (d, J = 8.5 Hz, 2H), 7.22 (q, J = 1.0 Hz, 2H), 7.00-6.94 (m, 1H), 1.91 (s, 3H), 1.31 (s, 9H). | 484.2 [M + H]⁺ | +++ |

TABLE 1-continued

| | ¹H NMR | MS: (ES) m/z | Chemotaxis A₂ |
|---|---|---|---|
| 1.033 (5-Cl indolinone with 3-Me, 3-(4-(1-CF₃-cyclopropyl)phenyl), N-(3-CO₂H-phenyl)) | ¹H NMR (400 MHz, Chloroform-d) δ 8.14 (dt, J = 4.0, 1.8 Hz, 2H), 7.68 (d, J = 2.1 Hz, 1H), 7.67-7.62 (m, 1H), 7.44 (d, J = 8.1 Hz, 2H), 7.35-7.31 (m, 2H), 7.25 (dt, J = 1.0, 0.5 Hz, 2H), 6.90-6.82 (m, 1H), 1.91 (d, J = 0.8 Hz, 3H), 1.44-1.25 (m, 2H), 1.00 (s, 2H). | 486.1 [M + H]⁺ | +++ |
| 1.034 (5-Cl indolinone with 3-Me, 3-(4-(1-CN-cyclopropyl)phenyl), N-(3-CO₂H-phenyl)) | ¹H NMR (400 MHz, Chloroform-d) δ 8.17-8.11 (m, 2H), 7.70-7.61 (m, 2H), 7.37-7.32 (m, 2H), 7.29 (d, J = 2.2 Hz, 1H), 7.28-7.27 (m, 2H), 7.22 (d, J = 2.1 Hz, 1H), 6.86 (d, J = 8.4 Hz, 1H), 1.90 (s, 3H), 1.79-1.60 (m, 2H), 1.44-1.27 (m, 2H). | 443.1 [M + H]⁺ | ++ |
| 1.035 (5-Cl indolinone with 3-Me, 3-(4-(1-Me-cyclopropyl)phenyl), N-(3-CO₂H-phenyl)) | ¹H NMR (400 MHz, Chloroform-d) δ 8.17-8.09 (m, 2H), 7.68 (d, J = 8.2 Hz, 1H), 7.66-7.60 (m, 1H), 7.24 (dtd, J = 2.6, 1.1, 0.6 Hz, 3H), 7.24-7.20 (m, 3H), 6.85 (d, J = 9.0 Hz, 1H), 1.89 (s, 3H), 1.39 (s, 3H), 0.84 (s, 2H), 0.78-0.64 (m, 2H). | 432.2 [M + H]⁺ | +++ |
| 1.036 (5-Cl indolinone with 3-Me, 3-(4-iPrO-3-Me-phenyl), N-(3-CO₂H-phenyl)) | ¹H NMR (400 MHz, Chloroform-d) δ 8.24-8.09 (m, 2H), 7.71 (ddd, J = 8.0, 2.1, 1.4 Hz, 1H), 7.65 (t, J = 8.0 Hz, 1H), 7.26 (dd, J = 2.6, 0.4 Hz, 1H), 7.25-7.21 (m, 1H), 7.09-7.06 (m, 1H), 7.05 (dt, J = 8.6, 1.6 Hz, 1H), 6.84 (dt, J = 8.2, 0.5 Hz, 1H), 6.78 (d, J = 8.6 Hz, 1H), 4.49 (p, J = 6.0 Hz, 1H), 2.18 (s, 3H), 1.88 (s, 3H), 1.32 (dd, J = 6.0, 0.5 Hz, 6H). | 450.2 [M + H]⁺ | ++ |

TABLE 1-continued

| | ¹H NMR | MS: (ES) m/z | Chemotaxis A₂ |
|---|---|---|---|
| 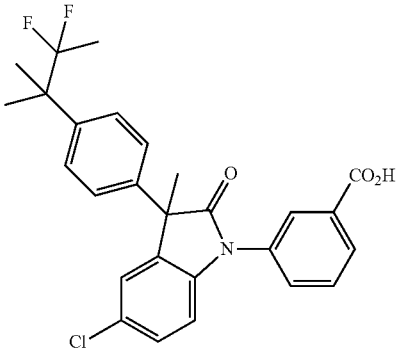<br>1.037 | ¹H NMR (400 MHz, Methanol-d₄) δ 7.60-7.56 (m, 2H), 7.56-7.53 (m, 3H), 7.40-7.35 (m, 2H), 7.31-7.29 (m, 1H), 7.28 (q, J = 1.9 Hz, 2H), 6.84 (d, J = 9.1 Hz, 1H), 1.90 (s, 3H), 1.57 (s, 3H), 1.56 (s, 6H). | 484.2 [M + H]⁺ | + |
| 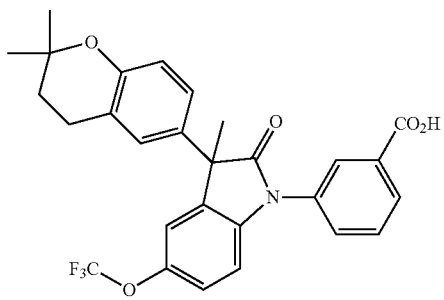<br>1.038 | ¹H NMR (400 MHz, Chloroform-d) δ 8.22-8.11 (m, 2H), 7.73-7.68 (m, 1H), 7.65 (t, J = 7.7 Hz, 1H), 7.14 (d, J = 9.1 Hz, 2H), 7.05 (d, J = 2.4 Hz, 1H), 6.99 (dd, J = 8.5, 2.6 Hz, 1H), 6.94-6.87 (m, 1H), 6.73 (d, J = 8.6 Hz, 1H), 2.75 (t, J = 6.7 Hz, 2H), 1.88 (s, 3H), 1.78 (t, J = 6.7 Hz, 2H), 1.32 (s, 6H). | 512.2 [M + H]⁺ | +++ |
| 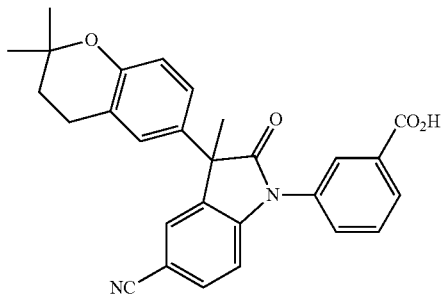<br>1.039 | ¹H NMR (400 MHz, Chloroform-d) δ 8.21-8.16 (m, 1H), 8.15-8.10 (m, 1H), 7.69-7.65 (m, 2H), 7.62-7.54 (m, 1H), 7.53 (d, J = 1.6 Hz, 1H), 7.02 (d, J = 2.5 Hz, 1H), 6.99-6.94 (m, 2H), 6.74 (d, J = 8.6 Hz, 1H), 2.76 (t, J = 6.8 Hz, 2H), 1.89 (s, 3H), 1.82-1.75 (m, 2H), 1.33 (d, J = 1.1 Hz, 6H). | 453.2 [M + H]⁺ | +++ |
| 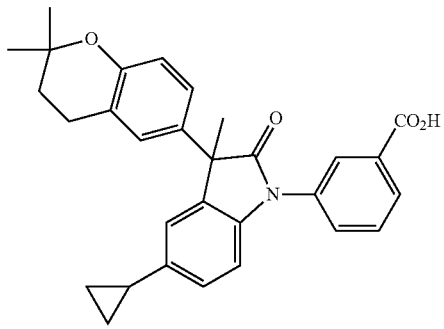<br>1.040 | ¹H NMR (400 MHz, Chloroform-d) δ 8.16 (dt, J = 10.3, 1.5 Hz, 1H), 8.14-8.06 (m, 1H), 7.76-7.68 (m, 1H), 7.68-7.57 (m, 1H), 7.42-7.33 (m, 1H), 7.07 (dd, J = 14.5, 2.5 Hz, 1H), 7.02-6.93 (m, 2H), 6.81 (dd, J = 8.3, 7.4 Hz, 1H), 6.75-6.65 (m, 1H), 2.79-2.67 (m, 2H), 1.86 (s, 1H), 1.85 (s, 2H), 1.78 (td, J = 6.7, 2.8 Hz, 2H), 1.32 (t, J = 1.7 Hz, 6H), 0.99-0.92 (m, 1H), 0.69-0.56 (m, 1H). | 468.2 [M + H]⁺ | +++ |

TABLE 1-continued

| | ¹H NMR | MS: (ES) m/z | Chemotaxis A₂ |
|---|---|---|---|
| 1.041 | ¹H NMR (400 MHz, Methanol-d₄) δ 8.10 (ddd, J = 5.0, 3.5, 1.6 Hz, 1H), 8.06 (d, J = 1.8 Hz, 1H), 7.73-7.65 (m, 2H), 7.17-7.12 (m, 1H), 7.08 (dd, J = 17.7, 2.0 Hz, 2H), 6.98 (dd, J = 8.6, 2.5 Hz, 1H), 6.81 (d, J = 8.0 Hz, 1H), 6.66 (d, J = 8.6 Hz, 1H), 2.76 (t, J = 6.8 Hz, 2H), 2.64 (q, J = 7.6 Hz, 2H), 1.83 (s, 3H), 1.79 (t, J = 6.8 Hz, 2H), 1.32-1.27 (m, 6H), 1.21 (t, J = 7.6 Hz, 3H). | 456.3 [M + H]⁺ | +++ |
| 1.042 | ¹H NMR (400 MHz, Chloroform-d) δ 8.18-8.16 (m, 1H), 8.14 (dt, J = 7.8, 1.4 Hz, 1H), 7.71 (ddd, J = 7.9, 2.1, 1.2 Hz, 1H), 7.67-7.61 (m, 1H), 7.25-7.20 (m, 2H), 6.89-6.82 (m, 3H), 2.73 (t, J = 6.8 Hz, 2H), 2.13 (t, J = 0.6 Hz, 3H), 1.85 (s, 3H), 1.76 (t, J = 6.7 Hz, 2H), 1.31 (s, 6H). | 479.5 [M + H]⁺ | +++ |
| 1.043 | ¹H NMR (400 MHz, Methanol-d₄) δ 8.12 (ddd, J = 4.9, 4.1, 1.6 Hz, 1H), 8.05 (q, J = 1.2 Hz, 1H), 7.75-7.58 (m, 2H), 7.37-7.20 (m, 2H), 6.95-6.86 (m, 2H), 6.85-6.79 (m, 1H), 2.79 (t, J = 6.8 Hz, 2H), 1.84 (s, 3H), 1.82 (d, J = 6.8 Hz, 2H), 1.33 (s, 6H). | 502.1 [M + H]⁺ | +++ |
| 1.044 | ¹H NMR (400 MHz, Chloroform-d) δ 8.19-8.12 (m, 2H), 7.70 (ddt, J = 8.6, 1.7, 0.9 Hz, 1H), 7.67-7.60 (m, 1H), 7.25-7.21 (m, 2H), 7.13 (t, J = 1.6 Hz, 1H), 7.04 (dd, J = 8.5, 2.1 Hz, 1H), 6.85 (dd, J= 9.1, 1.1 Hz, 1H), 6.73-6.65 (m, 1H), 3.00 (s,2H), 1.87 (s,3H), 1.69-1.24 (m, 6H). | 448.5 [M + H]⁺ | +++ |

TABLE 1-continued

| | ¹H NMR | MS: (ES) m/z | Chemotaxis A₂ |
|---|---|---|---|
| 1.045 | ¹H NMR (400 MHz, Chloroform-d) δ 8.07-7.92 (m, 2H), 7.57 (dt, J = 4.9, 1.2 Hz, 2H), 7.43-7.29 (m, 1H), 7.25-7.14 (m, 2H), 7.11-6.97 (m, 2H), 6.87-6.71 (m, 1H), 2.52 (d, J = 3.9 Hz, 3H), 1.88 (d, J = 3.1 Hz, 3H), 1.38 (dd, J = 1.3, 0.5 Hz, 9H). | 448.3 [M + Na]⁺ | ++ |
| 1.046 | ¹H NMR (400 MHz, Chloroform-d) δ 8.21-8.16 (m, 1H), 8.15 (tt, J = 1.8, 0.8 Hz, 1H), 7.68-7.63 (m, 2H), 7.23 (q, J = 1.3 Hz, 1H), 7.03 (d, J = 2.4 Hz, 1H), 7.01-6.96 (m, 2H), 6.74 (d, J = 8.5 Hz, 1H), 2.75 (t, J = 6.6 Hz, 2H), 1.88 (s, 3H), 1.79 (t, J = 6.8 Hz, 2H), 1.32 (s, 6H). | 546.3 [M + H]⁺ | +++ |
| 1.047 | ¹H NMR (400 MHz, Chloroform-d) δ 8.20-8.14 (m, 1H), 8.13 (q, J = 1.5 Hz, 1H), 7.67 (d, J = 1.7 Hz, 1H), 7.66 (d, J = 1.6 Hz, 1H), 7.31 (s, 1H), 7.05-6.98 (m, 2H), 6.97 (s, 1H), 6.74 (d, J = 8.6 Hz, 1H), 2.76 (t, J = 6.8 Hz, 2H), 1.86 (s, 3H), 1.78 (d, J = 6.8 Hz, 2H), 1.32 (d, J = 1.5 Hz, 6H). | 518.2 [M + Na]⁺ | +++ |
| 1.048 | ¹H NMR (400 MHz, Chloroform-d) δ 8.18-8.10 (m, 2H), 7.72-7.59 (m, 2H), 7.40-7.35 (m, 2H), 7.29 (d, J = 2.1 Hz, 1H), 7.28-7.26 (m, 1H), 7.24 (d, J = 7.7 Hz, 2H), 6.87-6.81 (m, 1H), 1.91 (s, 3H), 1.30 (s, 9H). | 434.2 [M + H]⁺ | +++ |

TABLE 1-continued

| | ¹H NMR | MS: (ES) m/z | Chemotaxis A₂ |
|---|---|---|---|
| 1.049 | ¹H NMR (400 MHz, Chloroform-d) δ 8.08 (dd, J = 6.2, 2.7 Hz, 1H), 7.65 (ddd, J = 8.8, 4.0, 2.7 Hz, 1H), 7.44-7.29 (m, 3H), 7.28-7.20 (m, 4H), 6.81 (d, J = 9.0 Hz, 1H), 1.90 (s, 3H), 1.30 (s, 9H). | 452.2 [M + H]⁺ | +++ |
| 1.050 | ¹H NMR (400 MHz, Chloroform-d) δ 8.13-8.06 (m, 1H), 7.51 (dd, J = 8.1, 2.2 Hz, 1H), 7.42 (d, J = 8.2 Hz, 1H), 7.39-7.31 (m, 2H), 7.30-7.17 (m, 4H), 6.85-6.78 (m, 1H), 2.69 (s, 3H), 1.89 (s, 3H), 1.30 (s, 9H). | 448.2 [M + H]⁺ | +++ |
| 1.051 | ¹H NMR (400 MHz, Chloroform-d) δ 8.22-8.09 (m, 2H), 7.69 (dddd, J = 8.0, 1.8, 1.3, 0.4 Hz, 1H), 7.66-7.58 (m, 1H), 7.26-7.17 (m, 2H), 7.06 (d, J = 2.3 Hz, 1H), 6.99 (ddd, J = 8.5, 2.5, 0.6 Hz, 1H), 6.88-6.81 (m, 1H), 6.73 (d, J = 8.6 Hz, 1H), 2.76 (t, J = 6.7 Hz, 2H), 1.87 (s, 3H), 1.78 (t, J = 6.7 Hz, 2H), 1.32 (d, J = 1.5 Hz, 6H). | 462.5 [M + H]⁺ | +++ |
| 1.052 | ¹H NMR (400 MHz, Chloroform-d) δ 8.10 (d, J = 2.3 Hz, 1H), 7.52 (dd, J = 8.1, 2.3 Hz, 1H), 7.42 (dt, J = 8.0, 0.7 Hz, 1H), 7.22-7.19 (m, 2H), 7.06-7.01 (m, 1H), 6.98 (ddd, J = 8.7, 2.5, 0.7 Hz, 1H), 6.83 (dd, J = 8.9, 0.6 Hz, 1H), 6.73 (d, J = 8.5 Hz, 1H), 2.80-2.71 (m, 2H), 2.69 (s, 3H), 1.85 (s, 3H), 1.78 (t, J = 6.7 Hz, 2H), 1.32 (d, J = 1.6 Hz, 6H). | 476.2 [M + H]⁺ | +++ |

TABLE 1-continued

| Structure | ¹H NMR | MS: (ES) m/z | Chemotaxis A₂ |
|---|---|---|---|
| 1.053 | ¹H NMR (400 MHz, Chloroform-d) δ 8.39-8.13 (m, 2H), 7.65-7.50 (m, 2H), 7.30-7.25 (m, 2H), 7.05 (d, J = 2.3 Hz, 1H), 7.00-6.92 (m, 2H), 6.73 (d, J = 8.6 Hz, 1H), 2.75 (t, J = 6.8 Hz, 2H), 1.86 (s, 3H), 1.78 (t, J = 6.7 Hz, 2H), 1.43-1.08 (m, 6H). | 462.2 [M + H]⁺ | +++ |
| 1.054 | ¹H NMR (400 MHz, Chloroform-d) δ 8.08 (dd, J = 6.3, 2.7 Hz, 1H), 7.66 (ddd, J = 8.8, 4.0, 2.7 Hz, 1H), 7.32 (dd, J = 9.9, 8.8 Hz, 1H), 7.27-7.23 (m, 2H), 7.04 (d, J = 2.5 Hz, 1H), 6.97 (ddd, J = 8.7, 2.5, 0.6 Hz, 1H), 6.87-6.78 (m, 1H), 6.73 (d, J = 8.6 Hz, 1H), 2.95-2.40 (m, 2H), 1.86 (s, 3H), 1.78 (t, J = 6.7 Hz, 2H), 1.47-1.17 (m, 6H). | 480.2 [M + H]⁺ | +++ |
| 1.055 | ¹H NMR (400 MHz, Chloroform-d) δ 8.08 (d, J = 2.5 Hz, 1H), 7.63 (d, J = 8.6 Hz, 1H), 7.57 (ddd, J = 8.6, 2.5, 0.6 Hz, 1H), 7.27-7.22 (m, 2H), 7.04 (d, J = 2.4 Hz, 1H), 6.96 (ddd, J = 8.7, 2.5, 0.7 Hz, 1H), 6.86 (dt, J = 8.1, 0.6 Hz, 1H), 6.72 (d, J = 8.6 Hz, 1H), 2.75 (t, J = 6.8 Hz, 2H), 1.85 (s, 3H), 1.78 (t, J = 6.7 Hz, 2H), 1.32-1.30 (m, 6H). | 496.5 [M + H]⁺ | +++ |
| 1.056 | ¹H NMR (400 MHz, Chloroform-d) δ 8.17 (d, J = 8.4 Hz, 1H), 7.65 (d, J = 2.0 Hz, 1H), 7.49 (dd, J = 8.5, 2.1 Hz, 1H), 7.29-7.19 (m, 2H), 7.03 (d, J = 2.4 Hz, 1H), 7.00-6.93 (m, 2H), 6.73 (d, J = 8.6 Hz, 1H), 2.75 (t, J = 6.8 Hz, 2H), 1.86 (s, 3H), 1.79 (t, J = 6.7 Hz, 2H), 1.32 (s, 6H). | 496.5 [M + H]⁺ | +++ |

TABLE 1-continued

| | ¹H NMR | MS: (ES) m/z | Chemotaxis A₂ |
|---|---|---|---|
| 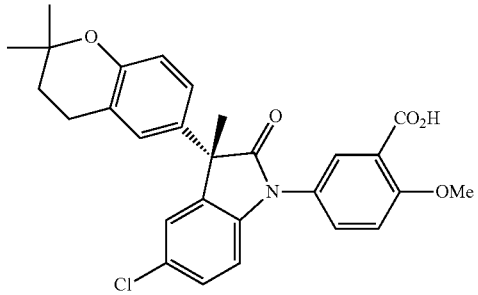    1.057 | ¹H NMR (400 MHz, Chloroform-d) δ 8.21 (d, J = 2.7 Hz, 1H), 7.66 (dd, J = 8.9, 2.7 Hz, 1H), 7.29-7.16 (m, 3 H), 7.01 (d, J = 2.4 Hz, 1H), 6.96 (dd, J = 8.6, 2.5 Hz, 1H), 6.78 (dd, J = 8.1, 0.7 Hz, 1H), 6.73 (d, J = 8.6 Hz, 1H), 4.13 (s, 3H), 2.75 (t, J = 6.7 Hz, 2H), 1.85 (s, 3H), 1.78 (t, J = 6.7 Hz, 2H), 1.32 (s, 6H). | 492.3 [M + H]⁺ | +++ |
| 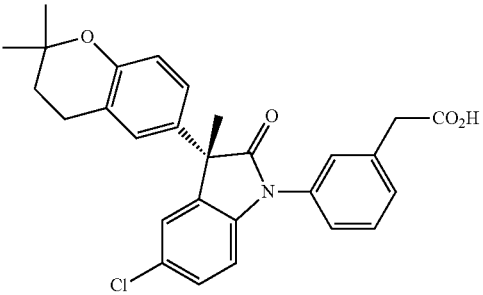    1.058 | ¹H NMR (400 MHz, Chloroform-d) δ 7.47 (t, J = 7.7 Hz, 1H), 7.41-7.30 (m, 3H), 7.22-7.16 (m, 2H), 7.05 (d, J = 2.4 Hz, 1H), 6.97 (dd, J = 8.6, 2.4 Hz, 1H), 6.85 (d, J = 8.8 Hz, 1H), 6.71 (d, J = 8.6 Hz, 1H), 3.71 (s, 2H), 2.74 (t, J = 6.8 Hz, 2H), 1.84 (s, 3H), 1.77 (t, J = 6.7 Hz, 2H), 1.31 (d, J = 1.8 Hz, 6H). | 476.6 [M + H]⁺ | +++ |
| 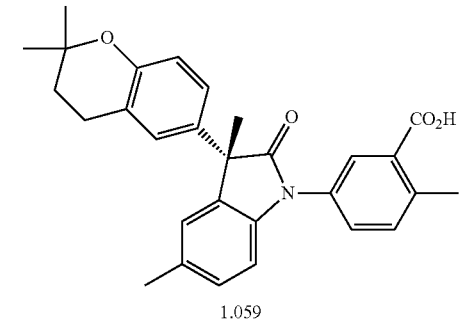    1.059 | ¹H NMR (400 MHz, Chloroform-d) δ 8.12 (d, J = 2.1 Hz, 1H), 7.54 (dd, J = 8.2, 2.3 Hz, 1H), 7.41 (d, J = 8.2 Hz, 1H), 7.12-7.02 (m, 3H), 7.00 (dd, J = 8.6, 2.4 Hz, 1H), 6.80 (d, J = 7.8 Hz, 1H), 6.71 (d, J = 8.6 Hz, 1H), 2.75 (t, J = 6.8 Hz, 2H), 2.69 (s, 3H), 2.35 (s, 3H), 1.84 (s, 3H), 1.77 (t, J = 6.7 Hz, 2H), 1.37-1.27 (m, 6H). | 456.0 [M + H]⁺ | +++ |
| 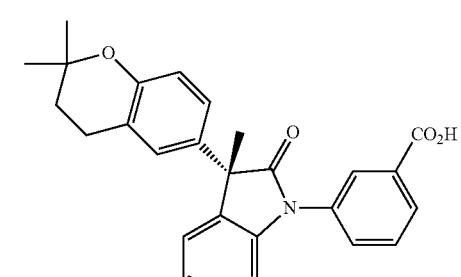    1.060 | ¹H NMR (400 MHz, Chloroform-d) δ 8.19 (t, J = 1.9 Hz, 1H), 8.13-8.06 (m, 1H), 7.76-7.69 (m, 1H), 7.61 (t, J = 7.9 Hz, 1H), 7.14-7.03 (m, 3H), 7.03-6.97 (m, 1H), 6.86-6.77 (m, 1H), 6.71 (d, J = 8.6 Hz, 1H), 2.75 (t, J = 6.8 Hz, 2H), 2.36 (d, J = 0.9 Hz, 3H), 1.85 (s, 3H), 1.78 (t, J = 6.7 Hz, 2H), 1.31 (d, J = 1.8 Hz, 6H). | 442.5 [M + H]⁺ | +++ |

TABLE 1-continued

| | ¹H NMR | MS: (ES) m/z | Chemotaxis A₂ |
|---|---|---|---|
| 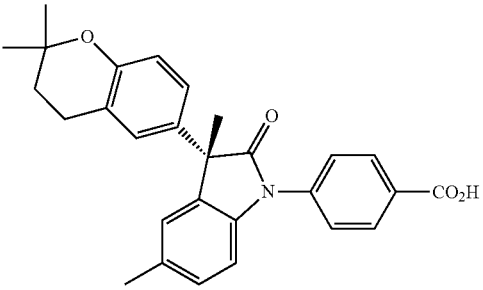 1.061 | ¹H NMR (400 MHz, Chloroform-d) δ 8.26-8.20 (m, 2H), 7.61 (d, J = 8.6 Hz, 2H), 7.08 (dt, J = 6.3, 3.4 Hz, 3H), 6.98 (dd, J = 8.6, 2.5 Hz, 1H), 6.92 (d, J = 8.5 Hz, 1H), 6.71 (d, J = 8.6 Hz, 1H), 2.75 (t, J = 6.8 Hz, 2H), 2.36 (s, 3H), 1.85 (s, 3H), 1.78 (t, J = 6.7 Hz, 2H), 1.31 (d, J = 1.7 Hz, 6H). | 442.5 [M + H]⁺ | +++ |
| 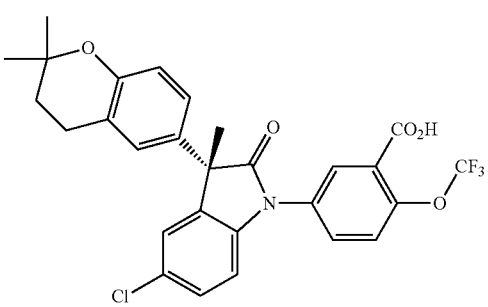 1.062 | ¹H NMR (400 MHz, Chloroform-d) δ 8.17 (d, J = 2.7 Hz, 1H), 7.73 (dd, J = 8.8, 2.7 Hz, 1H), 7.51 (dd, J = 8.8, 1.4 Hz, 1H), 7.29-7.23 (m, 2H), 7.07-7.00 (m, 1H), 6.97 (dd, J = 8.6, 2.5 Hz, 1H), 6.90 (dd, J = 8.2, 0.6 Hz, 1H), 6.73 (d, J = 8.6 Hz, 1H), 2.74 (d, J = 6.8 Hz, 2H), 1.86 (s, 3H), 1.78 (s, 2H), 1.32 (d, J = 1.0 Hz, 6H). | 546.6 [M + H]⁺ | +++ |
| 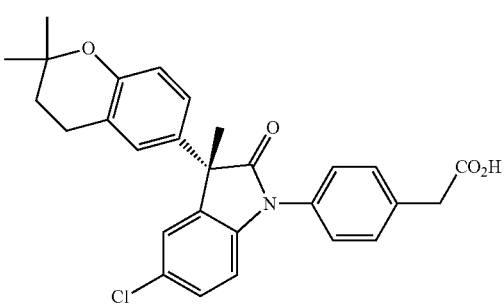 1.063 | ¹H NMR (400 MHz, Chloroform-d) δ 7.49-7.41 (m, 2H), 7.41-7.34 (m, 2H), 7.20 (dq, J = 4.3, 2.1 Hz, 2H), 7.04 (d, J = 2.3 Hz, 1H), 6.96 (ddd, J = 8.6, 1.9, 1.2 Hz, 1H), 6.85 (d, J = 8.9 Hz, 1H), 6.71 (d, J = 8.5 Hz, 1H), 3.71 (s, 2H), 2.74 (t, J = 6.7 Hz, 2H), 1.84 (s, 3H), 1.78 (t, J = 6.7 Hz, 2H), 1.31 (d, J = 1.8 Hz, 6H). | 476.2 [M + H]⁺ | +++ |
| 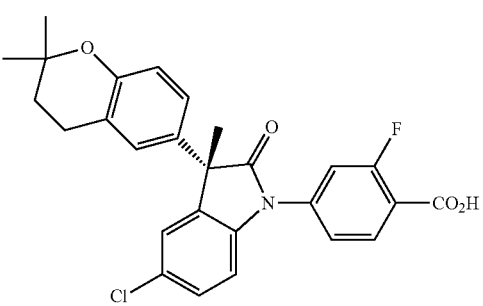 1.064 | ¹H NMR (400 MHz, Chloroform-d) δ 8.18 (s, 1H), 7.44-7.35 (m, 2H), 7.28 (dd, J = 8.4, 2.1 Hz, 1H), 7.25 (d, J = 2.1 Hz, 1H), 7.04-7.00 (m, 2H), 6.95 (dd, J = 8.6, 2.4 Hz, 1H), 6.73 (d, J = 8.6 Hz, 1H), 2.75 (t, J = 6.8 Hz, 2H), 1.86 (s, 3H), 1.78 (t, J = 6.7 Hz, 2H), 1.32 (d, J = 1.1 Hz, 6H). | 480.5 [M + H]⁺ | +++ |

| | ¹H NMR | MS: (ES) m/z | Chemotaxis A₂ |
|---|---|---|---|
| 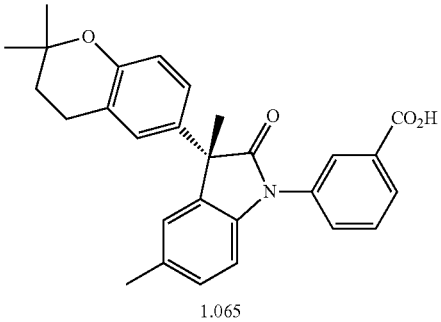 [SMILES: Cc1ccc2c(c1)[C@](C)(c1ccc3c(c1)CCC(C)(C)O3)C(=O)N2c1cccc(C(=O)O)c1] 1.065 | ¹H NMR (400 MHz, Chloroform-d) δ 8.19 (t, J = 1.8 Hz, 1H), 8.10 (dt, J = 7.8, 1.4 Hz, 1H), 7.72 (ddd, J = 7.9, 2.1, 1.2 Hz, 1H), 7.62 (t, J = 7.9 Hz, 1H), 7.11-7.04 (m, 3H), 7.01 (dd, J = 8.6, 2.5 Hz, 1H), 6.83 (d, J = 7.9 Hz, 1H), 6.71 (d, J = 8.6 Hz, 1H), 2.75 (t, J = 6.7 Hz, 2H), 2.36 (s, 3H), 1.85 (s, 3H), 1.78 (t, J = 6.7 Hz, 2H), 1.31 (d, J = 1.8 Hz, 6H). | 442.6 [M + H]⁺ | +++ |
| 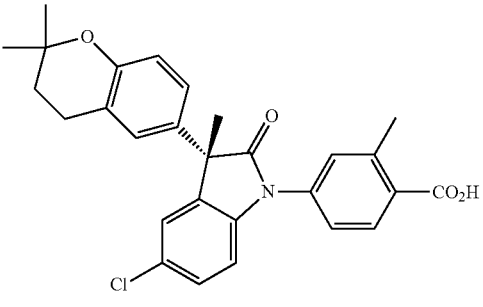 1.066 | ¹H NMR (400 MHz, Chloroform-d) δ 8.28-8.17 (m, 1H), 7.40-7.35 (m, 2H), 7.27-7.23 (m, 2H), 7.06 (d, J = 2.4 Hz, 1H), 6.97 (dd, J = 8.6, 2.5 Hz, 1H), 6.95-6.89 (m, 1H), 6.73 (d, J = 8.6 Hz, 1H), 2.76 (t, J = 6.8 Hz, 2H), 2.71 (s, 3H), 1.86 (s, 3H), 1.78 (t, J = 6.7 Hz, 2H), 1.32 (d, 7 =1.6 Hz, 6H). | 476.2 [M + H]⁺ | +++ |
| 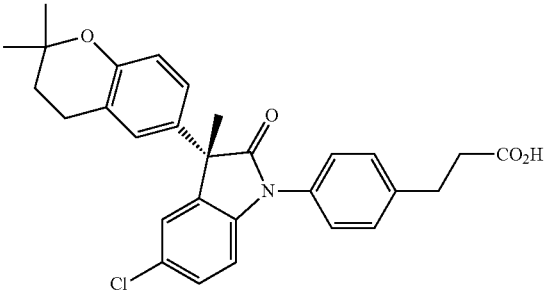 1.067 | ¹H NMR (400 MHz, Chloroform-d) δ 7.39-7.30 (m, 4H), 7.22-7.15 (m, 2H), 7.05 (d, J = 2.4 Hz, 1H), 6.99-6.94 (m, 1H), 6.85-6.80 (m, 1H), 6.71 (d, J = 8.6 Hz, 1H), 3.02 (t, J = 7.7 Hz, 2H), 2.81-2.68 (m, 4H), 1.83 (s, 3H), 1.78 (t, J = 6.7 Hz, 2H), 1.31 (d, J = 1.9 Hz, 6H). | 490.2 [M + H]⁺ | +++ |
| 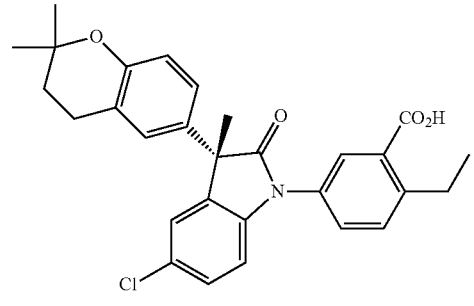 1.068 | ¹H NMR (400 MHz, CDCl₃) δ 8.05 (d, J = 2.3, Hz, 1 H), 7.56 (dd,J = 8.5, 2.3 Hz, 1 H), 7.46 (d, J = 8.2 Hz, 1 H), 7.23-7.20 (m, 2 H), 7.05 (d, J = 2.4 Hz, 1H), 6.98 (dd, J = 8.6, 2.3 Hz, 1 H) 6.85-6.83 (m, 1 H), 6.73 (d, J = 8.6 Hz, 1 H), 3.11 (q, J = 7.4 Hz, 2 H), 3.07 (bs, 1 H), 2.76 (t, J = 7.6 Hz, 2 H), 1.84 (s, 3 H), 1.79 (t, J = 6.6 Hz, 2 H), 1.31-1.25 (m, 9 H). | 490.2 [M + H]⁺ | +++ |

TABLE 1-continued

| | ¹H NMR | MS: (ES) m/z | Chemotaxis A₂ |
|---|---|---|---|
| 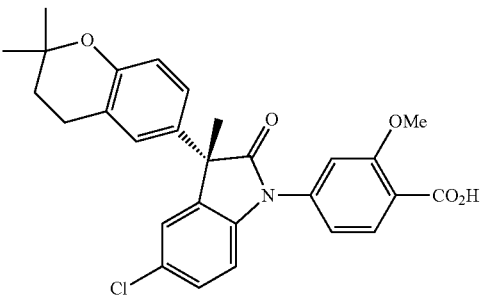<br>1.069 | ¹H NMR (400 MHz, Chloroform-d) δ 8.30 (dd, J = 8.8, 0.6 Hz, 1H), 7.31-7.19 (m, 4H), 7.07-7.02 (m, 1H), 7.00 (dt, J = 8.4, 0.5 Hz, 1H), 6.95 (ddd, J = 8.7, 2.5, 0.7 Hz, 1H), 6.73 (d, J = 8.6 Hz, 1H), 4.09 (s, 3H), 2.86-2.52 (m, 2H), 1.86 (s, 3H), 1.78 (t, J = 6.7 Hz, 2H), 1.34-1.29 (m, 6H). | 492.2 [M + H]⁺ | +++ |
| 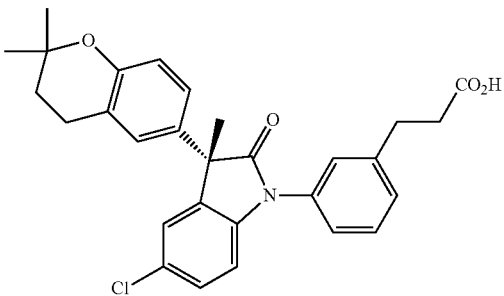<br>1.070 | ¹H NMR (400 MHz, Chloroform-d) δ 7.49-7.39 (m, 1H), 7.25 (ddd, J = 7.5, 5.3, 3.1 Hz, 3H), 7.20-7.18 (m, 1H), 7.05 (d, J = 2.4 Hz, 1H), 6.97 (dd, J = 8.6, 2.5 Hz, 1H), 6.85-6.79 (m, 1H), 6.72 (d, J = 8.6 Hz, 1H), 3.00 (t, J = 7.7 Hz, 2H), 2.73 (dt, J = 17.0, 7.2 Hz, 4H), 1.84 (s, 3H), 1.78 (t, J = 6.7 Hz, 2H), 1.31 (d, J = 1.9 Hz, 6H). | 490.2 [M + H]⁺ | +++ |
| 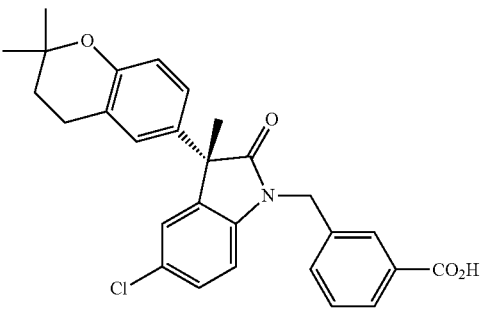<br>1.071 | ¹H NMR (400 MHz, Chloroform-d) δ 8.06-7.99 (m, 2H), 7.51-7.35 (m, 2H), 7.20-7.07 (m, 2H), 7.00-6.82 (m, 2H), 6.71 (s, 1H), 6.66 (d, J = 8.9 Hz, 1H), 5.11-4.75 (m, 2H), 2.74 (t, J = 6.7 Hz, 2H), 1.82 (s, 3H), 1.78 (t, J = 6.7 Hz, 2H), 1.31 (s, 6H). | 476.2 [M + H]⁺ | +++ |
| 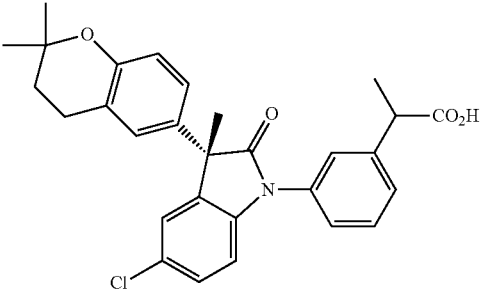<br>1.072 | ¹H NMR (400 MHz, Chloroform-d) δ 7.47 (t, J = 7.8 Hz, 1H), 7.42-7.29 (m, 3H), 7.22-7.16 (m, 2H), 7.05 (dd, J = 2.5, 1.2 Hz, 1H), 7.00-6.94 (m, 1H), 6.84 (dt, J = 8.0, 1.0 Hz, 1H), 6.72 (d, J = 8.6 Hz, 1H), 3.80 (d, J = 7.4 Hz, 1H), 2.75 (t, J = 6.7 Hz, 2H), 1.84 (d, J = 1.0 Hz, 3H), 1.78 (t, J = 6.7 Hz, 2H), 1.55 (d, J = 7.0 Hz, 3H), 1.31 (d, J = 1.8 Hz, 6H). | 490.6 [M + H]⁺ | +++ |

TABLE 1-continued

| | ¹H NMR | MS: (ES) m/z | Chemotaxis A₂ |
|---|---|---|---|
| 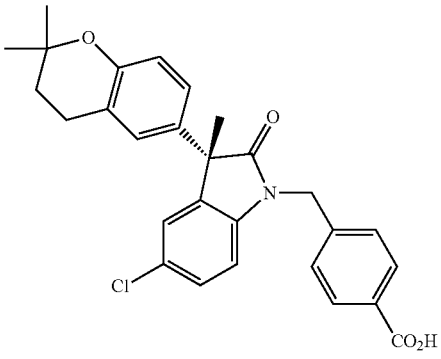  1.073 | ¹H NMR (400 MHz, Chloroform-d) δ 8.05 (d, J = 8.2 Hz, 2H), 7.34 (d, J = 8.1Hz, 2H), 7.19-7.12 (m, 2H), 6.99 (d, J = 2.4 Hz, 1H), 6.91 (dd, J = 8.6, 2.5 Hz, 1H), 6.72 (d, J = 8.5 Hz, 1H), 6.67-6.60 (m, 1H), 5.09-4.89 (m, 2H), 2.74 (t, J = 6.8 Hz, 2H), 1.81 (s, 3H), 1.78 (t, J = 6.7 Hz, 2H), 1.32 (s, 6H). | 476.2 [M + H]⁺ | +++ |
| 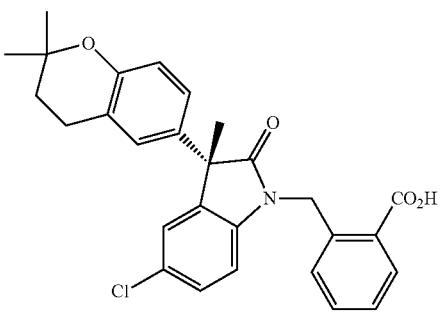  1.074 | ¹H NMR (400 MHz, Chloroform-d) δ 8.16 (dd, J = 7.8, 1.5 Hz, 1H), 7.53-7.43 (m, 1H), 7.42-7.33 (m, 1H), 7.21-7.12 (m, 2H), 7.07-6.99 (m, 2H), 6.95 (dd, J = 8.6, 2.5 Hz, 1H), 6.72 (d, J = 8.5 Hz, 1H), 6.66 (dd, J = 8.3, 0.6 Hz, 1H), 5.44 (d, J = 3.8 Hz, 2H), 2.75 (t, J = 6.7 Hz, 2H), 1.84 (s, 3H), 1.78 (t, J = 6.7 Hz, 2H), 1.32 (s, 6H). | 476.2 [M + H]⁺ | +++ |
| 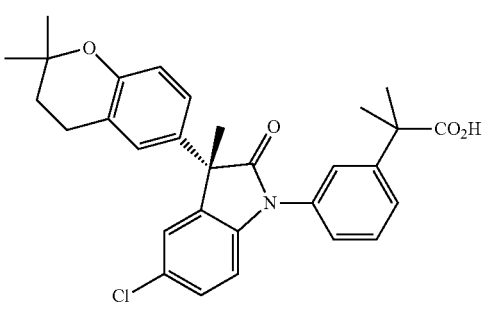  1.075 | ¹H NMR (400 MHz, Chloroform-d) δ 7.53-7.42 (m, 3H), 7.34-7.28 (m, 1H), 7.22-7.17 (m, 2H), 7.08-7.03 (m, 1H), 6.97 (dd, J = 8.6, 2.5 Hz, 1H), 6.82 (dd, J = 8.1, 0.8 Hz, 1H), 6.72 (d, J = 8.6 Hz, 1H), 2.75 (t, J = 6.8 Hz, 2H), 1.85 (s, 3H), 1.78 (t, J = 6.7 Hz, 2H), 1.63 (s, 6H), 1.32 (d, J =2.1 Hz, 6H). | 504.2 [M + H]⁺ | +++ |
| 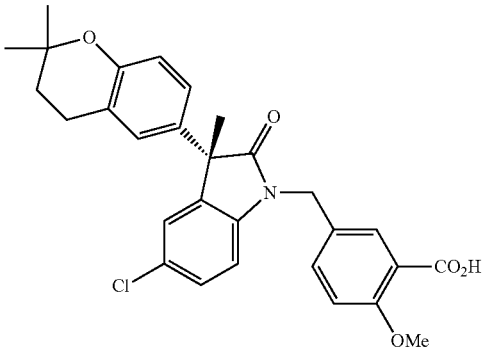  1.076 | ¹H NMR (400 MHz, Chloroform-d) δ 8.17 (d, J = 2.4 Hz, 1H), 7.45-7.37 (m, 1H), 7.20-7.10 (m, 2H), 7.03-6.96 (m, 2H), 6.90-6.83 (m, 1H), 6.76-6.63 (m, 2H), 4.98-4.82 (m, 2H), 4.06 (s, 3H), 2.75 (t, J = 6.7 Hz, 2H), 1.81-1.74 (m, 5H), 1.32 (s, 6H). | 528.2 [M + Na]⁺ | +++ |

TABLE 1-continued

| | ¹H NMR | MS: (ES) m/z | Chemotaxis A₂ |
|---|---|---|---|
| 1.077 | ¹H NMR (400 MHz, Chloroform-d) δ 8.08 (s, 1H), 8.02 (d, J = 7.7 Hz, 1H), 7.60-7.37 (m, 2H), 7.11 (s, 1H), 7.06-6.96 (m, 2H), 6.92-6.85 (m, 1H), 6.77-6.65 (m, 1H), 6.41 (t, J = 8.6 Hz, 1H), 5.87 (m, J = 7.0 Hz, 1H), 2.76 (d, J = 7.0 Hz, 2H), 1.87 (dd, J = 7.1, 4.0 Hz, 2H), 1.81-1.74 (m, 6H), 1.32 (d, J = 2.3 Hz, 6H). | 512.2 [M + Na]⁺ | +++ |
| 1.078 | ¹H NMR (400 MHz, Chloroform-d) δ 7.92 (d, J = 6.8 Hz, 1H), 7.44 (s, 1H), 7.22-7.08 (m, 3H), 6.97 (s, 1H), 6.89 (d, J = 10.7 Hz, 1H), 6.68 (dd, J = 16.5, 8.4 Hz, 2H), 5.06-4.79 (m, 2H), 2.73 (t, J = 6.7 Hz, 3H), 1.81-1.68 (m, 5H), 1.31 (s, 6H). | 516.3 [M + Na]⁺ | +++ |
| 1.079 | ¹H NMR (400 MHz, Chloroform-d) δ 7.93 (s, 1H), 7.33-7.27 (m, 1H), 7.22 (d, J = 7.0 Hz, 1H), 7.18-7.12 (m, 2H), 6.99 (d, J = 4.2 Hz, 1H), 6.92-6.86 (m, 1H), 6.72-6.64 (m, 2H), 5.03-4.78 (m, 2H), 2.74 (t, J = 6.7 Hz, 2H), 2.60 (s, 3H), 1.80 (m, 5H), 1.31 (s, 6H). | 512.3 [M + Na]⁺ | +++ |
| 1.080 | ¹H NMR (400 MHz, Chloroform-d) δ 7.92 (s, 1H), 7.25-7.13 (m, 3H), 7.00 (d, J = 4.5 Hz, 1H), 6.97-6.90 (m, 2H), 6.69 (dd, J = 17.2, 8.3 Hz, 2H), 5.35 (d, J = 5.1 Hz, 2H), 2.74 (t, J = 6.8 Hz, 2H), 2.36 (s, 3H), 1.81 (s, 3H), 1.78 (t, J = 6.7 Hz, 2H), 1.32 (s, 6H). | 490.3 [M + H]⁺ | +++ |

TABLE 1-continued

| | ¹H NMR | MS: (ES) m/z | Chemotaxis A₂ |
|---|---|---|---|
| 1.081 | ¹H NMR (400 MHz, Chloroform-d) δ 7.42 (t, J = 8.1 Hz, 1H), 7.22-7.16 (m, 2H), 7.08-7.02 (m, 2H), 7.01-6.92 (m, 3H), 6.86 (dd, J = 9.0, 0.6 Hz, 1H), 6.71 (d, J = 8.6 Hz, 1H), 4.66 (s, 2H), 2.74 (t, J = 6.7 Hz, 2H), 1.83 (s, 3H), 1.77 (t, J = 6.7 Hz, 2H), 1.31 (d, J = 1.8 Hz, 6H). | 492.5 [M + H]⁺ | +++ |
| 1.082 | ¹H NMR (400 MHz, Methanol-d₄) δ 7.77 (dd, J = 9.5, 2.8 Hz, 1H), 7.33-7.17 (m, 2H), 7.12-7.03 (m, 1H), 6.99 (d, J = 2.4 Hz, 1H), 6.94 (d, J = 8.4 Hz, 1H), 6.87-6.80 (m, 2H), 6.67 (d, J = 8.6 Hz, 1H), 5.38 (s, 2H), 2.76 (t, J = 6.6 Hz, 2H), 1.85-1.75 (m, 5H), 1.29 (d, J = 1.9 Hz, 6H). | 494.3 [M + H]⁺ | +++ |
| 1.083 | ¹H NMR (400 MHz, Methanol-d₄) δ 7.58 (d, J = 2.6 Hz, 1H), 7.24-7.19 (m, 3H), 7.04-6.97 (m, 2H), 6.97-6.90 (m, 1H), 6.82 (d, J = 8.6 Hz, 1H), 6.67 (d, J = 8.5 Hz, 1H), 5.33 (s, 2H), 3.80 (s, 3H), 2.76 (t, J = 6.8 Hz, 2H), 1.88-1.67 (m, 5H), 1.29 (d, J = 2.0 Hz, 6H). | 506.4 [M + H]⁺ | +++ |
| 1.084 | ¹H NMR (400 MHz, Chloroform-d) δ 7.32 (d, J = 8.8 Hz, 2H), 7.23-7.16 (m, 2H), 7.06-7.01 (m, 3H), 6.97-6.88 (m, 1H), 6.80-6.74 (m, 1H), 6.72 (d, J = 8.6 Hz, 1H), 4.69 (s, 2H), 2.74 (s, 2H), 1.84 (s, 3H), 1.78 (t, J = 6.7 Hz, 2H), 1.31 (d, J = 1.8 Hz, 6H). | 492.5 [M + H]⁺ | +++ |

TABLE 1-continued

| | ¹H NMR | MS: (ES) m/z | Chemotaxis A₂ |
|---|---|---|---|
| 1.085 | ¹H NMR (400 MHz, Chloroform-d) δ 7.37-7.28 (m, 4H), 7.20 (dqd, J = 4.2, 2.2, 0.6 Hz, 2H), 7.05 (d, J = 2.4 Hz, 1H), 6.96 (ddd, J = 8.8, 2.5, 0.8 Hz, 1H), 6.81 (dd, J = 8.9, 0.6 Hz, 1H), 6.72 (d, J = 8.5 Hz, 1H), 2.79-2.65 (m, 4H), 2.42 (t, J = 7.3 Hz, 2H), 2.00 (p, J = 7.4 Hz, 2H), 1.84 (s, 3H), 1.78 (t, J = 6.7 Hz, 2H), 1.32 (d, J = 2.0 Hz, 6H). | 504.6 [M + H]⁺ | +++ |
| 1.086 | ¹H NMR (400 MHz, Chloroform-d) δ 8.23 (d, J = 2.7 Hz, 1H), 7.64 (ddd, J = 8.9, 2.8, 0.6 Hz, 1H), 7.25-7.15 (m, 3H), 7.01 (d, J = 2.4 Hz, 1H), 6.96 (ddd, J = 8.7, 2.5, 0.7 Hz, 1H), 6.78 (dt, J = 8.1, 0.7 Hz, 1H), 6.73 (d, J = 8.5 Hz, 1H), 4.40 (q, J = 7.0 Hz, 2H), 2.75 (t, J = 6.7 Hz, 2H), 1.85 (s, 3H), 1.78 (t, J = 6.7 Hz, 2H), 1.61 (t, J = 7.0 Hz, 3H), 1.32 (s, 6H). | 506.4 [M + H]⁺ | +++ |
| 1.087 | ¹H NMR (400 MHz, Chloroform-d) δ 8.25 (d, J = 2.7 Hz, 1H), 7.63 (dd, J = 8.8, 2.8 Hz, 1H), 7.25-7.16 (m, 3H), 7.06-6.92 (m, 2H), 6.80 (d, J = 9.0 Hz, 1H), 6.72 (d, J = 8.5 Hz, 1H), 4.93 (p, J = 6.1 Hz, 1H), 2.75 (t, J = 6.7 Hz, 2H), 1.84 (s, 3H), 1.78 (t, J = 6.7 Hz, 2H), 1.53 (dd, J = 6.0, 1.0 Hz, 6H), 1.32 (s, 6H). | 520.4 [M + H]⁺ | +++ |
| 1.088 | ¹H NMR (400 MHz, Chloroform-d) δ 8.19-8.05 (m, 1H), 7.39 (dd, J = 8.4, 2.3 Hz, 1H), 7.23-7.16 (m, 2H), 7.03-6.96 (m, 2H), 6.92 (dd, J = 8.5, 2.5 Hz, 1H), 6.72 (d, J = 8.6 Hz, 1H), 6.65 (d, J = 8.1 Hz, 1H), 5.43-5.24 (m, 2H), 2.74 (t, J = 6.8 Hz, 2H), 2.40 (br s, 1H), 1.88-1.64 (m, 5H), 1.32 (s, 6H). | 510.3 [M + H]⁺ | +++ |

TABLE 1-continued

| | ¹H NMR | MS: (ES) m/z | Chemotaxis A₂ |
|---|---|---|---|
| 1.089 | ¹H NMR (400 MHz, Chloroform-d) δ 7.97 (d, J = 7.9 Hz, 1H), 7.24 (s, 1H), 7.18-7.13 (m, 2H), 7.10 (s, 1H), 6.98 (s, 1H), 6.91 (d, J = 8.6 Hz, 1H), 6.71 (d, J = 8.6 Hz, 1H), 6.63 (d, J = 8.8 Hz, 1H), 5.09-4.65 (m, 2H), 2.77-2.70 (m, 2H), 2.57 (d, J = 0.8 Hz, 3H), 1.87-1.61 (m, 5H), 1.32 (s, 6H). | 490.4 [M + H]⁺ | +++ |
| 1.090 | ¹H NMR (400 MHz, Chloroform-d) δ 8.05-8.00 (m, 1H), 7.19-7.10 (m, 3H), 7.06-7.02 (m, 1H), 6.97-6.92 (m, 1H), 6.82-6.79 (m, 1H), 6.74-6.64 (m, 1H), 5.38 (d, J = 21.9 Hz, 2H), 2.79-2.74 (m, 2H), 2.22 (s, 3H), 1.83 (s, 3H), 1.79-1.74 (m, 2H), 1.32 (d, J = 3.2 Hz, 6H). | 490.4 [M + H]⁺ | +++ |
| 1.091 | ¹H NMR (400 MHz, Chloroform-d) δ 7.26-7.25 (m, 1H), 7.25-7.21 (m, 1H), 7.20 (d, J = 9.1 Hz, 1H), 7.18-7.13 (m, 1H), 6.99 (d, J = 7.6 Hz, 1H), 6.91 (d, J = 8.4 Hz, 1H), 6.85 (d, J = 8.1 Hz, 2H), 6.68 (d, J = 8.1 Hz, 1H), 5.11-4.71 (m, 2H), 2.71-2.66 (m, 2H), 2.44 (s, 3H), 1.77-1.73 (m, 5H), 1.30 (s, 6H). | 512.3 [M + Na]⁺ | +++ |
| 1.092 | ¹H NMR (400 MHz, Chloroform-d) δ 7.75 (t, J = 1.6 Hz, 1H), 7.65 (dd, J = 2.5, 1.3 Hz, 1H), 7.26-7.19 (m, 3H), 7.05 (d, J = 2.5 Hz, 1H), 6.99 (dd, J = 8.6, 2.5 Hz, 1H), 6.90-6.84 (m, 1H), 6.73 (d, J = 8.6 Hz, 1H), 3.89 (s, 3H), 2.76 (t, J = 6.7 Hz, 2H), 1.86 (s, 3H), 1.78 (t, J = 6.7 Hz, 2H), 1.32 (d, J = 1.6 Hz, 6H). | 492.5 [M + H]⁺ | +++ |

TABLE 1-continued

| | | ¹H NMR | MS: (ES) m/z | Chemotaxis A₂ |
|---|---|---|---|---|
| 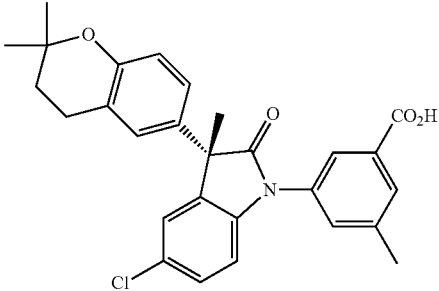 1.093 | | ¹H NMR (400 MHz, Chloroform-d) δ 7.95 (dd, J = 1.8, 0.8 Hz, 2H), 7.50 (dq, J = 2.0, 0.9 Hz, 1H), 7.22 (dt, J = 4.3, 2.4 Hz, 2H), 7.06 (d, J = 2.4 Hz, 1H), 6.99 (dd, J = 8.6, 2.4 Hz, 1H), 6.83 (d, J = 9.0 Hz, 1H), 6.73 (d, J = 8.6 Hz, 1H), 2.76 (t, J = 6.8 Hz, 2H), 2.48 (s, 3H), 1.86 (s, 3H), 1.78 (t, J = 6.7 Hz, 2H), 1.32 (d, J = 1.6 Hz, 6H). | 476.3 [M + H]⁺ | +++ |
| 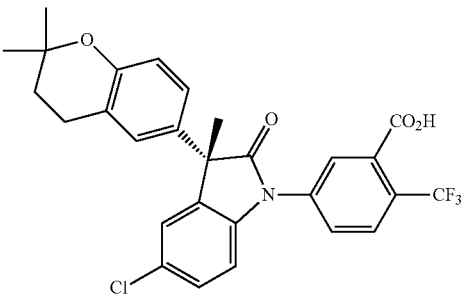 1.094 | | ¹H NMR (400 MHz, Chloroform-d) δ 8.09 (d, J = 2.1 Hz, 1H), 7.94 (d, J = 8.5 Hz, 1H), 7.79 (ddd, J = 8.5, 2.0, 0.8 Hz, 1H), 7.31-7.22 (m, 2H), 7.03 (d, J = 2.4 Hz, 1H), 7.01-6.90 (m, 2H), 6.73 (d, J = 8.6 Hz, 1H), 2.75 (t, J = 6.8 Hz, 2H), 1.87 (s, 3H), 1.78 (t, J = 6.7 Hz, 2H), 1.32 (s, 6H). | 530.3 [M + H]⁺ | +++ |
| 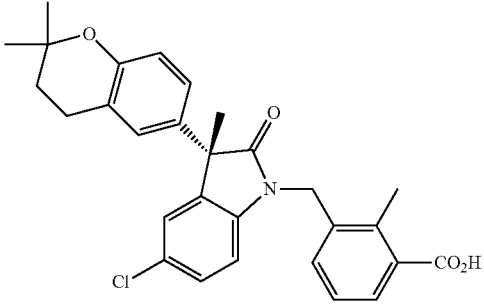 1.095 | | ¹H NMR (400 MHz, Chloroform-d) δ 7.86 (d, J = 7.7 Hz, 1H), 7.20-7.08 (m, 4H), 7.03 (d, J = 2.4 Hz, 1H), 6.94 (dd, J = 8.6, 2.5 Hz, 1H), 6.72 (d, J = 8.6 Hz, 1H), 6.54 (d, J = 8.3 Hz, 1H), 4.98 (d, J = 5.6 Hz, 2H), 2.75 (t, J = 6.8 Hz, 2H), 2.62 (s, 3H), 1.83 (s, 3H), 1.78 (t, J = 6.8 Hz, 2H), 1.32 (s, 6H). | 490.3 [M + H]⁺ | +++ |
| 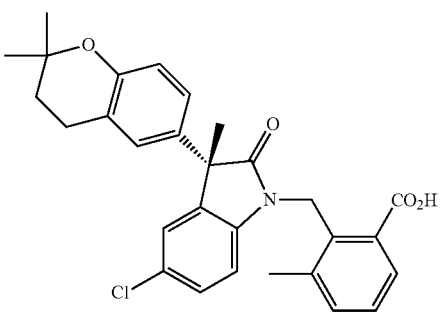 1.096 | | ¹H NMR (400 MHz, Chloroform-d) δ 7.63 (d, J = 7.2 Hz, 1H), 7.35-7.28 (m, 2H), 7.25-7.18 (m, 1H), 7.17 (dd, J = 2.0, 1.1 Hz, 1H), 6.84 (dd, J = 13.4, 5.0 Hz, 3H), 6.67 (d, J = 8.5 Hz, 1H), 5.11 (s, 2H), 2.74-2.47 (m, 2H), 2.18 (d, J = 1.0 Hz, 3H), 1.76 (t, J = 6.6 Hz, 2H), 1.72 (d, J = 1.1 Hz, 3H), 1.30 (s, 6H). | 490.4 [M + H]⁺ | +++ |

TABLE 1-continued

| | ¹H NMR | MS: (ES) m/z | Chemotaxis A₂ |
|---|---|---|---|
| 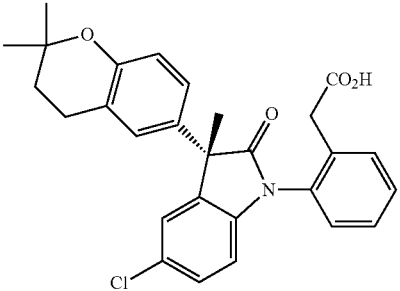<br>1.097 | ¹H NMR (400 MHz, Chloroform-d) δ 7.48-7.41 (m, 3H), 7.30-7.23 (m, 2H), 7.20-7.12 (m, 2H), 7.03 (dd, J = 15.9, 2.5 Hz, 1H), 6.94 (ddd, J = 12.7, 8.5, 2.5 Hz, 1H), 6.70 (dd, J = 8.6, 7.0 Hz, 1H), 6.55 (dd, J = 26.1, 8.3 Hz, 1H), 3.74-3.30 (m, 2H), 2.72 (q, J = 6.7 Hz, 2H), 1.84 (s, 3H), 1.77 (q, J = 6.8 Hz, 2H), 1.31 (d, J = 2.0 Hz, 6H). | 476.3 [M + H]⁺ | +++ |
| 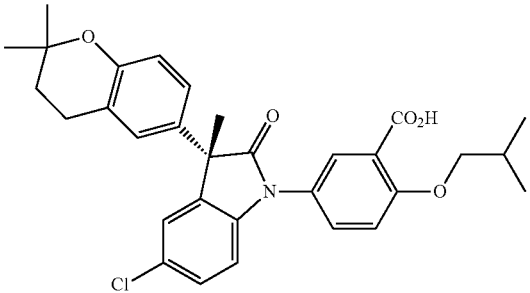<br>1.098 | ¹H NMR (400 MHz, Chloroform-d) δ 8.23 (d, J = 2.7 Hz, 1H), 7.63 (dd, J = 8.8, 2.7 Hz, 1H), 7.23-7.17 (m, 3H), 7.02 (d, J = 2.4 Hz, 1H), 6.97 (dd, J = 8.6, 2.4 Hz, 1H), 6.81-6.75 (m, 1H), 6.73 (d, J = 8.5 Hz, 1H), 4.08 (d, J = 6.4 Hz, 2H), 2.75 (t, J = 6.7 Hz, 2H), 2.27 (dt, J = 13.3, 6.7 Hz, 1H), 1.84 (s, 3H), 1.78 (t, J = 6.7 Hz, 2H), 1.32 (s, 6H), 1.28 (s, 2H), 1.12 (d, J = 6.7 Hz, 6H). | 534.4 [M + H]⁺ | +++ |
| 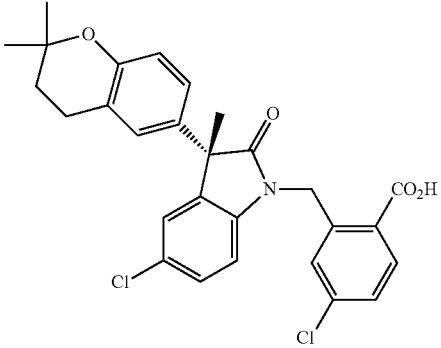<br>1.099 | ¹H NMR (400 MHz, Chloroform-d) δ 8.09 (d, J = 8.4 Hz, 1H), 7.34 (dd, J = 8.4, 2.1 Hz, 1H), 7.24-7.16 (m, 2H), 7.04-6.89 (m, 3H), 6.75 (d, J = 8.5 Hz, 1H), 6.65 (d, J = 9.1 Hz, 1H), 5.45 (d, J = 17.9 Hz, 1H), 5.32 (d, J = 17.9 Hz, 1H), 2.75 (t, J = 6.7 Hz, 2H), 1.84 (s, 3H), 1.78 (t, J = 6.7 Hz, 2H), 1.32 (d, J = 1.4 Hz, 6H). | 532.3 [M + Na]⁺ | +++ |
| 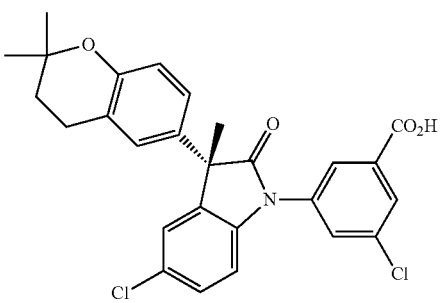<br>1.100 | ¹H NMR (400 MHz, Chloroform-d) δ 8.08 (dt, J = 12.0, 1.6 Hz, 2H), 7.71 (t, J = 1.9 Hz, 1H), 7.28-7.26 (m, 1H), 7.24 (t, J = 1.6 Hz, 1H), 7.04 (d, J = 2.4 Hz, 1H), 6.97 (dd, J = 8.6, 2.5 Hz, 1H), 6.88 (d, J = 8.2 Hz, 1H), 6.73 (d, J = 8.5 Hz, 1H), 2.76 (t, J = 6.7 Hz, 2H), 1.86 (s, 3H), 1.78 (t, J = 6.7 Hz, 2H), 1.32 (d, J = 1.2 Hz, 6H). | 496.3 [M + H]⁺ | +++ |

TABLE 1-continued

| | ¹H NMR | MS: (ES) m/z | Chemotaxis A₂ |
|---|---|---|---|
| 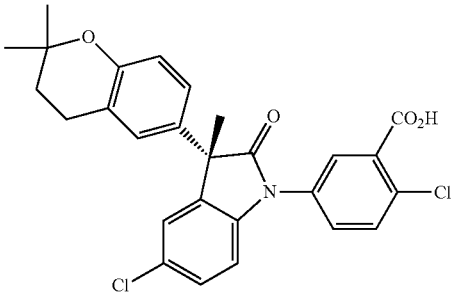 1.101 | ¹H NMR (400 MHz, Chloroform-d) δ 7.37 (s, 1H), 7.28-7.27 (m, 1H), 7.24-7.21 (m, 1H), 7.16 (d, J = 2.1 Hz, 1H), 7.05 (d, J = 7.7 Hz, 1H), 6.92 (d, J = 2.4 Hz, 1H), 6.86 (d, J = 8.4 Hz, 2H), 6.69 (d, J = 8.6 Hz, 1H), 4.96 (d, J = 2.0 Hz, 2H), 2.88-2.53 (m, 2H), 1.79-1.66 (m, 5H), 1.31 (s, 6H). | 532.3 [M + Na]⁺ | +++ |
| 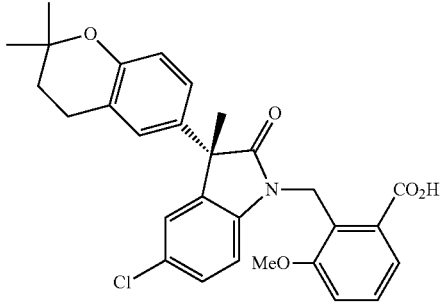 1.102 | ¹H NMR (400 MHz, Chloroform-d) δ 7.42-7.31 (m, 2H), 7.31-7.27 (m, 1H), 7.18 (d, J = 8.5 Hz, 1H), 7.10 (d, J = 2.1 Hz, 1H), 6.94 (d, J = 8.1 Hz, 1H), 6.74 (d, J = 2.4 Hz, 1H), 6.69 (dd, J = 8.6, 2.5 Hz, 1H), 6.60 (d, J = 8.6 Hz, 1H), 4.96 (d, J = 3.4 Hz, 2H), 3.58 (s, 3H), 2.64 (q, J = 6.5 Hz, 2H), 1.73 (t, J = 6.7 Hz, 2H), 1.68 (s, 3H), 1.28 (s, 6H). | 506.3 [M + H]⁺ | ++ |
| 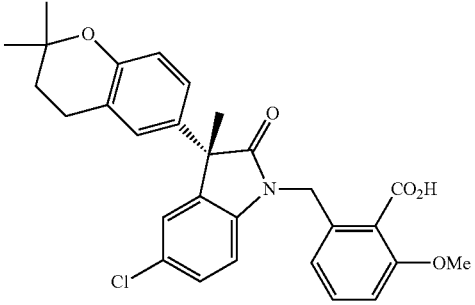 1.103 | ¹H NMR (400 MHz, Chloroform-d) δ 7.33 (t, J = 8.2 Hz, 2H), 7.21-7.13 (m, 2H), 7.03-6.83 (m, 2H), 6.76-6.65 (m, 3H), 5.22 (s, 2H), 4.00 (s, 3H), 2.73 (t, J = 6.8 Hz, 2H), 1.80-1.73 (m, 5H), 1.31 (s, 6H). | 506.3 [M + H]⁺ | +++ |
| 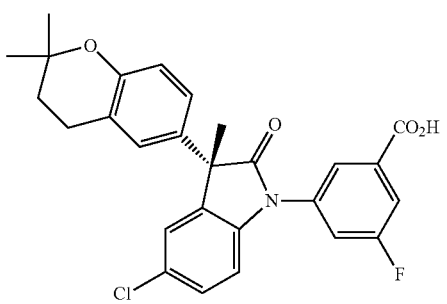 1.104 | ¹H NMR (400 MHz, Chloroform-d) δ 7.99 (t, J = 1.6 Hz, 1H), 7.81 (ddd, J = 8.4, 2.5, 1.4 Hz, 1H), 7.48 (ddd, J = 8.8, 2.4, 1.8 Hz, 1H), 7.28-7.23 (m, 2H), 7.03 (dd, J = 2.4, 1.1 Hz, 1H), 6.97 (dd, J = 8.6, 2.5 Hz, 1H), 6.92 (dd, J = 8.3, 0.5 Hz, 1H), 6.73 (d, J = 8.5 Hz, 1H), 2.76 (t, J = 6.8 Hz, 2H), 1.86 (s, 3H), 1.79 (t, J = 6.7 Hz, 2H), 1.35-1.16 (m, 6H). | 480.3 [M + H]⁺ | +++ |

TABLE 1-continued

| | ¹H NMR | MS: (ES) m/z | Chemotaxis A₂ |
|---|---|---|---|
| 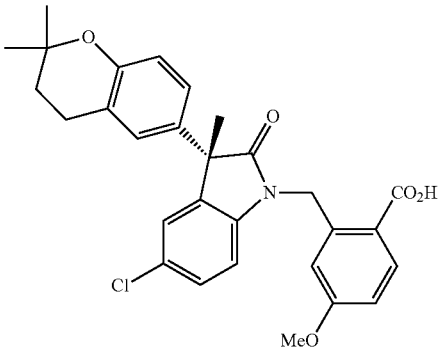 1.105 | ¹H NMR (400 MHz, Chloroform-d) δ 8.13 (d, J = 8.7 Hz, 1H), 7.22-7.15 (m, 2H), 7.05 (s, 1H), 6.97 (d, J = 8.6 Hz, 1H), 6.81 (dd, J = 8.7, 2.7 Hz, 1H), 6.69 (dd, J = 13.3, 8.4 Hz, 2H), 6.49 (d, J = 2.6 Hz, 1H), 5.58-5.08 (m, 2H), 3.59 (s, 3H), 2.74 (t, J = 6.8 Hz, 2H), 1.83 (s, 3H), 1.78 (t, J = 6.7 Hz, 2H), 1.32 (d, J = 1.6 Hz, 6H). | 506.3 [M + H]⁺ | +++ |
| 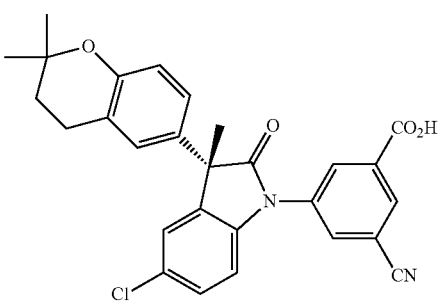 1.106 | ¹H NMR (400 MHz, Chloroform-d) δ 8.49-8.29 (m, 2H), 8.04 (dd, J = 2.1, 1.5 Hz, 1H), 7.31-7.27 (m, 2H), 7.04-6.94 (m, 2H), 6.92-6.71 (m, 2H), 2.76 (t, J = 6.8 Hz, 2H), 1.88 (s, 3H), 1.79 (t, J = 6.7 Hz, 2H), 1.32 (s, 6H). | 487.3 [M + H]⁺ | ++ |
| 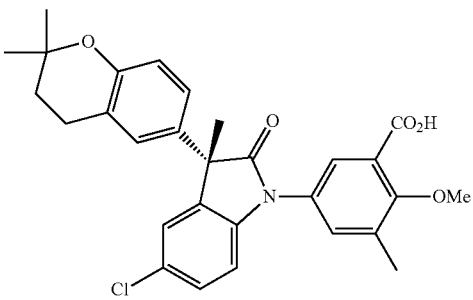 1.107 | 1H NMR (400 MHz, Chloroform-d) δ 8.01-7.96 (m, 1H), 7.55-7.48 (m, 1H), 7.24-7.20 (m, 2H), 7.05-7.00 (m, 1H), 7.01-6.92 (m, 1H), 6.85-6.78 (m, 1H), 6.73 (d, J = 8.5 Hz, 1H), 3.96 (d, J = 0.7 Hz, 3H), 2.75 (dd, J = 7.2, 6.2 Hz, 2H), 2.41 (t, J = 0.7 Hz, 3H), 1.84 (s, 3H), 1.78 (t, J = 6.7 Hz, 2H), 1.32 (d, J = 0.7 Hz, 6H). | 506.3 [M + H]⁺ | +++ |
| 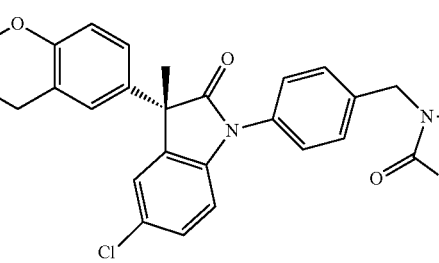 1.108 | ¹H NMR (400 MHz, chloroform-d) δ 7.58-7.51 (m, 2H), 7.47-7.41 (m, 2H), 7.22-7.16 (m, 2H), 7.03 (d, J = 2.4 Hz, 1H), 6.96 (dd, J = 8.6, 2.5 Hz, 1H), 6.85-6.80 (m, 1H), 6.70 (d, J = 8.6 Hz, 1H), 5.16 (s, 2H), 2.73 (t, J = 6.7 Hz, 2H), 1.83 (s,3H), 1.77 (t, J = 6.7 Hz, 2H), 1.30 (d, J = 2.0 Hz, 6H) | 516.5 | +++ |

TABLE 1-continued

| | ¹H NMR | MS: (ES) m/z | Chemotaxis A₂ |
|---|---|---|---|
| 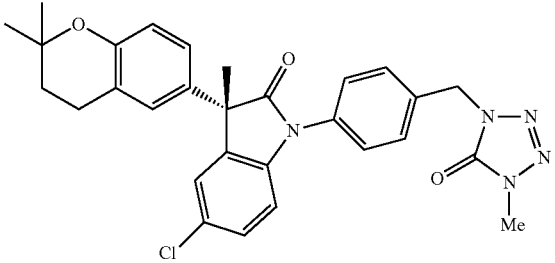<br>1.109 | ¹H NMR (400 MHz, chloroform-d) δ 7.58-7.52 (m, 2H), 7.44-7.39 (m, 2H), 7.21-7.16 (m, 2H), 7.03 (d, J = 2.4 Hz, 1H), 6.98-6.93 (m, 1H), 6.85-6.80 (m, 1H), 6.70 (d, J = 8.6 Hz, 1H), 5.13 (s, 2H), 3.61 (s, 3H), 2.73 (t, J = 6.7 Hz, 2H), 1.82 (s, 3H), 1.76 (t, J = 6.7 Hz, 2H), 1.30 (d, J = 1.8 Hz, 6H). | 530.5 | +++ |

+, 20000 nM ≥ A₂ ≥ 500 nM;
++, 500 nM > A₂ ≥ 100 nM;
+++, 100 nM > A₂.

Biological Examples

Measuring Efficacy of Chemokine Modulators

Examples of In Vitro Assays—Reagents

MOLT-4 cells were obtained from the American Type Culture Collection (Manassas, Va.) and cultured in RPMI tissue culture medium supplemented with 10% fetal calf serum (FCS) in a humidified 5% CO2 incubator at 37° C. Recombinant human chemokine proteins TECK was obtained from R&D Systems (Minneapolis, Minn.). ChemoTX™ chemotaxis microchambers were purchased from Neuro Probe (Gaithersburg, Md.). CyQUANT™ cell proliferation kits were purchased from Molecular Probes (Eugene, Oreg.). Calcium indicator dye Fluo-4 AM was purchased from Molecular Devices (Mountain View, Calif.).

In Vitro Assays

A variety of assays can be used to evaluate the compounds provided herein, including signaling assays, chemotaxis (migration assays), ligand binding assays, and other assays of cellular response. Chemokine receptor signaling assays can be used to measure the ability of a compound, such as a potential CCR(9) antagonist, to block CCR(9) ligand- (e.g. TECK)-induced signaling. Blocking such signaling can be useful in treating various diseases such as inflammatory bowel diseases, an allergic disease, psoriasis, atopic dermatitis, asthma, fibrotic diseases, graft rejection, immune mediated food allergies, autoimmune diseases, Celiac disease, rheumatoid arthritis, thymoma, thymic carcinoma, leukemia, solid tumor, acute lymphocytic leukemia, melanoma, primary sclerosing cholangitis, hepatitis or post-operative ileus.

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. A variety of chemotaxis assays are known in the art, and any suitable assay can be used to evaluate the compounds of the present disclosure. Examples of suitable assays include those described in PCT/US97/15915; Springer et al., WO 94/20142; Berman et al., Immunol. Invest., 17:625-677 (1988); and Kavanaugh et al., J. Immunol., 146:4149-4156 (1991)).

Evaluation of a Test Modulator in a Serum Chemotaxis Assay

A serum chemotaxis assay was used to determine the efficacy of potential receptor antagonists at blocking the migration mediated through chemokine receptors, such as CCR(9). This assay was performed using the ChemoTX® microchamber system with a 5-μm pore-sized polycarbonate membrane. MOLT-4 cells were collected by centrifugation at 400×g at room temperature, then suspended at 50 million/ml in human serum, containing 50 mM HEPES (final pH of 7.2). The compound being tested or an equivalent volume of its solvent (DMSO) was then added to the cell/serum mixture at a final DMSO concentration of 0.125% (v/v), and this mixture was then incubated together at 37° C. for one hour. Separately, recombinant human TECK was diluted with chemotaxis buffer (HBSS+0.1% BSA), generally spanning a range from 0.1 nM to 500 nM, after which 29 μl of diluted chemokine was placed in the lower wells of the ChemoTX® plate. The 5-μm (pore size) polycarbonate membrane was placed onto the plate, and 20 μL of the cell/compound mixture was transferred onto each well of the membrane. The plates were incubated at 37° C. for 90 minutes, after which the polycarbonate membranes were removed and 5 μl of the DNA-intercalating agent CyQUANT (Invitrogen, Carlsbad, Calif.) was added to the lower wells. The amount of fluorescence, corresponding to the number of migrated cells, was measured using a Spectrafluor Plus plate reader (TECAN, San Jose, Calif.).

The A₂ values were calculated from the following equation, comparing the efficacy of the test compound with that of the DMSO-only control at equi-active chemokine levels:

$$Log(A_2)=log[drug(M)]-log\ [(A'/A)-1]$$

where A reflects the potency of the agonist in the absence of antagonist and A' reflects the potency of the agonist in the presence of antagonist at a given concentration of drug ([drug(M)]).

In Vivo Efficacy Models for Human IBD

T cell infiltration into the small intestine and colon have been linked to the pathogenesis of human inflammatory bowel diseases which include Coeliac disease, Crohn's disease and ulcerative colitis. Blocking trafficking of relevant T cell populations to the intestine is believed to be an effective approach to treat human IBD. CCR(9) is expressed on gut-homing T cells in peripheral blood, elevated in patients with small bowel inflammation such as Crohn's disease and Coeliac disease. CCR(9) ligand TECK is expressed in the small intestine. It is thus believed that this ligand-receptor pair plays a role in IBD development by mediating migration of T cells to the intestine. Several animal models exist and can be used for evaluating compounds of interest, such as potential CCR(9) antagonists, for an ability to affect such T cell migration and/or condition or disease, which might allow efficacy predictions of antagonists in humans.

Animal Models with Pathology Similar to Human Ulcerative Colitis

A murine model described by Panwala and coworkers (Panwala et al., J Immunol., 161(10):5733-44 (1998)) involves genetic deletion of the murine multi-drug resistant gene (MDR). MDR knockout mice (MDR−/−) are susceptible to developing a severe, spontaneous intestinal inflammation when maintained under specific pathogen-free facility conditions. The intestinal inflammation seen in MDR−/− mice has a pathology similar to that of human inflammatory bowel disease (IBD) and is defined by Th1 type T cells infiltration into the lamina propria of the large intestine.

Another murine model was described by Davidson et al., J Exp Med., 184(1):241-51(1986). In this model, the murine IL-10 gene was deleted and mice rendered deficient in the production of interleukin 10 (IL-10−/−). These mice develop a chronic inflammatory bowel disease (IBD) that predominates in the colon and shares histopathological features with human IBD.

Another murine model for IBD has been described by Powrie et al., Int. Immunol., 5(11):1461-71 (1993), in which a subset of CD4+ T cells (called CD45RB(high)) from immunocompetent mice are purified and adoptively transferred into immunodeficient mice (such as C.B-17 scid mice). The animal restored with the CD45RBhighCD4+ T cell population developed a lethal wasting disease with severe mononuclear cell infiltrates in the colon, pathologically similar with human IBD.

The TNF ARE(−/−) Model.

The role of TNF in Crohn's disease in human has been demonstrated more recently by success of treatment using anti-TNF alpha antibody by Targan et al., N. Engl. J Med., 337(15):1029-35 (1997). Mice with aberrant production of TNF-alpha due to genetic alteration in the TNF gene (ARE−/−) develop Crohn's-like inflammatory bowel diseases (see Kontoyiannis et al., Immunity, 10(3):387-98 (1999)).

Examples of In Vivo Efficacy Assays

Evaluation of a Test Modulator in a CCR(9) Dependent T Cell Trafficking Model

Single cell suspensions were prepared from spleens and lymph nodes of OT-I Tg CD45.1 mice. $15 \times 10^6$ total cells (about $3 \times 10^6$ CD8 T cells) were injected into sex-matched congenic CD45.2 C57BL/6n mice (8-10 weeks old). 24 hours later, animals were immunized via oral gavage with 25 mg Ovalbumin protein (Sigma-Aldrich, St. Louis, Mo.)+ 10 ug Cholera Toxin (Calbiochem, San Diego, Calif.). CCR(9) antagonist compound 1.063 (Table 1) was administered prior to oral ovalbumin in a time frame dictated by their mouse pharmacokinetics and dosed throughout. Five days post immunization, animals were euthanized, and small intestines were harvested. Peyer's patches were removed and, after flushing with PBS, the gut was opened on a wet square of Optima fabric (Allegiance Healthcare). The mucosa was scraped with a scalpel and then dissociated by stirring in 50 ml of medium containing 10% newborn calf serum and DTT (1 mM) for 15 min at room temperature. After centrifugation, pellets were resuspended in PBS containing 10% newborn calf serum, vortexed for 3 min, and rapidly passed through a glass wool column (1.6 g packed in a 20-ml syringe; Fisher Scientific). IEL were further purified on a Ficoll-Paque gradient and stained with mAbs for flow cytometry analysis. Transferred OT-1 Tg CD45.1 T cells were detected and quantified by flow cytometry. In this model treatment with a compound of the disclosure resulted in a significant reduction in the frequency of OT-1 Tg CD45.1 T cells that traffic to the small intestine in response to antigen.

Evaluation of a Test Modulator in a Model of Inhibition of HIV Spread

In the bone marrow/liver/thymus, or "BLT" mouse, non-obese diabetic (NOD)/SCID mice (which lack endogenous T and B cells) are surgically implanted with fetal thymic and liver organoids, as in the SCID-hu system. The mice are then sub-lethally irradiated and transplanted with autologous $CD34^+$ stem cells obtained from fetal liver which take up residence in the murine bone marrow, effectively receiving a human bone marrow transplant and resulting in a range of human cells in peripheral blood, including mature T and B lymphocytes, monocytes, macrophages, and dendritic cells, all of which show extensive infiltration of organs and tissues including liver, lung, and gastrointestinal tract. Following transplantation, a compound of the disclosure is administered to transplanted mice to inhibit the trafficking of human cells to the gastrointestinal tract, a major source of T cell/HIV interaction. Compound efficacy is measured as a reduction in blood viral load by standard techniques.

Evaluation of a Test Modulator in a Model of Arthritis

A 17-day study of type II collagen-induced arthritis is conducted to evaluate the effects of a modulator on arthritis-induced clinical ankle swelling. Rat collagen-induced arthritis is an experimental model of polyarthritis that has been widely used for preclinical testing of numerous anti-arthritic agents (see Trentham et al., J. Exp. Med. 146(3):857-868 (1977), Bendele et al., Toxicologic Pathol. 27:134-142 (1999), Bendele et al., Arthritis. Rheum. 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17-day study. The test modulator is dosed daily by sub-cutaneous injection from day 9 to day 17 at a dose of 100 mg/kg and a volume of 1 mL/kg in the following vehicle (24.5 Cremaphore EL, 24.5% common oil, 1% Benzylalcohol and 50% Distilled water). Caliper measurements of the ankle joint diameter are taken daily, and reducing joint swelling is taken as a measure of efficacy.

Evaluation of a Test Modulator in a Mouse Model of Asthma

This example describes a procedure to evaluate the efficacy of antagonists for treatment of asthma. An animal model of asthma can be induced by sensitizing rodents to an experimental antigen (e.g. OVA) by standard immunization, and subsequently introducing that same antigen into the rodents lung by aerosolization. Three series of rodent groups, comprising 10 rodents per goup, are actively sensitized on Day 0 by a single i.p. injection with 100 ug OVA in phosphate-buffered saline (PBS), along with an adjuvant e.g. aluminum hydroxide. At 11 days after sensitization, the animals are placed in a Plexiglas chamber and challenged with aerosolized OVA (1%) for 30 minutes using the ultrasonic nebulizer (De Vilbliss). One series of mice additionally receives PBS and Tween 0.5% i.p. at the initial sensitization, and at different dosing schedules thereafter, up until the aerosolized OVA challenge. A second series consists of groups of mice receiving different doses of the CCR4 antagonist given either intraperitoneally, intra-venously, sub-cutaneously, intra-muscularly, orally, or via any other mode of administration at the initial sensitization, and at different dosing schedules thereafter, up until the aerosolized OVA challenge. A third series of mice, serving as positive control, consists of groups treated with either mouse IL-10 i.p., anti-IL4 antibodies i.p., or anti-IL5 antibodies i.p. at the initial sensitization, and at different dosing schedules thereafter, up until the aerosolized OVA challenge. Animals are subsequently analyzed at different time points after the aerosolized OVA challenge for pulmonary function, cellular infiltrates in bronchoalveolar lavage (BAL), histological examination of lungs, and measurement of serum OVA specific IgE titers.

It is therefore intended that the foregoing detailed description be regarded as illustrative rather than limiting, and that it be understood that it is the following claims, including all equivalents, that are intended to define the spirit and scope of this disclosure.

What is claimed is:
1. A compound having formula (I):

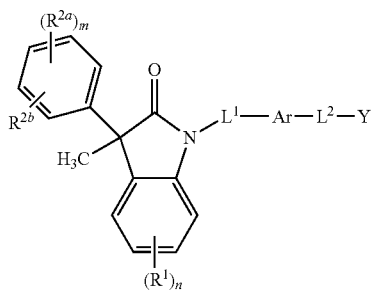

(I)

or a pharmaceutically acceptable salt thereof, wherein
Ar is a 5- to 10-membered aromatic or heteroaromatic ring, optionally substituted with from one to three $R^3$;
$L^1$ is selected from the group consisting of a bond, $C_{1-6}$ alkylene, and $C_{1-6}$ heteroalkylene,
$L^2$ is selected from the group consisting of a bond, $C_{1-6}$ alkylene, and $C_{1-6}$ heteroalkylene,
Y is $CO_2H$ or a carboxylic acid bioisostere;
each $R^1$ and each $R^{2a}$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl, wherein the alkyl, cycloalkyl and alkenyl portions are optionally substituted with from one to three members selected from fluoro, OH, CN, $C_{1-3}$ alkyl, $C_{1-3}$ haloalkyl, and $C_{1-3}$ alkoxy;
$R^{2b}$ is selected from the group consisting of H, halogen, cyano, $C_{1-6}$ alkyl, $C_{1-6}$ alkoxy, $C_{3-6}$ cycloalkyl, and $C_{2-6}$ alkenyl, wherein the alkyl, cycloalkyl and alkenyl portions are optionally substituted with from one to three members selected from fluoro, CN, $C_{1-3}$ alkyl, $C_{1-3}$ haloalkyl, and $C_{1-3}$ alkoxy;

or optionally one $R^{2a}$ and $R^{2b}$ when on adjacent vertices of a phenyl ring, may be joined together to form a 5- or 6-membered heterocycloalkyl ring having one or two ring vertices independently selected from O, N and S, wherein said heterocycloalkyl ring is optionally substituted with from one to three members selected from fluoro and $C_{1-3}$ alkyl;
each $R^3$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl;
the subscript m is an integer of from 0 to 4; and
the subscript n is an integer of from 0 to 3.

2. The compound of claim 1, having formula (I'):

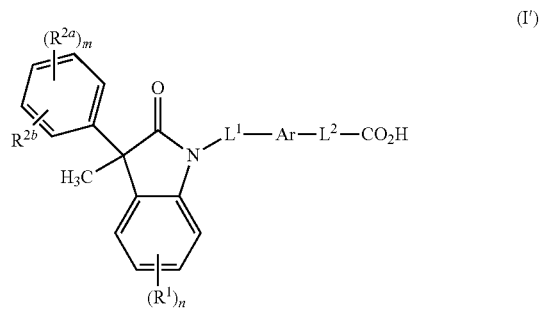

(I')

or a pharmaceutically acceptable salt thereof, wherein
Ar is a 5- to 10-membered aromatic or heteroaromatic ring, optionally substituted with from one to three $R^3$;
$L^1$ is selected from the group consisting of a bond, $C_{1-6}$ alkylene, and $C_{1-6}$ heteroalkylene,
$L^2$ is selected from the group consisting of a bond, $C_{1-6}$ alkylene, and $C_{1-6}$ heteroalkylene,
each $R^1$ and each $R^{2a}$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl, wherein the alkyl, cycloalkyl and alkenyl portions are optionally substituted with from one to three members selected from fluoro, CN, $C_{1-3}$ alkyl, $C_{1-3}$ haloalkyl, and $C_{1-3}$ alkoxy;
$R^{2b}$ is selected from the group consisting of H, halogen, cyano, $C_{1-6}$ alkyl, $C_{1-6}$ alkoxy, $C_{3-6}$ cycloalkyl, and $C_{2-6}$ alkenyl, wherein the alkyl, cycloalkyl and alkenyl portions are optionally substituted with from one to three members selected from fluoro, CN, $C_{1-3}$ alkyl, $C_{1-3}$ haloalkyl, and $C_{1-3}$ alkoxy;
or optionally one $R^{2a}$ and $R^{2b}$ when on adjacent vertices of a phenyl ring, may be joined together to form a 5- or 6-membered heterocycloalkyl ring having one or two ring vertices independently selected from O, N and S, wherein said heterocycloalkyl ring is optionally substituted with from one to three members selected from fluoro and $C_{1-3}$ alkyl;
each $R^3$ is independently selected from the group consisting of halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, and $C_{2-6}$ alkenyl;
the subscript m is an integer of from 0 to 4; and
the subscript n is an integer of from 0 to 3.

3. A compound of claim 1, wherein Y is selected from the group consisting of:

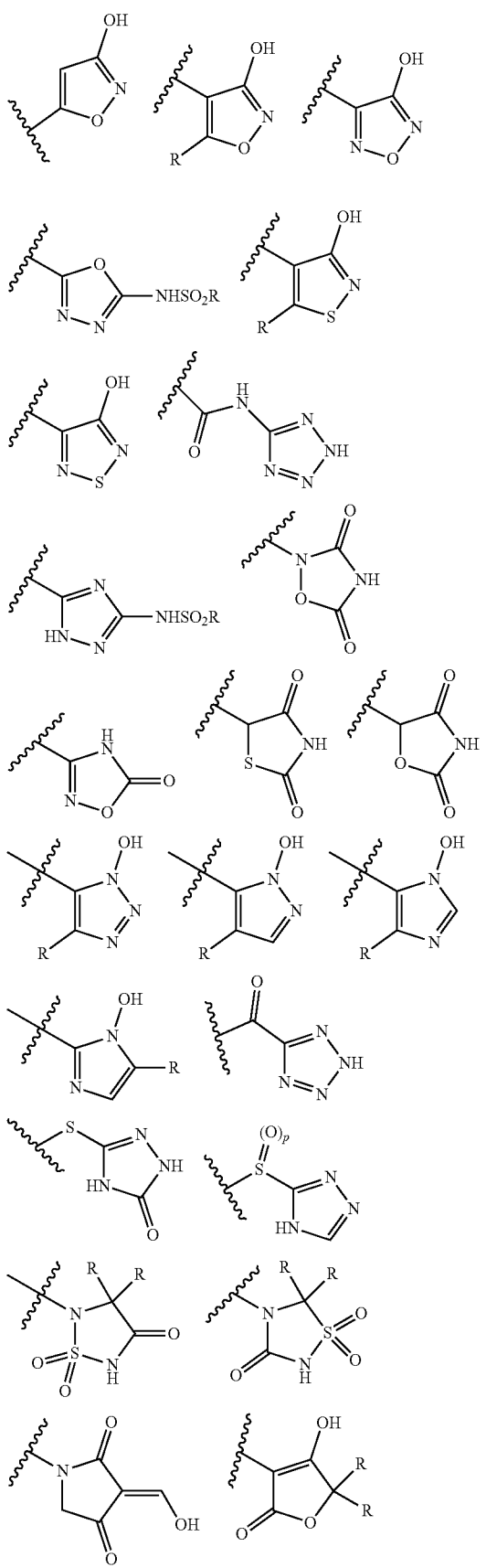

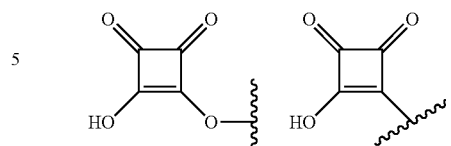

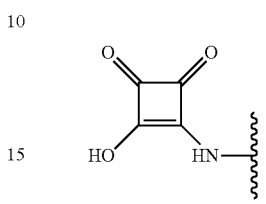

tetrazolyl and tetrazolonyl, wherein the tetrazolyl or tetrazolonyl is optionally substituted with R, wherein p is 0, 1 or 2 and wherein each R group is independently selected from the group consisting of H, $C_1$-$C_6$ alkyl, $C_1$-$C_6$ haloalkyl, $C_1$-$C_6$ hydroxyalkyl, $C_1$-$C_6$ alkoxy, or $C_1$-$C_4$ alkyl-O—$C_1$-$C_4$ alkyl.

4. A compound of claim 1, wherein Y is selected from the group consisting of: tetrazolyl and tetrazolonyl, wherein the tetrazolyl or tetrazolonyl is optionally substituted with $C_{1-6}$ alkyl, $C_{1-6}$ haloalkyl, $C_{1-6}$ hydroxyalkyl, —$C_{1-6}$ alkoxy or $C_{1-4}$alkyl-O—$C_{1-4}$alkyl.

5. A compound of claim 1 having the formula selected from the group consisting of:

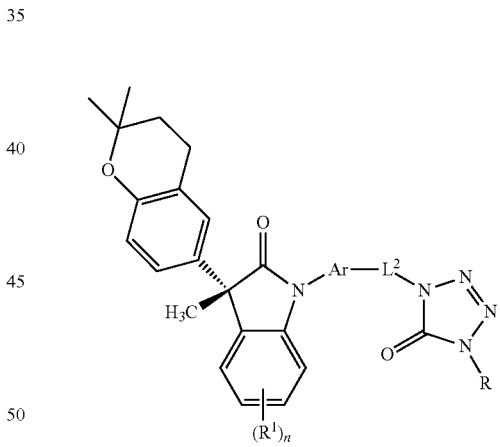

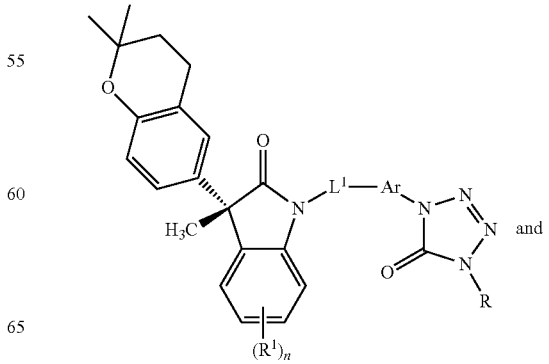

and

-continued

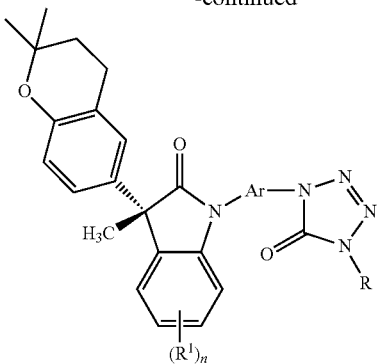

or a pharmaceutically acceptable salt thereof, wherein said compound is substantially free of other isomers.

6. A compound of claim 1, having the formula:

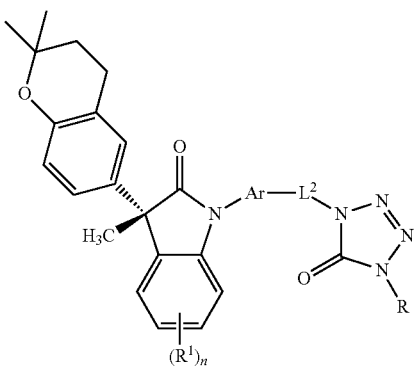

or a pharmaceutically acceptable salt thereof, wherein $L^2$ is $C_{1-3}$ alkylene and wherein said compound is substantially free of other isomers.

7. A compound of claim 1, wherein Ar is selected from benzene, pyridine and quinoline, each of which is optionally substituted with from one to two $R^3$.

8. A compound of claim 1, wherein $L^1$ is selected from the group consisting of a bond, —CH$_2$— and —CH(CH$_3$)—.

9. A compound of claim 1, wherein $L^2$ is selected from the group consisting of a bond, —O—CH$_2$—, —CH(CH$_3$)—, —C(CH$_3$)$_2$—, —CH$_2$CH$_2$—, —CH$_2$—, and —CH$_2$CH$_2$CH$_2$—.

10. A compound of claim 1, wherein n is 1 or 2.

11. A compound of claim 1, wherein m is 1, 2 or 3.

12. A compound of claim 1, having the formula:

(Ia)

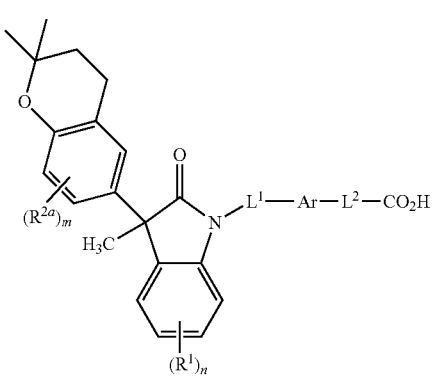

or a pharmaceutically acceptable salt thereof.

13. A compound of claim 12, wherein Ar is selected from benzene, pyridine and quinoline, each of which is optionally substituted with from one to two $R^3$.

14. A compound of claim 12, wherein $L^1$ is selected from the group consisting of a bond, —CH$_2$— and —CH(CH$_3$)—.

15. A compound of claim 12, wherein $L^2$ is selected from the group consisting of a bond, —O—CH$_2$—, —CH(CH$_3$)—, —C(CH$_3$)$_2$—, —CH$_2$CH$_2$—, —CH$_2$—, and —CH$_2$CH$_2$CH$_2$—.

16. A compound of claim 12, having a formula selected from the group consisting of:

(Ia1)

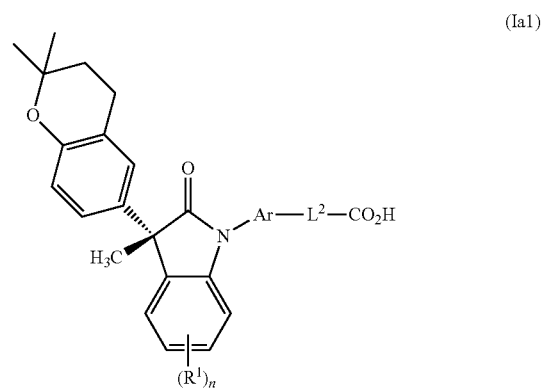

(Ia2)

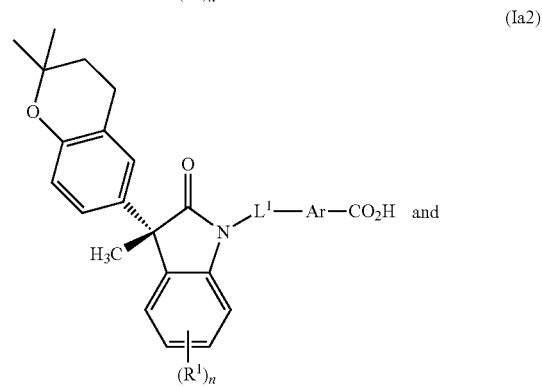

(Ia3)

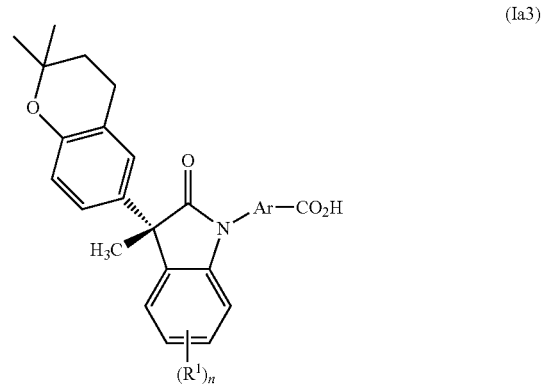

or a pharmaceutically acceptable salt thereof, wherein said compound is substantially free of other isomers.

17. A compound of claim 16, wherein Ar is selected from the group consisting of benzene, pyridine and quinoline, each of which is optionally substituted with from one to two $R^3$.

18. A compound of claim 16, wherein Ar is selected from the group consisting of 1,3-phenylene and 1,4-phenylene, each of which is optionally substituted with from one to two $R^3$.

19. A compound of claim 16, wherein $L^1$ is selected from the group consisting of a bond, —$CH_2$— and —CH($CH_3$)—.

20. A compound of claim 16, wherein $L^2$ is selected from the group consisting of —O—$CH_2$—, —CH($CH_3$)—, —C($CH_3$)$_2$—, —$CH_2CH_2$—, —$CH_2$— and —$CH_2CH_2CH_2$—.

21. A compound of claim 16, wherein $R^1$ is selected from the group consisting of halogen, cyano, $C_{1-3}$ alkyl, $C_{1-3}$ alkoxy, $C_{1-3}$ haloalkyl, $C_{1-3}$ haloalkoxy, $C_{3-5}$ cycloalkyl, and $C_{2-3}$ alkenyl.

22. A compound of claim 16, wherein $R^1$ is selected from the group consisting of chloro, methyl, cyano, ethyl, cyclopropyl, trifluoromethyl and trifluoromethoxy.

23. A compound of claim 16, having a formula selected from the group consisting of:

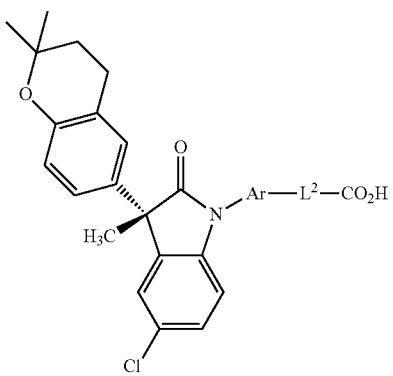
(Ia1')

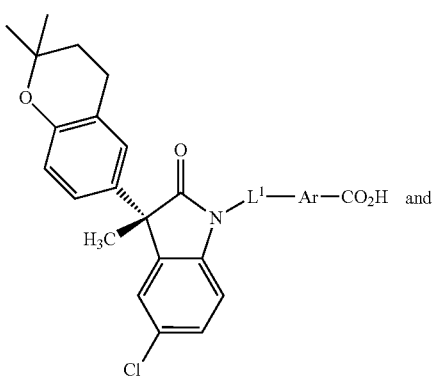
(Ia2')

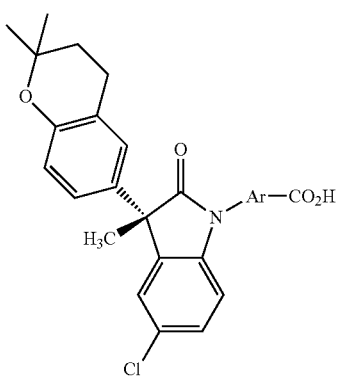
(Ia3')

or a pharmaceutically acceptable salt thereof, wherein said compound is substantially free of other isomers.

24. A compound of claim 1, having the formula:

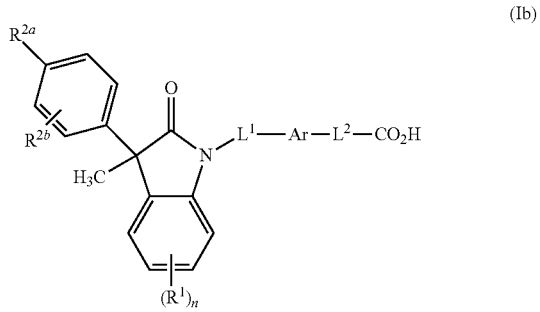
(Ib)

or a pharmaceutically acceptable salt thereof.

25. A compound of claim 24, wherein $R^{2b}$ is hydrogen.

26. A compound of claim 24, wherein Ar is selected from the group consisting of benzene, pyridine and quinoline, each of which is optionally substituted with from one to two $R^3$.

27. A compound of claim 24, wherein $L^1$ is selected from the group consisting of a bond, —$CH_2$— and —CH($CH_3$)—.

28. A compound of claim 24, wherein $L^2$ is selected from the group consisting of a bond, —O—$CH_2$—, —CH($CH_3$)—, —C($CH_3$)$_2$—, —$CH_2CH_2$—, —$CH_2$— and —$CH_2CH_2CH_2$—.

29. A compound of claim 24, having a formula selected from the group consisting of:

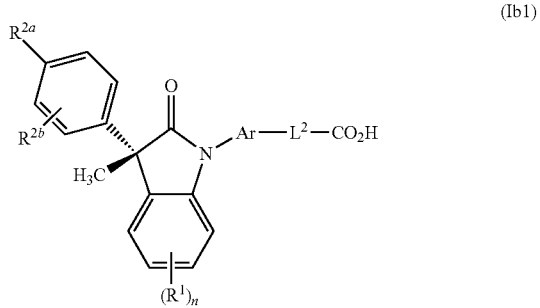
(Ib1)

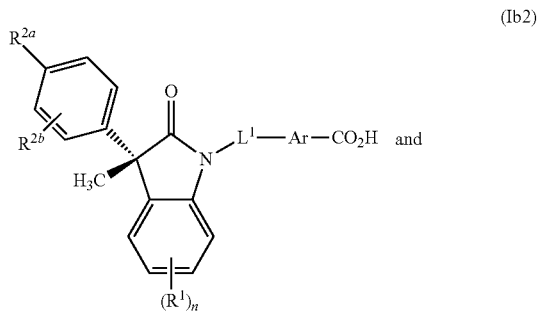
(Ib2)

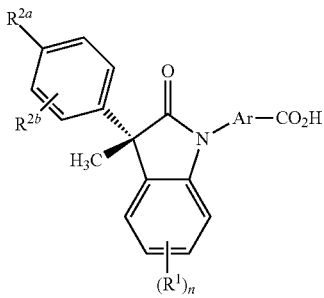

(Ib3)

or a pharmaceutically acceptable salt thereof, wherein said compound is substantially free of other isomers.

30. A compound of claim 29, wherein Ar is selected from the group consisting of benzene, pyridine and quinoline, each of which is optionally substituted with from one to two $R^3$.

31. A compound of claim 29, wherein Ar is selected from the group consisting of 1,3-phenylene and 1,4-phenylene, each of which is optionally substituted with from one to two $R^3$.

32. A compound of claim 29, wherein $R^3$ is selected from the group consisting of $CH_3$, $CH_2CH_3$, $CH_2CH_2CH_3$, $CH(CH_3)_2$ and $CH_2OH$.

33. A compound claim 29, wherein $L^1$ is selected from the group consisting of a bond, —$CH_2$— and —$CH(CH_3)$—.

34. A compound of claim 29, wherein $L^2$ is selected from the group consisting of —O—$CH_2$—, —$CH(CH_3)$—, —$C(CH_3)_2$—, —$CH_2CH_2$—, —$CH_2$— and —$CH_2CH_2CH_2$—.

35. A compound of claim 29, wherein $R^1$ is selected from the group consisting of halogen, cyano, $C_{1-3}$ alkyl, $C_{1-3}$ alkoxy, $C_{1-3}$ haloalkyl, $C_{1-3}$ haloalkoxy, $C_{3-5}$ cycloalkyl, and $C_{2-3}$ alkenyl.

36. A compound of claim 29, wherein $R^1$ is selected from the group consisting of chloro, methyl, cyano, ethyl, cyclopropyl, trifluoromethyl and trifluoromethoxy.

37. A compound of claim 29, having a formula selected from the group consisting of:

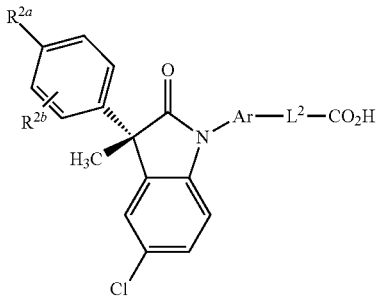

(Ib1')

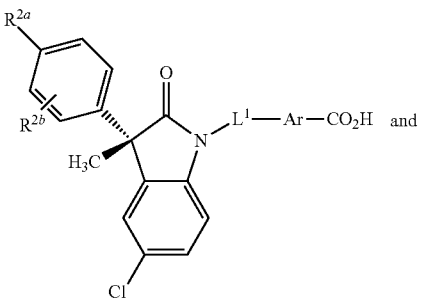

(Ib2')

and

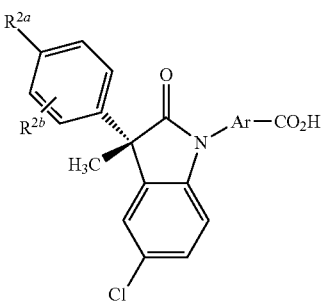

(Ib3')

or a pharmaceutically acceptable salt thereof, wherein said compound is substantially free of other isomers.

38. A compound of claim 1 or a pharmaceutically acceptable salt thereof, having the formula

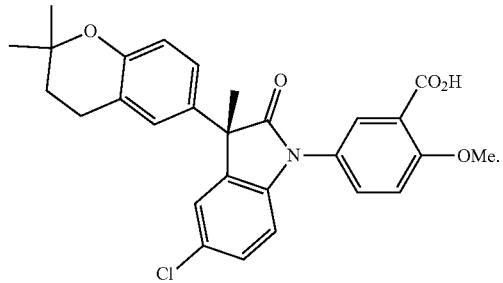 [SMILES: COc1ccc(N2C(=O)[C@@](C)(c3ccc4c(c3)CCC(C)(C)O4)c3cc(Cl)ccc32)cc1C(=O)O]

39. A pharmaceutical composition comprising a pharmaceutically acceptable excipient and at least one compound of claim 1, or a pharmaceutically acceptable salt thereof.

40. A compound of claim 1 or a pharmaceutically acceptable salt thereof, having the formula

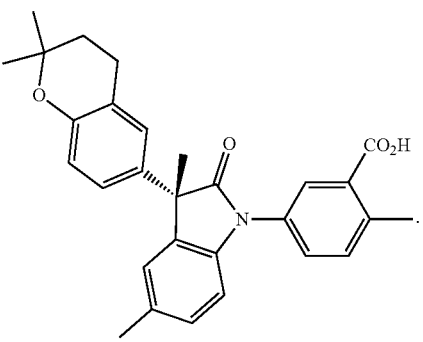

41. A compound of claim 1 or a pharmaceutically acceptable salt thereof, having the formula

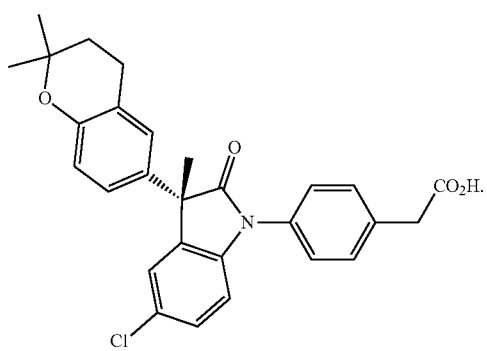 [SMILES: CC1(C)CCc2cc([C@]3(C)C(=O)N(c4ccc(CC(=O)O)cc4)c4ccc(Cl)cc43)ccc2O1]
42. A compound of claim 1 or a pharmaceutically acceptable salt thereof, having the formula
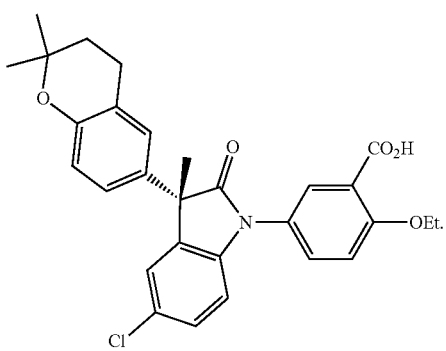 [SMILES: CCOc1ccc(N2C(=O)[C@@](C)(c3ccc4c(c3)CCC(C)(C)O4)c3cc(Cl)ccc32)cc1C(=O)O]
43. A compound of claim 1 or a pharmaceutically acceptable salt thereof, selected from the group consisting of
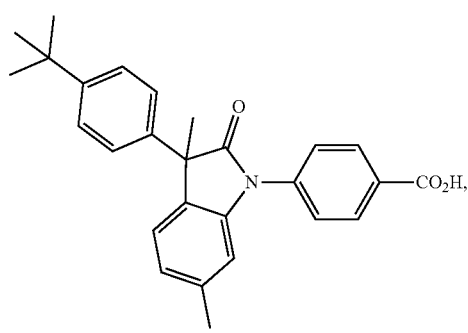
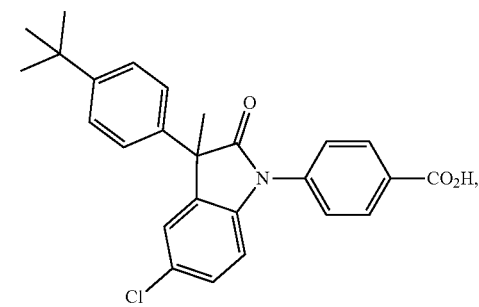
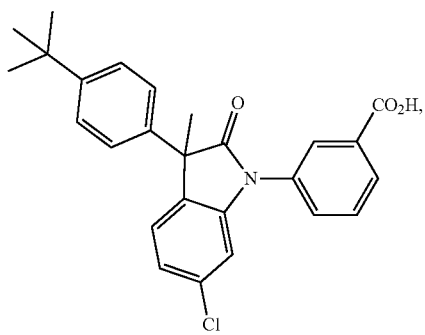
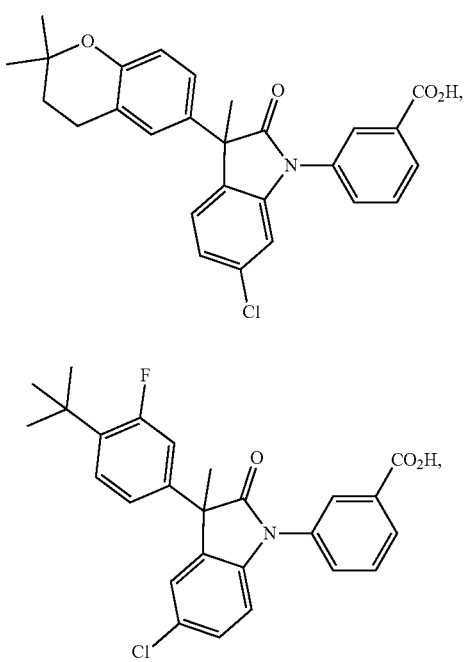
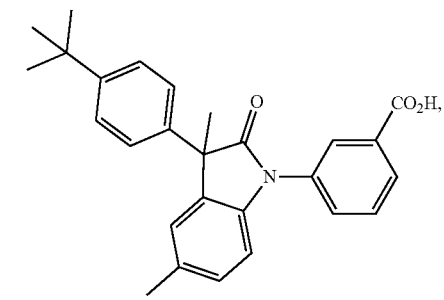

113
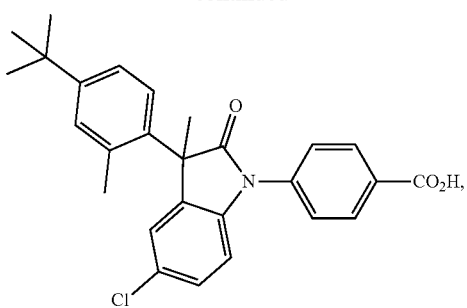
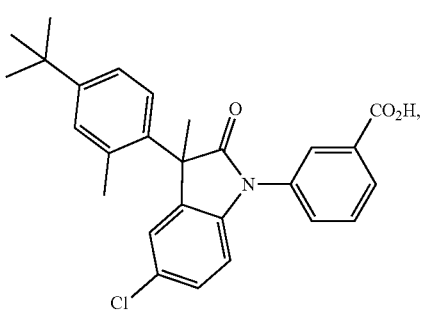
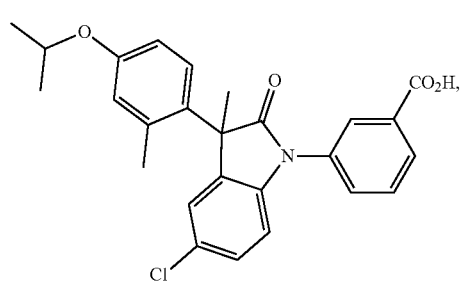
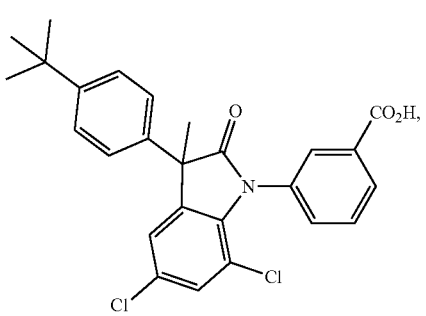
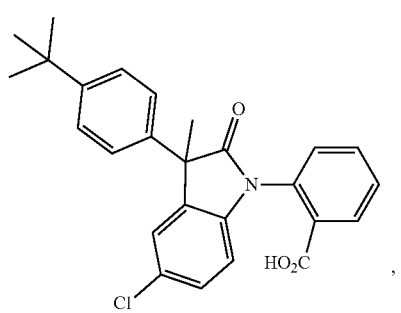
114
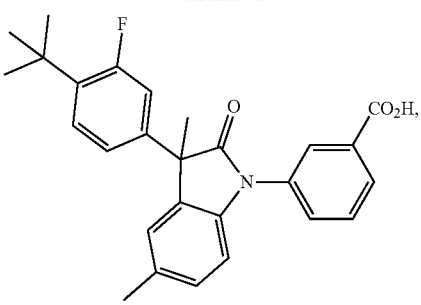
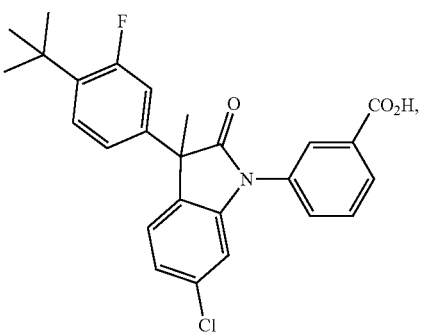
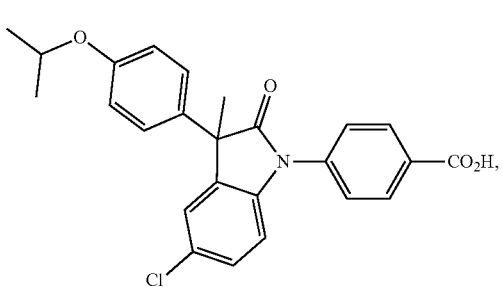
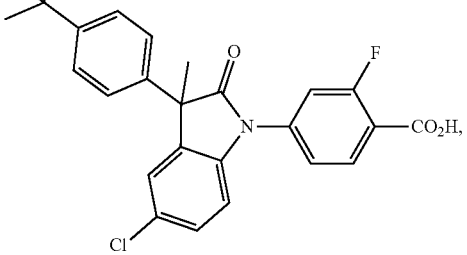
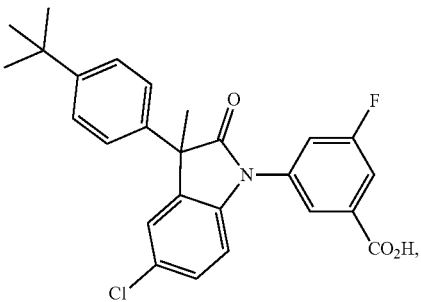

115
-continued
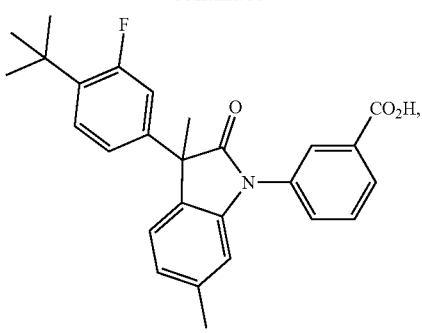
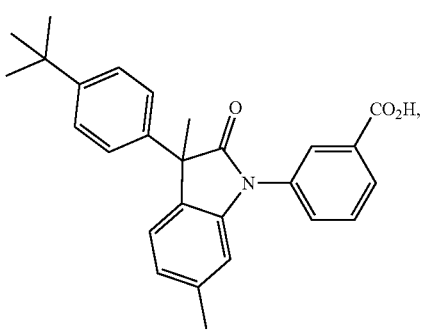
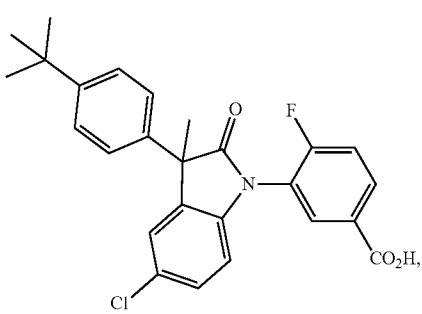
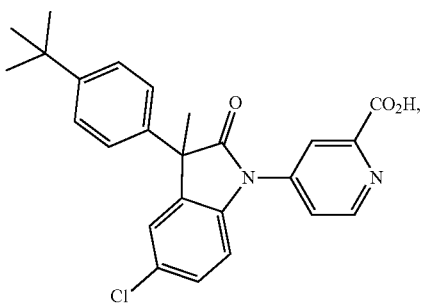
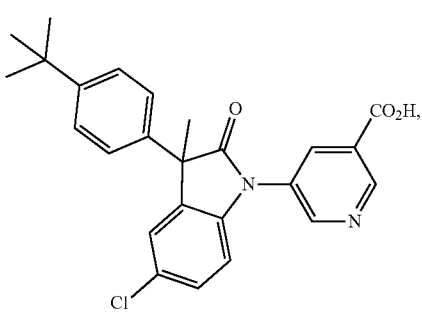
116
-continued
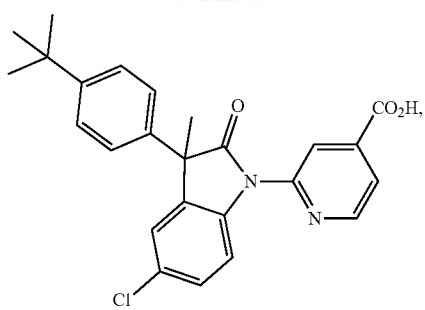
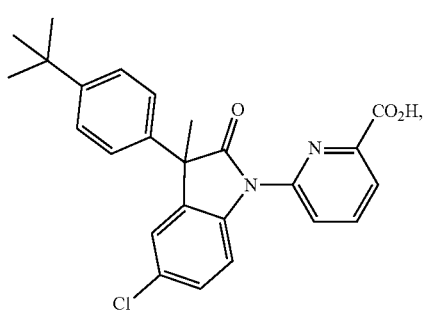
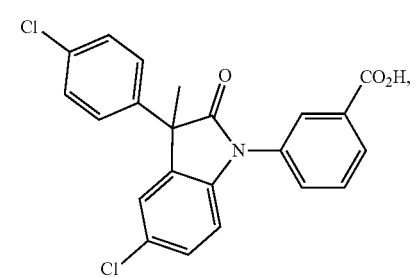
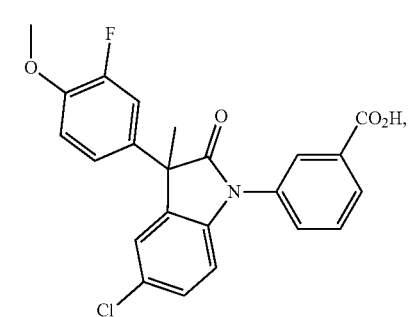
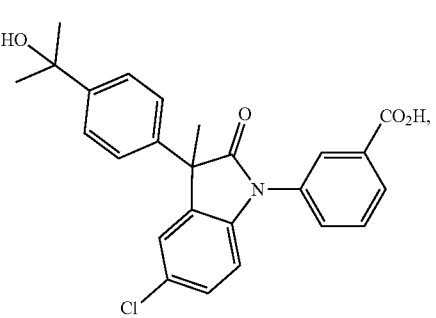

-continued
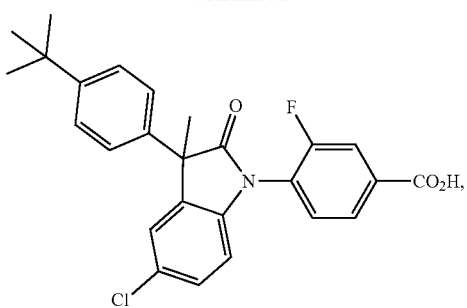
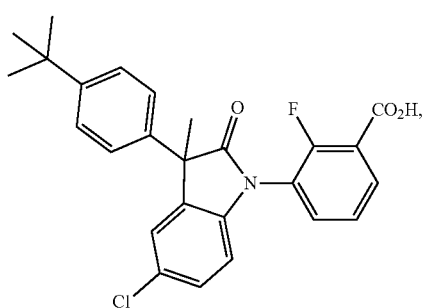
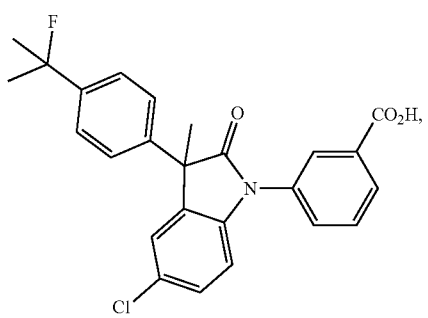
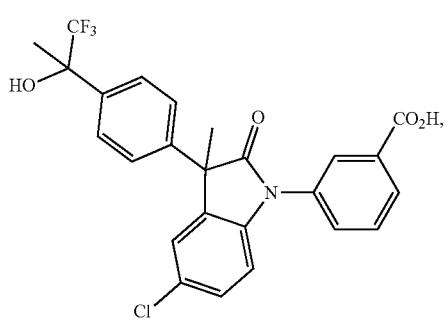
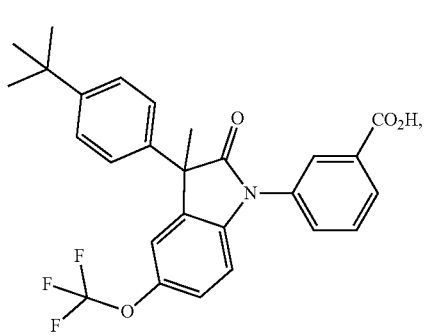
-continued
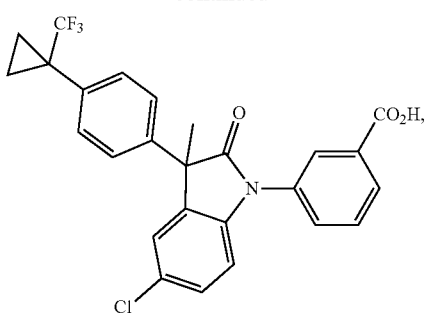
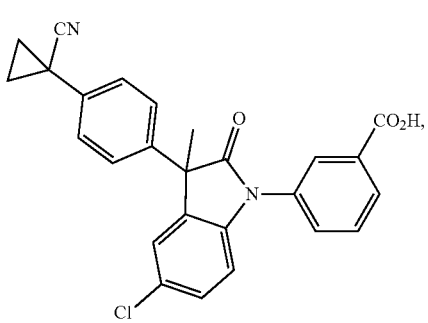
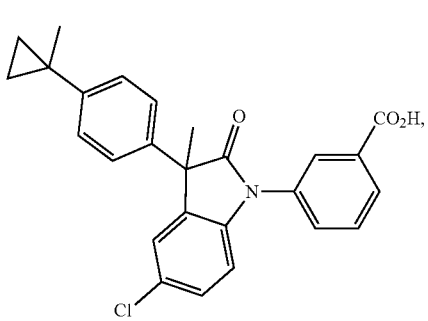
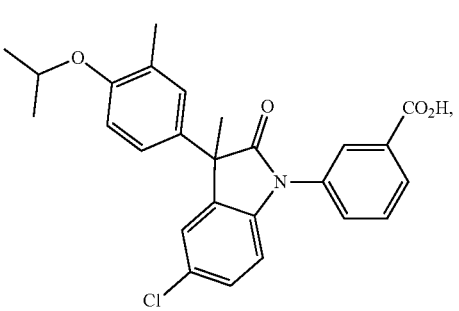
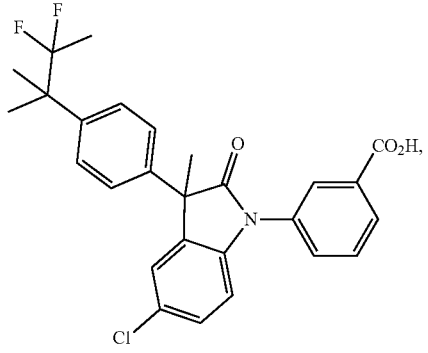

119
-continued
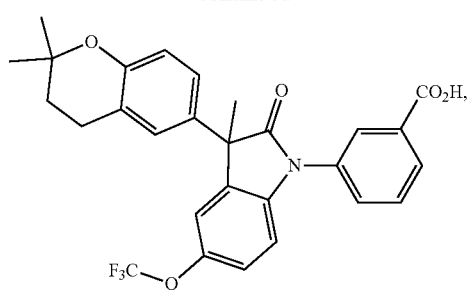
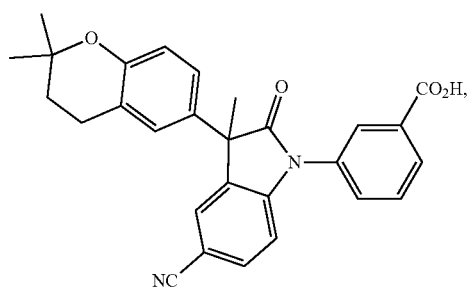
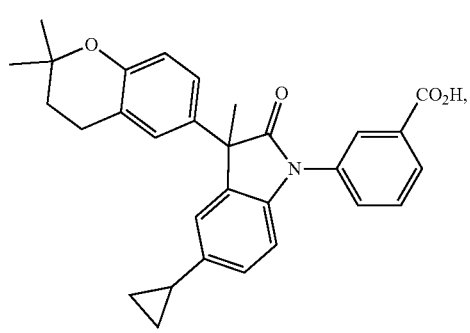
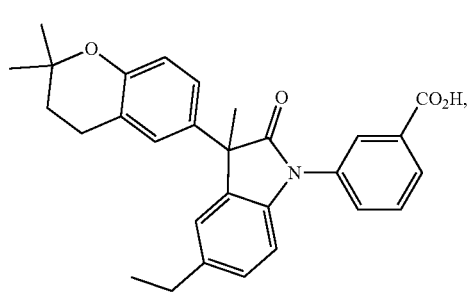
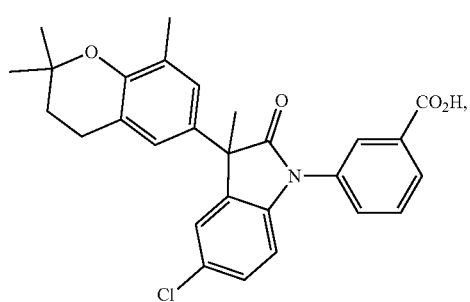
120
-continued
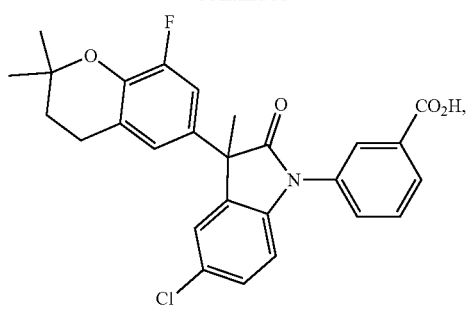
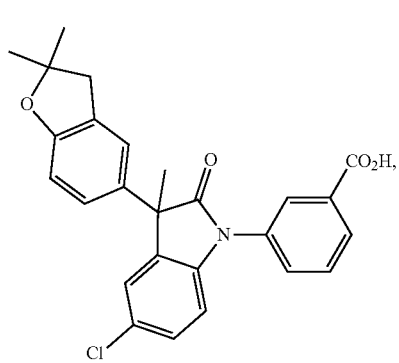
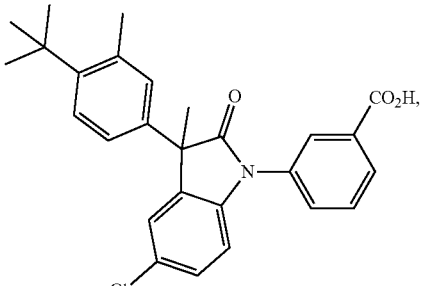
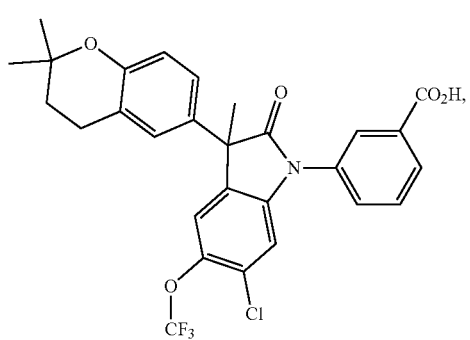
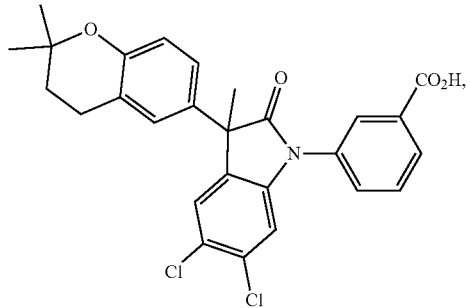

121
-continued
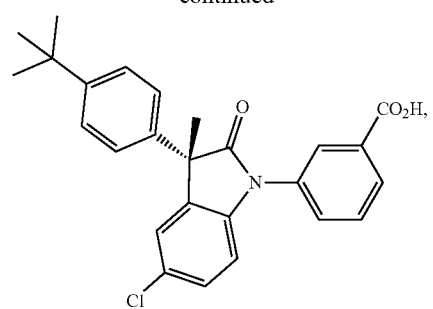
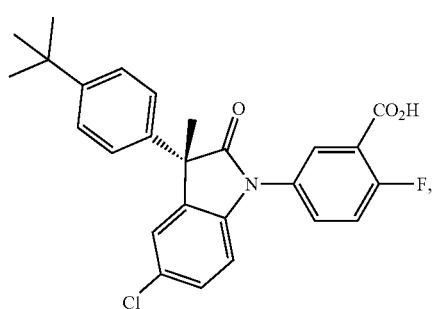
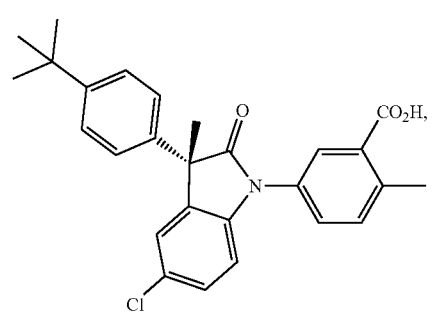
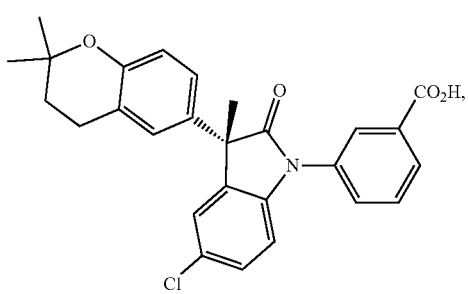
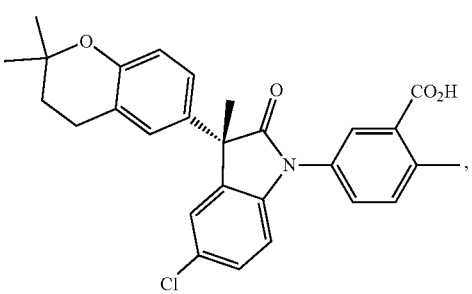
122
-continued
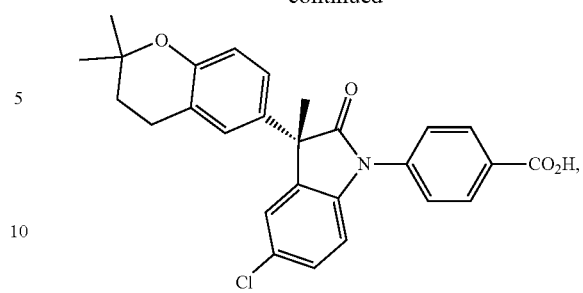
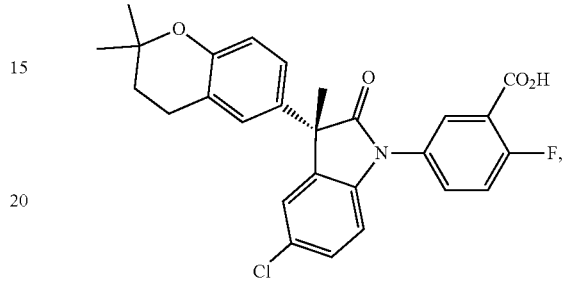
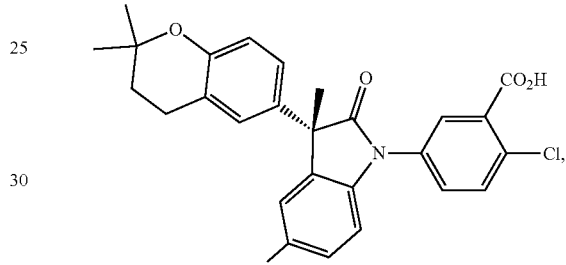
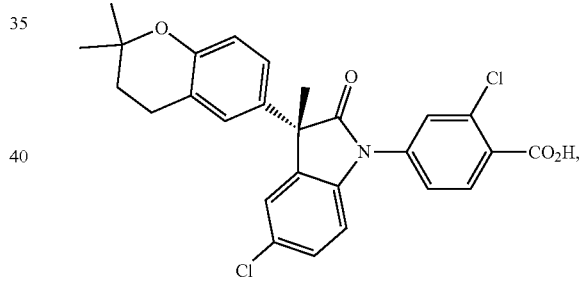
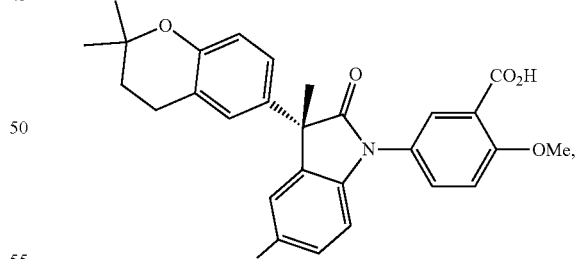
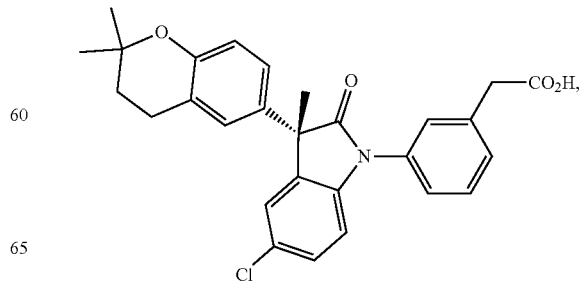

123
-continued
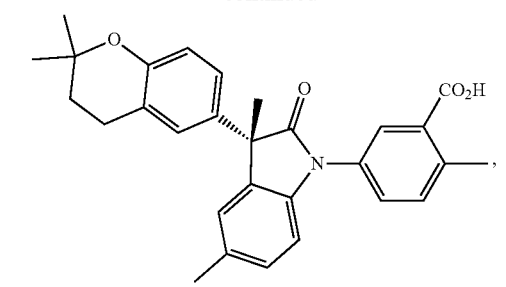
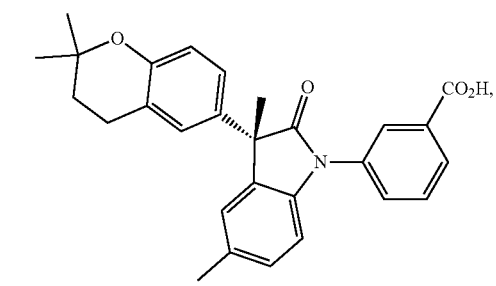
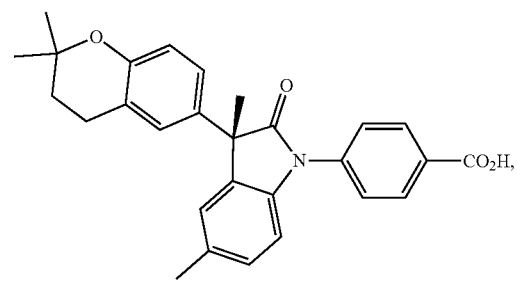
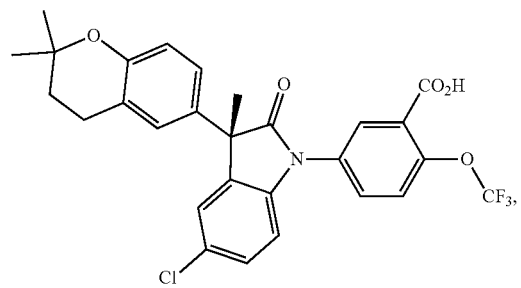
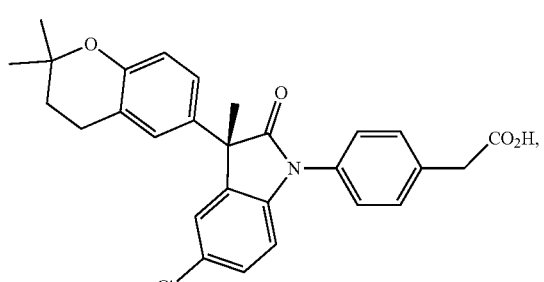
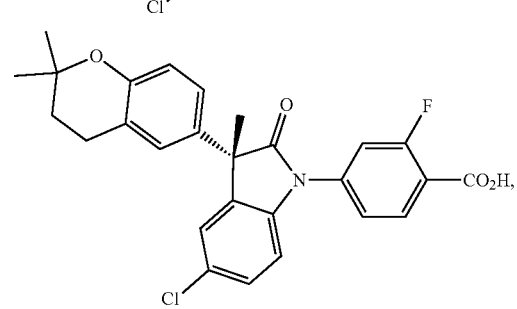
124
-continued
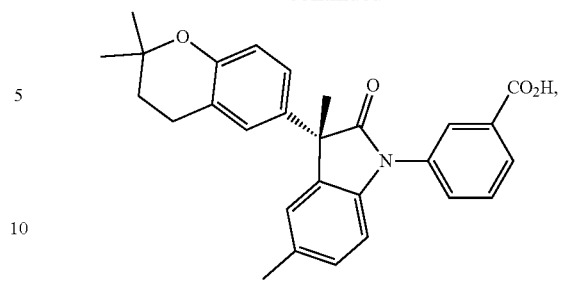
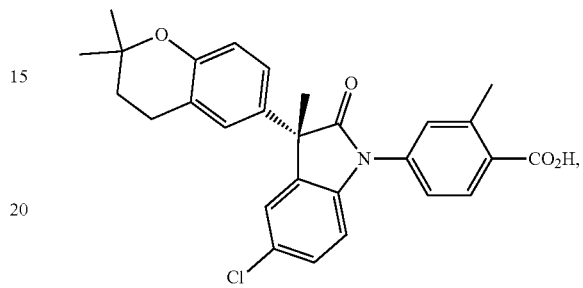
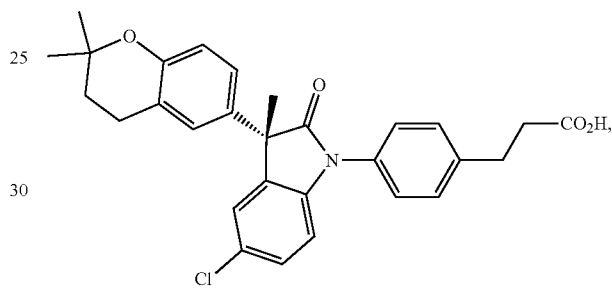
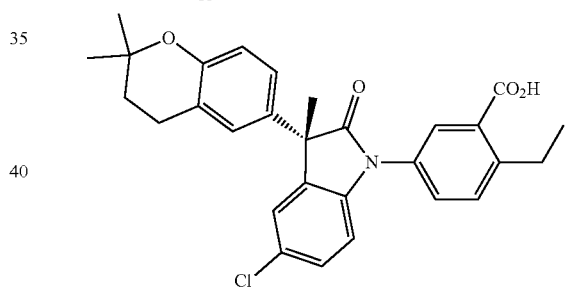
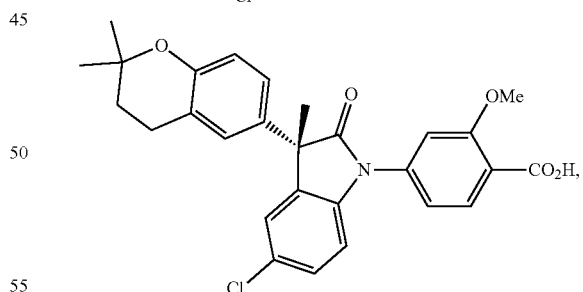
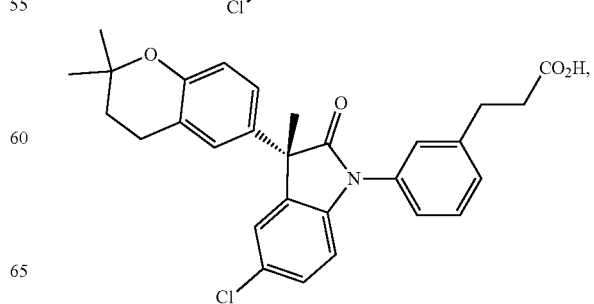

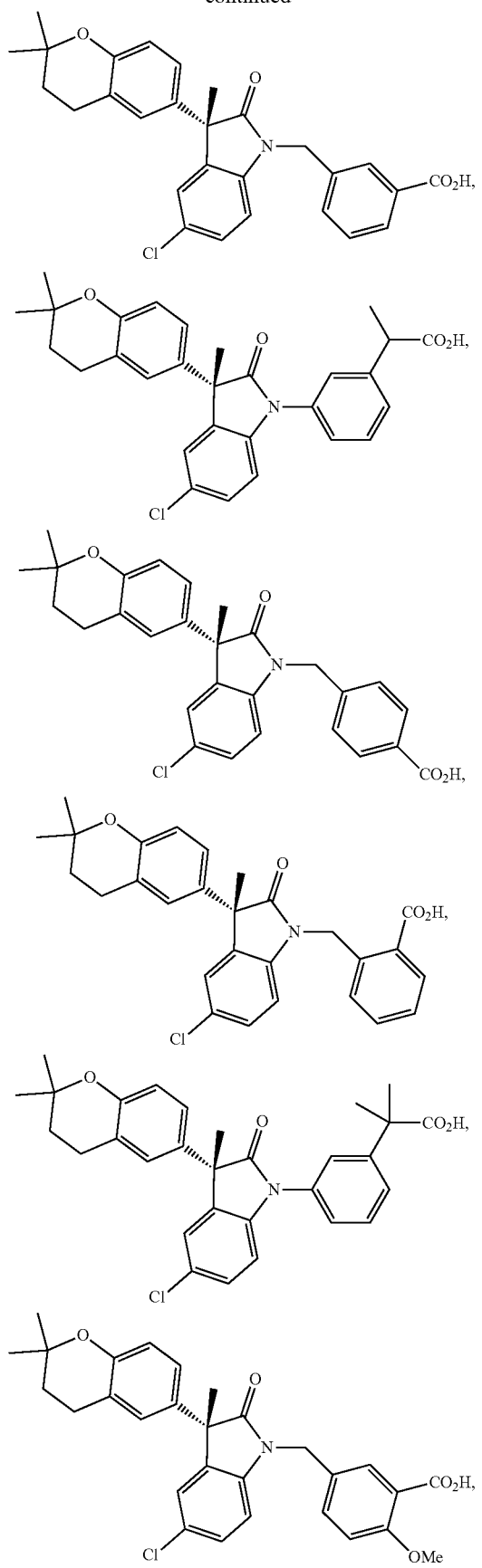
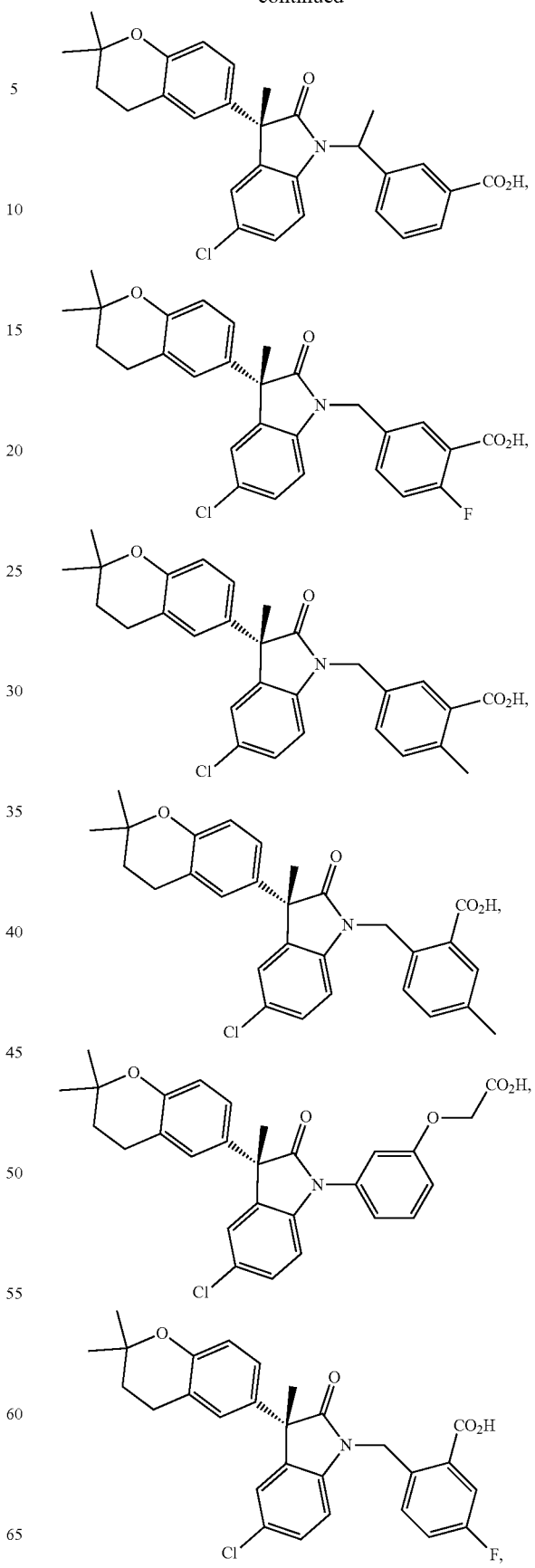

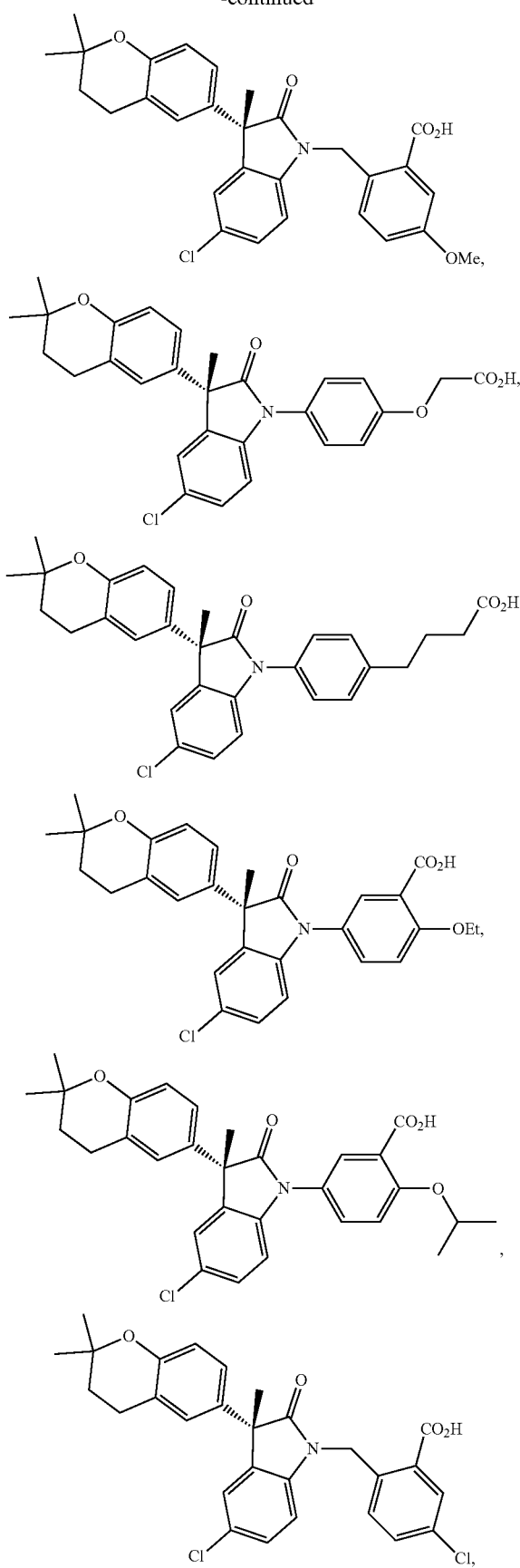
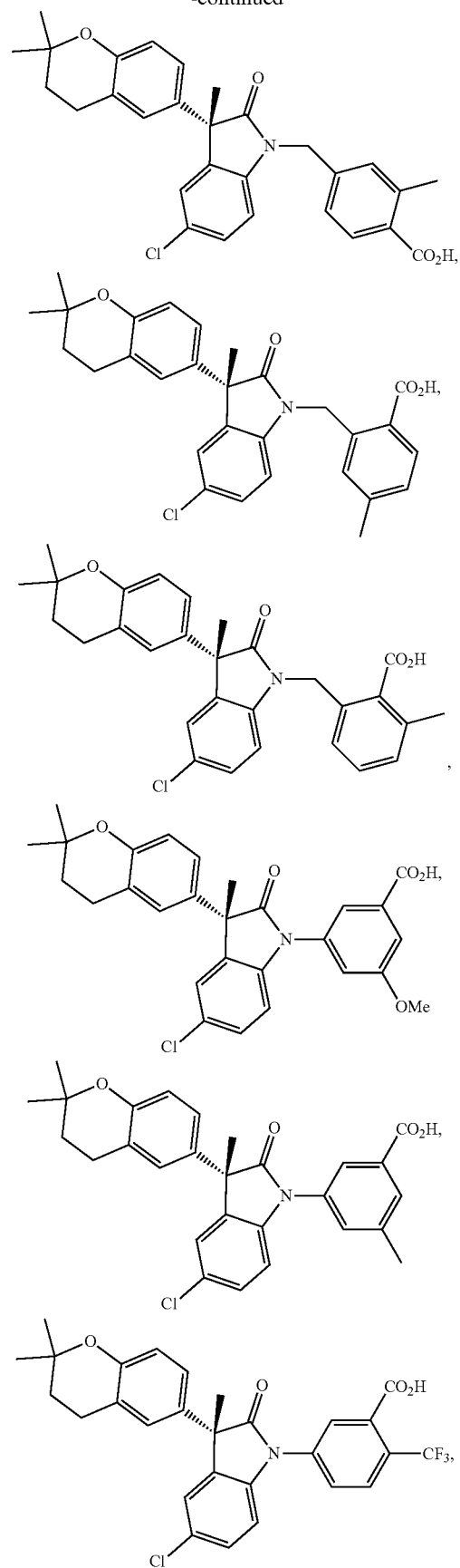

129
-continued
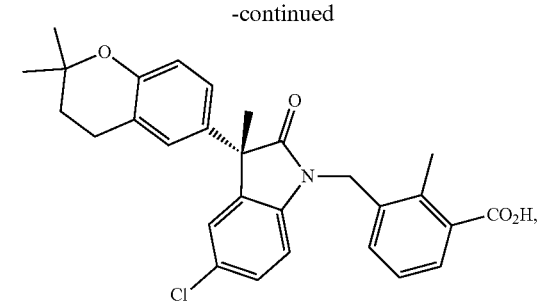
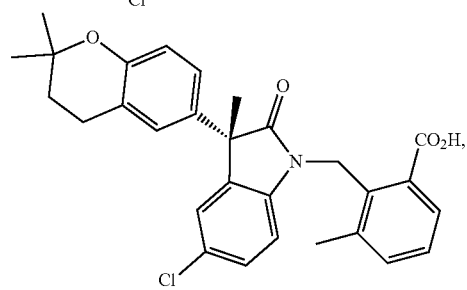
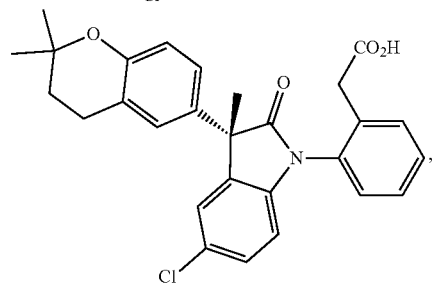
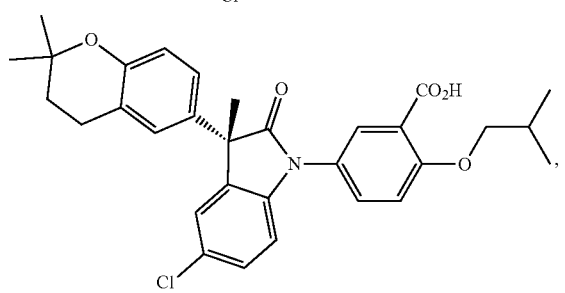
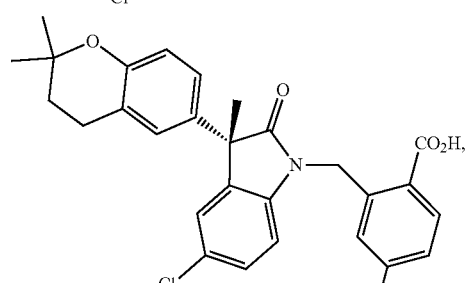
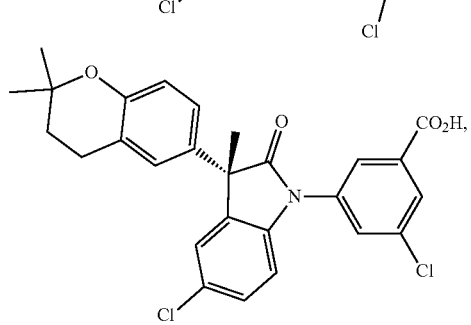
130
-continued
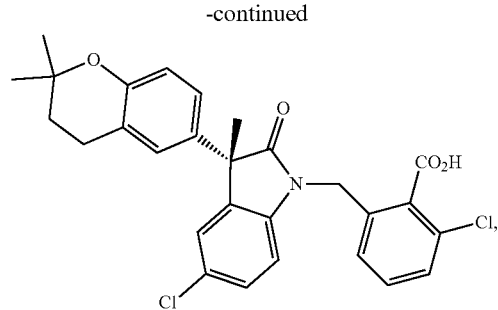
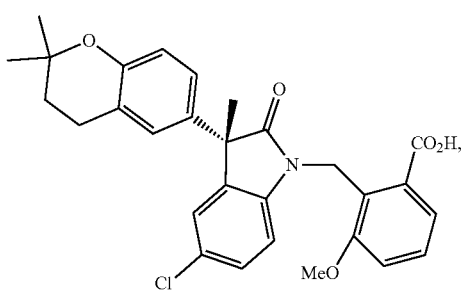
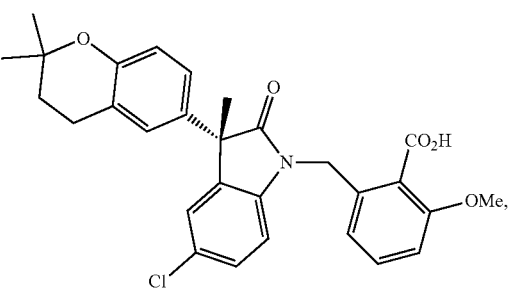
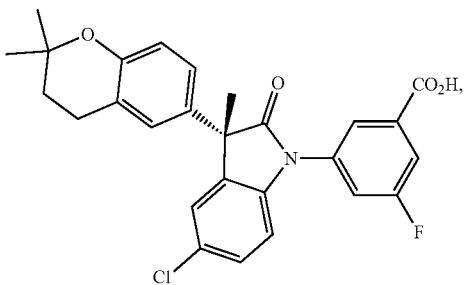
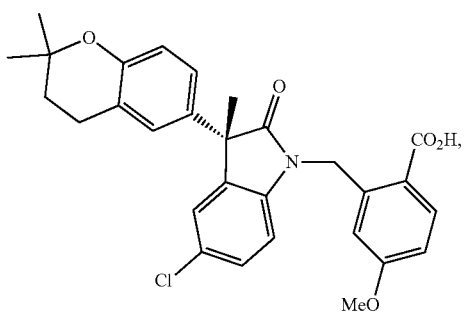

131
-continued
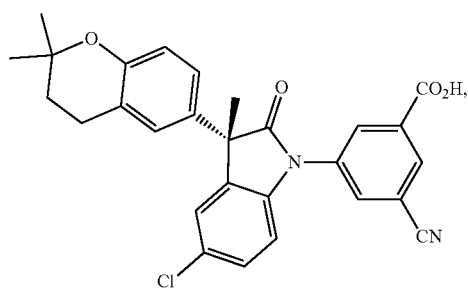
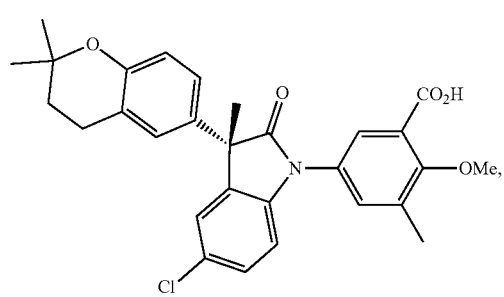
132
-continued
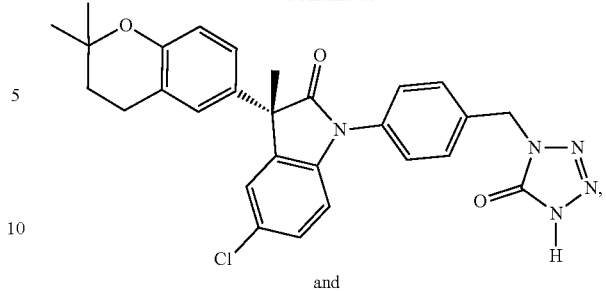
and
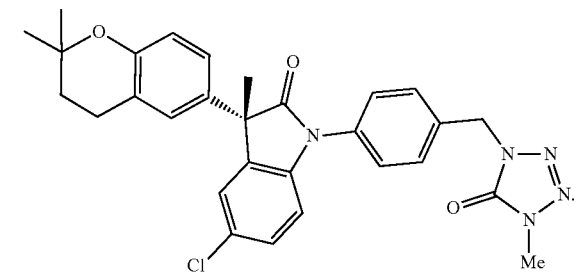
* * * * *